(12) United States Patent
Jaeschke et al.

(10) Patent No.: US 7,414,060 B2
(45) Date of Patent: Aug. 19, 2008

(54) PYRIDINE-2-CARBOXYAMIDE DERIVATIVES

(75) Inventors: Georg Jaeschke, Basel (CH); Sabine Kolczewski, Rheinfelden (DE); Richard Hugh Philip Porter, Reinach (CH); Eric Vieira, Frenkendorf (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 11/360,085

(22) Filed: Feb. 23, 2006

(65) Prior Publication Data

US 2006/0199960 A1 Sep. 7, 2006

(30) Foreign Application Priority Data

Mar. 4, 2005 (EP) .................. 05101701

(51) Int. Cl.
*C07D 401/14* (2006.01)
*A61K 31/4436* (2006.01)

(52) U.S. Cl. .............. 514/256; 514/332; 514/333; 514/336; 514/341; 514/342; 514/354; 544/328; 546/256; 546/262; 546/270.4; 546/275.4; 546/280.4; 546/323

(58) Field of Classification Search ......... 546/256, 546/262, 270.7, 275.4, 280.4, 323; 544/328; 514/256, 332, 333, 336, 341, 342, 354
See application file for complete search history.

(56) References Cited

FOREIGN PATENT DOCUMENTS

| WO | WO 00/26202    | * | 5/2000 |
| WO | WO 2004/007481 | * | 1/2004 |
| WO | WO 2004/076420 |   | 9/2004 |
| WO | WO 2004/081001 |   | 9/2004 |
| WO | WO 2005/079802 | * | 9/2005 |

OTHER PUBLICATIONS

Bonnefous et al., Bioorganic & Medicinal Chemistry Letters, vol. 15, pp. 1197-1200 (2005).
Mutel, V., Expert Opin. Ther. Patents, vol. 12(12) pp. 1845-1852 (2002).
Epsztajn, et al., Synthetic Communications, vol. 27(6), pp. 1075-1086 (1997).
Schlaeger, et al., Cytotechnology, vol. 30, pp. 71-83 (1999).
Porter, et al., British Journal of Pharmacology, vol. 128, pp. 13-20 (1999).
Sanchez, et al., J. Heterocycl. Chem. vol. 24, pp. 215-217 (1987).
Jinaraj, et al., Indian J. Chem., vol. 22B, pp. 841-845 (1983).
Smith, et al., J. Org. Chem. vol. 20, pp. 829-838 (1955).
Iwasaki, et al., J. Med. Chem. vol. 38, pp. 496-507 (1995).
Abstract corresponding to WO 04/081001 (B1), 2004.
Abstract corresponding to WO 04/076420 (B2), 2004.

* cited by examiner

*Primary Examiner*—Deepak Rao
(74) *Attorney, Agent, or Firm*—George W. Johnston; Patricia S. Rocha-Tramaloni; Kimberly J. Prior

(57) ABSTRACT

The invention relates to compounds of formula I:

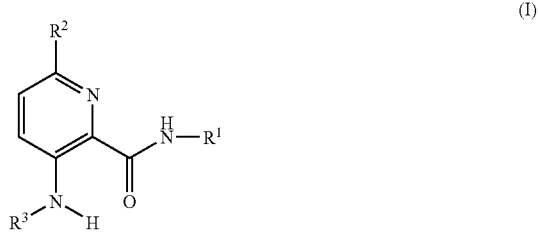

wherein $R^1$ to $R^3$ are as defined in the specification, to processes for their preparation, to pharmaceutical compositions containing them, and to methods for treating CNS disorders.

19 Claims, No Drawings

PYRIDINE-2-CARBOXYAMIDE DERIVATIVES

PRIORITY TO RELATED APPLICATIONS

This application claims the benefit of European Application No. 05101701.0, filed Mar. 4, 2005, which is hereby incorporated by reference in its entirety.

BACKGROUND OF THE INVENTION

In the central nervous system (CNS) the transmission of stimuli takes place by the interaction of a neurotransmitter, which is sent out by a neuron, with a neuroreceptor. Glutamate is the major excitatory neurotransmitter in the brain and plays a unique role in a variety of central nervous system (CNS) functions. The glutamate-dependent stimulus receptors are divided into two main groups. The first main group, namely the ionotropic receptors, forms ligand-controlled ion channels. The metabotropic glutamate receptors (mGluR) belong to the second main group and, furthermore, belong to the family of G-protein coupled receptors.

At present, eight different members of these mGluR family are known and of these some even have sub-types. According to their sequence homology, signal transduction mechanisms and agonist selectivity, these eight receptors can be sub-divided into three sub-groups: mGluR1 and mGluR5 belong to group I, mGluR2 and mGluR3 belong to group II and mGluR4, mGluR6, mGluR7 and mGluR8 belong to group III.

Ligands of metabotropic glutamate receptors belonging to the first group can be used for the treatment or prevention of acute and/or chronic neurological disorders such as psychosis, epilepsy, schizophrenia, Alzheimer's disease, cognitive disorders and memory deficits, as well as chronic and acute pain.

Other treatable indications in this connection are restricted brain function caused by bypass operations or transplants, poor blood supply to the brain, spinal cord injuries, head injuries, hypoxia caused by pregnancy, cardiac arrest and hypoglycaemia. Further treatable indications are gastroesophageal reflux disease (GERD), fragile X syndrome, ischemia, Huntington's chorea, amyotrophic lateral sclerosis (ALS), dementia caused by AIDS, eye injuries, retinopathy, idiopathic parkinsonism or parkinsonism caused by medicaments as well as conditions which lead to glutamate-deficiency functions, such as e.g. muscle spasms, convulsions, migraine, urinary incontinence, obesity, nicotine addiction, opiate addiction, anxiety, vomiting, dyskinesia and depressions.

Disorders mediated full or in part by mGluR5 are for example acute, traumatic and chronic degenerative processes of the nervous system, such as Alzheimer's disease, senile dementia, Parkinson's disease, Huntington's chorea, amyotrophic lateral sclerosis and multiple sclerosis, psychiatric diseases such as schizophrenia and anxiety, depression, pain and drug dependency (*Expert Opin. Ther. Patents* (2002), 12, (12)).

SUMMARY OF THE INVENTION

The present invention provides novel pyridine-2-carboxamide derivatives of formula (I) useful as metabotropic glutamate receptor antagonists:

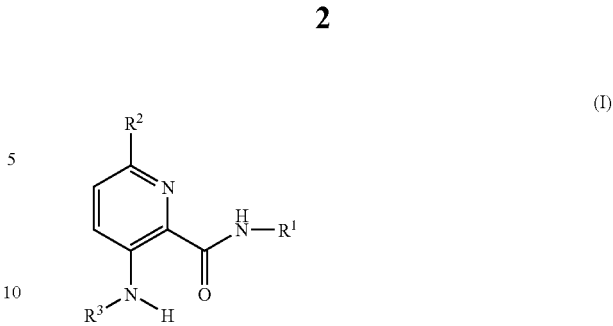

wherein
$R^1$ is a 5- or 6-membered ring respectively of formulae (II) or (III):

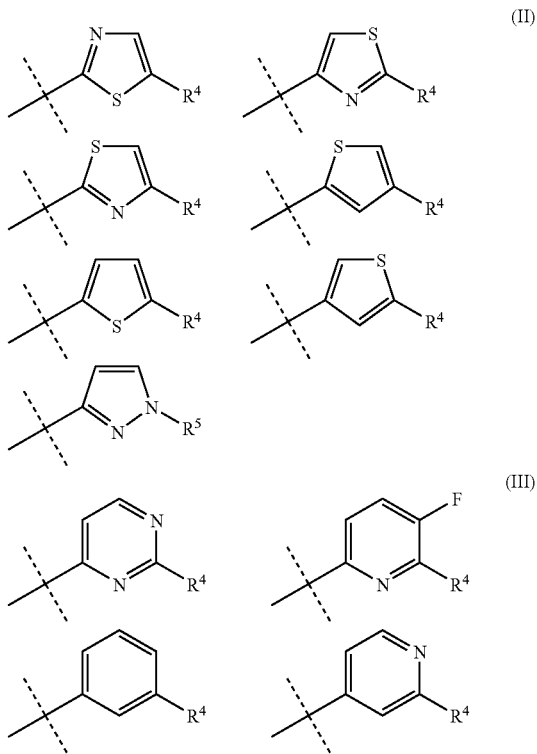

$R^2$ is H, Cl, $C_1$-$C_7$-alkyl, $C_3$-$C_6$-cycloalkyl or —$(CH_2)_m$—$R^a$;
$R^3$ is aryl or heteroaryl each of which is optionally substituted by:
  CN, Cl, F, Br, $CF_3$, $CHF_2$, —O—$C_1$-$C_7$-alkyl, —(CO)—$R^b$, —$(CH_2)_m$—$R^c$, —NH—(CO)—$C_1$-$C_7$-alkyl, —O—$CH_2F$, —O—$CHF_2$, —O—$CF_3$, —$S(O)_2$—$R^d$, $C_3$-$C_6$-cycloalkyl, or heteroaryl which is optionally substituted by $C_1$-$C_7$-alkyl;
$R^4$ is H, —OH, Cl, F, Br, CN, —$CHF_2$, $CF_3$, $C_1$-$C_7$-alkyl, —$C_3$-$C_6$-cycloalkyl, —O—(CO)—$C_1$-$C_7$-alkyl, $C_3$-$C_6$-cycloalkyl, or —$(CH_2)_m$—$R^e$;
$R^5$ is $C_1$-$C_7$-alkyl, $C_1$-$C_7$-alkyl-$C_3$-$C_6$-cycloalkyl, —$(CH_2)_n$—O—$R^f$, $C_3$-$C_8$-alkenyl-O—$R^f$, $(CH_2)_n$—$NR^gR^h$, —$C_2$-$C_6$-alkenyl-$NR^gR^h$, or —$(CH_2)_n$—$R^e$;
$R^a$ is —O—$C_1$-$C_7$-alkyl or —OH;
$R^b$ is $C_1$-$C_7$-alkyl, $NH_2$, or —O—$C_1$-$C_7$-alkyl;
$R^c$ is —OH, $NH_2$, or NH—(CO)—O—$C_1$-$C_7$-alkyl;
$R^d$ is $C_1$-$C_7$-alkyl, —$NH_2$, —NH—$C_1$-$C_7$-alkyl, or —N-di($C_1$-$C_7$-alkyl);

$R^e$ is —OH, —CH$_2$F, —CHF$_2$, —CF$_3$, —O—(CO)—C$_1$-C$_7$-alkyl, or —C$_3$-C$_6$-cycloalkyl;

$R^f$ is C$_1$-C$_7$-alkyl, C$_3$-C$_8$-alkenyl, C$_3$-C$_6$-cycloalkyl, phenyl, benzyl, or —(CO)—R';

$R^g$ and $R^h$ are each independently H, C$_1$-C$_7$-alkyl, C$_3$-C$_6$-cycloalkyl, C$_3$-C$_8$-alkenyl, phenyl, benzyl, or —(CO)—R' or $R^g$ and $R^h$, together with the nitrogen atom to which they are attached, form a 5- to 7-membered heterocyclic or heteroaryl ring optionally substituted with 1 or 2 OH;

R' is NH$_2$, —NH—C$_1$-C$_7$-alkyl, C$_1$-C$_7$-alkyl, or C$_1$-C$_7$-alkoxy;

m is 1 to 4; and n is 2 to 6;

as well as pharmaceutically acceptable salts thereof.

Bonnefous et al. in Dipyridyl amides: potent metabotropic glutamate subtype 5 (mGlu5) receptor antagonists; *Bioorganic & Medicinal chemistry Letters*, 2005, described compounds useful as group I metabotropic glutamate receptor antagonists without disclosing the compounds of the instant invention. Furthermore, Bonnefous et al. disclosed that generally compounds of formula (I) where $R^1$ is pyridine-3-yl or pyridine-4-yl are inactive.

Contrary to this finding, the 5-position of said pyridine-2-yl compounds are indeed amenable to substitution by a fluorine atom, and the resulting compounds of formula I where $R^1$ is pyridine-4-yl are active as mGluR5 receptor antagonists. In addition, further pyridine-2-carboxyamide derivatives other than pyridine-2-yl derivatives are active as mGluR5 receptor antagonists.

Compounds of general formula I are metabotropic glutamate receptor antagonists. Compounds of formula I are distinguished by having valuable therapeutic properties. They can be used for the treatment of mGluR5 receptor mediated disorders.

The present invention also provides pharmaceutical compositions containing compounds of the invention and methods for preparing the compounds and compositions of the invention. The invention further provides methods for treating mGluR5 receptor mediated disorders. For example, the invention provides methods for treating acute and/or chronic neurological disorders, in particular anxiety and chronic or acute pain.

DETAILED DESCRIPTION OF THE INVENTION

The following definitions of general terms used in the present description apply irrespective of whether the terms in question appear alone or in combination. It must be noted that, as used in the specification and the appended claims, the singular forms "a," "an," and "the" include plural forms unless the context clearly dictates otherwise.

"Aryl" means a monovalent cyclic aromatic hydrocarbon moiety consisting of a mono-, bi- or tricyclic aromatic ring. Preferred aryl groups are C$_6$-C$_{10}$ aryl. The aryl group can be optionally substituted as defined herein. Examples of aryl moieties include, but are not limited to, optionally substituted phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof.

"C$_1$-C$_7$ alkyl" denotes a straight- or branched-carbon chain group containing from 1 to 7 carbon atoms, for example, methyl, ethyl, propyl, isopropyl, isobutyl, sec-butyl, tert-butyl, pentyl, and n-hexyl as well as those specifically illustrated by the examples herein below.

"C$_1$-C$_7$ alkoxy" denotes a group wherein the alkyl group is as defined above and is connected via an oxygen atom.

"C$_3$-C$_8$ alkenyl" denotes a straight- or branched- chain unsaturated hydrocarbon residue having 3-8 carbon atoms, such as ethenyl, 2-propenyl, and isobutene-1-yl, as well as those specifically illustrated by the examples herein below.

"Halogen" denotes chlorine, iodine, fluorine and bromine.

"Heteroaryl" means a monocyclic, bicyclic or tricyclic radical of 5 to 12, preferably 5 to 9, ring atoms having at least one aromatic ring and furthermore containing one, two, or three ring heteroatoms selected from N, O, or S, the remaining ring atoms being C. Heteroaryl can optionally be substituted with one, two, three or four substituents, wherein each substituent is independently hydroxy, cyano, alkyl, alkoxy, thioalkyl, halo, haloalkyl, hydroxyalkyl, alkoxycarbonyl, amino, acetyl, —NHCOOC(CH$_3$)$_3$ or halogen substituted benzyl, or for the non aromatic part of cyclic ring also by oxo, unless otherwise specifically indicated. Examples of heteroaryl moieties include, but are not limited to, optionally substituted imidazolyl, optionally substituted oxazolyl, optionally substituted thiazolyl, optionally substituted pyrazinyl, optionally substituted pyrrolyl, optionally substituted pyrazinyl, optionally substituted pyridinyl, optionally substituted pyrimdinyl, optionally substituted indonyl, optionally substituted isoquinolinyl, optionally substituted carbazol-9-yl, optionally substituted furanyl, optionally substituted benzofuranyl, optionally substituted benzo[1,2,3]thiadiazolyl, optionally substituted benzo[b]thiophenyl, optionally substituted 9H-thioxanthenyl, optionally substituted thieno[2,3-c]pyridinyl and the like or those which are specifically exemplified herein.

"C$_3$-C$_6$ cycloalkyl" denotes a carbon ring having 3 to 6 carbon atoms as ring members and includes, but is not limited to, cyclopropyl, cyclobutyl, cyclopentyl, and cyclohexyl, as well as those groups specifically illustrated by the examples herein below.

"5- to 7-membered heterocyclic" denotes a saturated cyclic ring comprising from 1 to 6 carbon atoms as ring members, the other remaining ring member atoms being selected from one or more O, N, and S. Preferred 5 to 7 membered heterocycloalkyl groups are 5 or 6 membered heterocycloalkyl groups. Examples of 5 to 7 and 5 or 6 membered heterocycloalkyl groups include, but are not limited to, optionally substituted piperidinyl, piperazinyl, homopiperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiomorpholinyl, thiomorpholinylsulfoxide, thiomorpholinylsulfone, dihydroquinolinyl, dihydrisoquinolinyl, tetrahydroquinolinyl, tetrahydroisoquinolinyl, 1-oxo-thiomorpholin, 1,1-dioxo-thiomorpholin, 1,4-diazepane, and 1,4-oxazepane as well as those groups specifically illustrated by the examples herein below.

"Pharmaceutically acceptable," such as pharmaceutically acceptable carrier, excipient, etc., means pharmaceutically acceptable and substantially non-toxic to the subject to which the particular compound is administered.

The term "pharmaceutically acceptable salt" refers to any salt derived from an inorganic or organic acid or base.

"Therapeutically effective amount" means an amount that is effective to prevent, alleviate, or ameliorate symptoms of diseases or prolong the survival of the subject being treated.

The present invention provides novel pyridine-2-carboxyamide derivatives of formula (I) useful as metabotropic glutamate receptor antagonists:

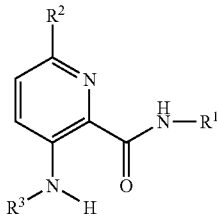

wherein
R¹ is a 5- or 6-membered ring respectively of formulae (II) or (III):

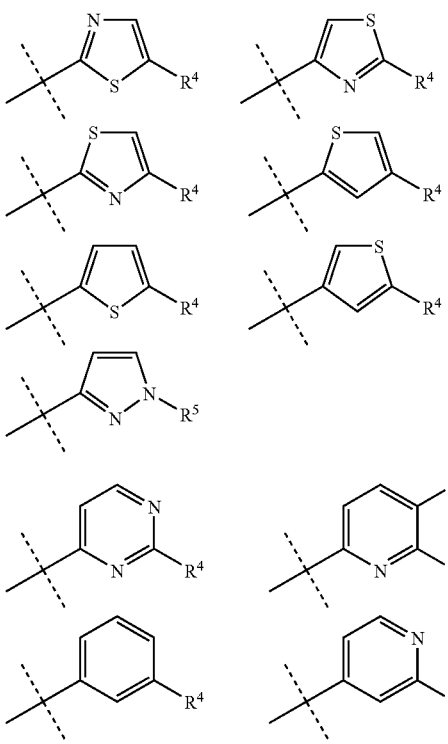

R² is H, Cl, $C_1$-$C_7$-alkyl, $C_3$-$C_6$-cycloalkyl or —$(CH_2)_m$—$R^a$;
R³ is aryl or heteroaryl each of which is optionally substituted by:
 CN, Cl, F, Br, $CF_3$, $CHF_2$, —O—$C_1$-$C_7$-alkyl, —(CO)—$R^b$, —$(CH_2)_m$—$R^c$, —NH—(CO)—$C_1$-$C_7$-alkyl, —O—$CH_2F$, —O—$CHF_2$, —O—$CF_3$, —$S(O)_2$—$R^d$, $C_3$-$C_6$-cycloalkyl, or heteroaryl which is optionally substituted by $C_1$-$C_7$-alkyl;
R⁴ is H, —OH, Cl, F, Br, CN, —$CHF_2$, $CF_3$, $C_1$-$C_7$-alkyl, —$C_3$-$C_6$-cycloalkyl, —O—(CO)—$C_1$-$C_7$-alkyl, $C_3$-$C_6$-cycloalkyl, or —$(CH_2)_m$—$R^e$;
R⁵ is $C_1$-$C_7$-alkyl, $C_1$-$C_7$-alkyl-$C_3$-$C_6$-cycloalkyl, —$(CH_2)_n$—O—$R^f$, $C_3$-$C_8$-alkenyl-O—$R^f$, —$(CH_2)_n$—$NR^gR^h$, —$C_2$-$C_6$-alkenyl-$NR^gR^h$, or —$(CH_2)_n$—$R^e$;
$R^a$ is —O—$C_1$-$C_7$-alkyl or —OH;
$R^b$ is $C_1$-$C_7$-alkyl, $NH_2$, or —O—$C_1$-$C_7$-alkyl;
$R^c$ is —OH, $NH_2$, or NH—(CO)—O—$C_1$-$C_7$-alkyl;
$R^d$ is $C_1$-$C_7$-alkyl, —$NH_2$, —NH—$C_1$-$C_7$-alkyl, or —N-di($C_1$-$C_7$-alkyl);
$R^e$ is —OH, —$CH_2F$, —$CHF_2$, —$CF_3$, —O—(CO)—$C_1$-$C_7$-alkyl, or —$C_3$-$C_6$-cycloalkyl;
$R^f$ is $C_1$-$C_7$-alkyl, $C_3$-$C_8$-alkenyl, $C_3$-$C_6$-cycloalkyl, phenyl, benzyl, or —(CO)—R';
$R^g$ and $R^h$ are each independently H, $C_1$-$C_7$-alkyl, $C_3$-$C_6$-cycloalkyl, $C_3$-$C_8$-alkenyl, phenyl, benzyl, or —(CO)—R' or $R^g$ and $R^h$, together with the nitrogen atom to which they are attached, form a 5- to 7-membered heterocyclic or heteroaryl ring optionally substituted with 1 or 2 OH;
R' is $NH_2$, —NH—$C_1$-$C_7$-alkyl, $C_1$-$C_7$-alkyl, or $C_1$-$C_7$-alkoxy;
m is 1 to 4; and
n is 2 to 6;
as well as pharmaceutically acceptable salts thereof.

In one embodiment, the invention provides compounds of formula (I)

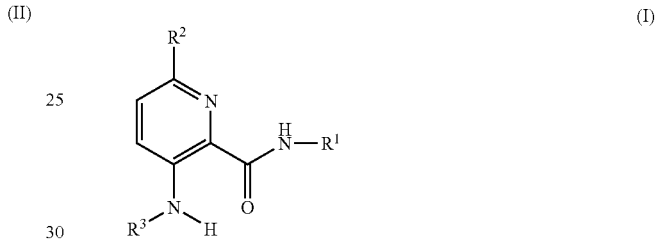

wherein
R¹ is a 5- or 6-membered ring respectively of formulae (II) or (III):

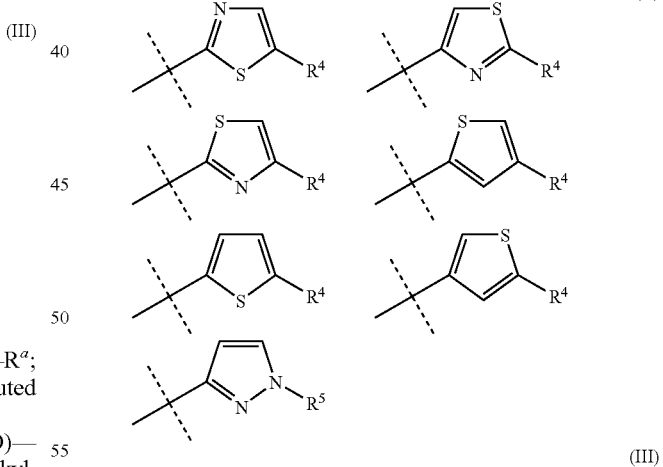

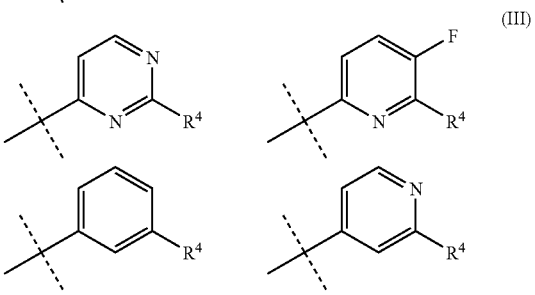

$R^2$ is H, Cl, $C_1$-$C_7$-alkyl, $C_3$-$C_6$-cycloalkyl, or —$(CH_2)_m$—$R^a$;

$R^3$ is aryl or heteroaryl each of which is optionally substituted by:
  CN, Cl, F, Br, $CF_3$, $CHF_2$, —O—$C_1$-$C_7$-alkyl, —(CO)—$R^b$, —$(CH_2)_m$—$R^c$, —NH—(CO)—$C_1$-$C_7$-alkyl, —O—$CH_2F$, —O—$CHF_2$, —O—$CF_3$, —$S(O)_2$—$R^d$, or heteroaryl which is optionally substituted by $C_1$-$C_7$-alkyl;

$R^4$ is —OH, Cl, F, Br, CN, —$CHF_2$, $CF_3$, $C_1$-$C_7$-alkyl, —$C_3$-$C_6$-cycloalkyl, —O—(CO)—$C_1$-$C_7$-alkyl, or —$(CH_2)_m$—$R^e$;

$R^5$ is $C_1$-$C_7$-alkyl, $C_1$-$C_7$-alkyl-$C_3$-$C_6$-cycloalkyl, —$(CH_2)_n$—O—$R^f$, $C_3$-$C_8$-alkenyl-O—$R^f$, —$(CH_2)_n$—$NR^gR^h$, —$C_2$-$C_6$-alkenyl-$NR^gR^h$, or —$(CH_2)_n$—$R^e$;

$R^a$ is —O—$C_1$-$C_7$-alkyl or —OH;

$R^b$ is $C_1$-$C_7$-alkyl, $NH_2$, or —O—$C_1$-$C_7$-alkyl;

$R^c$ is —OH, $NH_2$, or NH—(CO)—O—$C_1$-$C_7$-alkyl;

$R^d$ is $C_1$-$C_7$-alkyl, —$NH_2$, —NH—$C_1$-$C_7$-alkyl, or —N-di($C_1$-$C_7$-alkyl);

$R^e$ is —OH, —$CH_2F$, —$CHF_2$, —$CF_3$, —O—(CO)—$C_1$-$C_7$-alkyl, or —$C_3$-$C_6$-cycloalkyl;

$R^f$ is $C_1$-$C_7$-alkyl, $C_3$-$C_8$-alkenyl, $C_3$-$C_6$-cycloalkyl, phenyl, benzyl, or —(CO)—R';

$R^g$ and $R^h$ are each independently H, $C_1$-$C_7$-alkyl, $C_3$-$C_6$-cycloalkyl, $C_3$-$C_8$-alkenyl, phenyl, benzyl, or —(CO)—R' or $R^g$ and $R^h$, together with the nitrogen atom to which they are attached, form a 5- to 7-membered heterocyclic or heteroaryl ring optionally substituted with 1 or 2 OH;

R' is $NH_2$, —NH—$C_1$-$C_7$-alkyl, $C_1$-$C_7$-alkyl, or $C_1$-$C_7$-alkoxy;

m is 1 to 4; and n is 2 to 6;

as well as pharmaceutically acceptable salts thereof.

Also encompassed by the compounds of formula (I) are those compounds of formula (Ia):

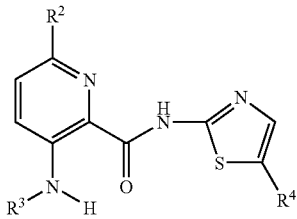

(Ia)

wherein $R^2$, $R^3$ and $R^4$ are as defined hereinabove.

In certain embodiments, the compounds of formula (Ia) according to the invention are those compounds wherein:

$R^2$ is H or $C_1$-$C_7$-alkyl;

$R^3$ is phenyl or 5- or 6-membered heteroaryl each of which is optionally substituted by:
  CN, Cl, F, Br, $CF_3$, $CHF_2$, —O—$C_1$-$C_7$-alkyl, —(CO)—$R^b$, —$(CH_2)_m$—$R^c$, —NH—(CO)—$C_1$-$C_7$-alkyl, —O—$CH_2F$, —O—$CHF_2$, —O—$CF_3$, —$S(O)_2$—$R^d$, or heteroaryl which is optionally substituted by $C_1$-$C_7$-alkyl;

$R^4$ is H, —OH, Cl, F, Br, CN, —$CHF_2$, $CF_3$, $C_1$-$C_7$-alkyl, —O—(CO)—$C_1$-$C_7$-alkyl, $C_3$-$C_6$-cycloalkyl, or —$(CH_2)_m$—$R^e$; and $R^b$, $R^c$, $R^d$ and $R^e$ are as defined hereinabove, as well as pharmaceutically acceptable salts thereof such as the following compounds:

6-Methyl-3-(pyrimidin-5-ylamino)-pyridine-2-carboxylic acid (5-methyl-thiazol-2-yl)-amide; and 6-Methyl-3-(pyridin-3-ylamino)-pyridine-2-carboxylic acid (5-methyl-thiazol-2-yl)-amide.

Further compounds encompassed by the compounds of formula (I) are those compounds of formula (Ib):

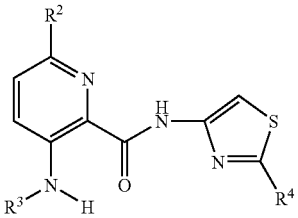

(Ib)

wherein $R^2$, $R^3$ and $R^4$ are as defined hereinabove.

In certain embodiments, the compounds of formula (Ib) according to the invention are those compounds wherein:

$R^2$ is H or $C_1$-$C_7$-alkyl;

$R^3$ is phenyl or 5- or 6-membered heteroaryl each of which is optionally substituted by:
  CN, Cl, F, Br, $CF_3$, $CHF_2$, —O—$C_1$-$C_7$-alkyl, —(CO)—$R^b$, —$(CH_2)_m$—$R^c$, —NH—(CO)—$C_1$-$C_7$-alkyl, —O—$CH_2F$, —O—$CHF_2$, —O—$CF_3$, —$S(O)_2$—$R^d$, or heteroaryl which is optionally substituted by $C_1$-$C_7$-alkyl;

$R^4$ is H, —OH, Cl, F, Br, CN, —$CHF_2$, $CF_3$, $C_1$-$C_7$-alkyl, —O—(CO)-$C_1$-$C_7$-alkyl, or —$(CH_2)_m$—$R^e$; and $R^b$, $R^c$, $R^d$ and $R^e$ are as defined hereinabove, as well as pharmaceutically acceptable salts thereof, for example the following compounds:

6-Methyl-3-(pyrimidin-5-ylamino)-pyridine-2-carboxylic acid (2-methyl-thiazol-4-yl)-amide;

6-Methyl-3-(pyridin-3-ylamino)-pyridine-2-carboxylic acid (2-methyl-thiazol-4-yl)-amide;

3-(5-Fluoro-pyridin-3-ylamino)-6-methyl-pyridine-2-carboxylic acid (2-methyl-thiazol-4-yl)-amide;

6-Methyl-3-(2-methyl-2H-pyrazol-3-ylamino)-pyridine-2-carboxylic acid (2-methyl-thiazol-4-yl)-amide;

3-(2,5-Dimethyl-2H-pyrazol-3-ylamino)-6-methyl-pyridine-2-carboxylic acid (2-methyl-thiazol-4-yl)-amide; and 6-Methyl-3-(5-methyl-pyridin-3-ylamino)-pyridine-2-carboxylic acid (2-methyl-thiazol-4-yl)-amide.

Further compounds encompassed by the compounds of formula (I) are those compounds of formula (Ic):

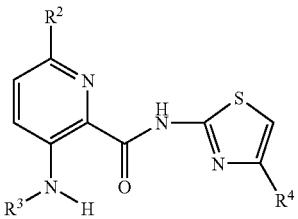

(Ic)

wherein $R^2$, $R^3$ and $R^4$ are as defined hereinabove.

In certain embodiments, the compounds of formula (Ic) according to the invention are those compounds wherein:

$R^2$ is H or $C_1$-$C_7$-alkyl;

$R^3$ is phenyl or 5- or 6-membered heteroaryl each of which is optionally substituted by:

CN, Cl, F, Br, $CF_3$, $CHF_2$, —O—$C_1$-$C_7$-alkyl, —(CO)—$R^b$, —$(CH_2)_m$—$R^c$, —NH—(CO)—$C_1$-$C_7$-alkyl, —O—$CH_2F$, —O—$CHF_2$, —O—$CF_3$, —$S(O)_2$—$R^d$, or heteroaryl which is optionally substituted by $C_1$-$C_7$-alkyl;

$R^4$ is H, —OH, Cl, F, Br, CN, —$CHF_2$, $CF_3$, $C_1$-$C_7$-alkyl, —O—(CO)—$C_1$-$C_7$-alkyl, $C_3$-$C_6$-cycloalkyl or —$(CH_2)_m$—$R^e$; and $R^b$, $R^c$, $R^d$ and $R^e$ are as defined hereinabove, as well as pharmaceutically acceptable salts thereof, for example the following compounds:

6-Methyl-3-(pyridin-3-ylamino)-pyridine-2-carboxylic acid (4-methyl-thiazol-2-yl)-amide;
6-Methyl-3-(pyrimidin-5-ylamino)-pyridine-2-carboxylic acid (4-methyl-thiazol-2-yl)-amide;
6-Methyl-3-(pyridin-3-ylamino)-pyridine-2-carboxylic acid (4-trifluoromethyl-thiazol-2-yl)-amide;
6-Methyl-3-(pyrimidin-5-ylamino)-pyridine-2-carboxylic acid (4-trifluoromethyl-thiazol-2-yl)-amide;
6-Methyl-3-(4-methyl-pyridin-3-ylamino)-pyridine-2-carboxylic acid (4-methyl-thiazol-2-yl)-amide;
3-(5-Cyano-pyridin-3-ylamino)-6-methyl-pyridine-2-carboxylic acid (4-methyl-thiazol-2-yl)-amide;
6-Methyl-3-(2-methyl-pyridin-3-ylamino)-pyridine-2-carboxylic acid (4-methyl-thiazol-2-yl)-amide;
3-(5-Fluoro-pyridin-3-ylamino)-6-methyl-pyridine-2-carboxylic acid (4-methyl-thiazol-2-yl)-amide;
3-(3-Fluoro-phenylamino)-6-methyl-pyridine-2-carboxylic acid (4-methyl-thiazol-2-yl)-amide;
3-(3,5-Difluoro-phenylamino)-6-methyl-pyridine-2-carboxylic acid (4-methyl-thiazol-2-yl)-amide;
6-Methyl-3-phenylamino-pyridine-2-carboxylic acid (4-methyl-thiazol-2-yl)-amide;
3-(3-Cyano-5-fluoro-phenylamino)-6-methyl-pyridine-2-carboxylic acid (4-methyl-thiazol-2-yl)-amide;
3-(3-Cyano-phenylamino)-6-methyl-pyridine-2-carboxylic acid (4-methyl-thiazol-2-yl)-amide;
3-(2-Chloro-pyridin-4-ylamino)-6-methyl-pyridine-2-carboxylic acid (4-methyl-thiazol-2-yl)-amide;
6-Methyl-3-(4-methyl-pyridin-3-ylamino)-pyridine-2-carboxylic acid (4-trifluoromethyl-thiazol-2-yl)-amide;
3-(5-Cyano-pyridin-3-ylamino)-6-methyl-pyridine-2-carboxylic acid (4-trifluoromethyl-thiazol-2-yl)-amide;
3-(3-Fluoro-phenylamino)-6-methyl-pyridine-2-carboxylic acid (4-trifluoromethyl-thiazol-2-yl)-amide;
3-(3-Cyano-phenylamino)-6-methyl-pyridine-2-carboxylic acid (4-trifluoromethyl-thiazol-2-yl)-amide;
3-(3,5-Difluoro-phenylamino)-6-methyl-pyridine-2-carboxylic acid (4-trifluoromethyl-thiazol-2-yl)-amide;
6-Methyl-3-(pyrimidin-5-ylamino)-pyridine-2-carboxylic acid (4-methoxymethyl-thiazol-2-yl)-amide;
3-(3,5-Difluoro-phenylamino)-6-methyl-pyridine-2-carboxylic acid (4-methoxymethyl-thiazol-2-yl)-amide;
3-(5-Fluoro-pyridin-3-ylamino)-6-methyl-pyridine-2-carboxylic acid (4-methoxymethyl-thiazol-2-yl)-amide;
6-Methyl-3-(pyrimidin-5-ylamino)-pyridine-2-carboxylic acid (4-cyclopropyl-thiazol-2-yl)-amide;
3-(5-Fluoro-pyridin-3-ylamino)-6-methyl-pyridine-2-carboxylic acid (4-cyclopropyl-thiazol-2-yl)-amide;
6-Methyl-3-(pyridin-3-ylamino)-pyridine-2-carboxylic acid (4-cyclopropyl-thiazol-2-yl)-amide;
3-(3,5-Difluoro-phenylamino)-6-methyl-pyridine-2-carboxylic acid (4-cyclopropyl-thiazol-2-yl)-amide;
6-Methyl-3-(2-methyl-2H-pyrazol-3-ylamino)-pyridine-2-carboxylic acid (4-methyl-thiazol-2-yl)-amide;
6-Methyl-3-(1-methyl-1H-pyrazol-4-ylamino)-pyridine-2-carboxylic acid (4-methyl-thiazol-2-yl)-amide;
3-(2,5-Dimethyl-2H-pyrazol-3-ylamino)-6-methyl-pyridine-2-carboxylic acid (4-methyl-thiazol-2-yl)-amide;
6-Methyl-3-(5-methyl-pyridin-3-ylamino)-pyridine-2-carboxylic acid (4-methyl-thiazol-2-yl)-amide;
3-(5-Cyclopropyl-2-methyl-2H-pyrazol-3-ylamino)-6-methyl-pyridine-2-carboxylic acid (4-methyl-thiazol-2-yl)-amide;
6-Methyl-3-(pyrimidin-5-ylamino)-pyridine-2-carboxylic acid (4-methyl-thiazol-2-yl)-amide;
6-Methyl-3-(pyrimidin-5-ylamino)-pyridine-2-carboxylic acid (4-hydroxymethyl-thiazol-2-yl)-amide;
6-Hydroxymethyl-3-(pyrimidin-5-ylamino)-pyridine-2-carboxylic acid (4-methyl-thiazol-2-yl)-amide;
6-Cyclopropyl-3-(pyridin-3-ylamino)-pyridine-2-carboxylic acid (4-methyl-thiazol-2-yl)-amide; and
6-Ethyl-3-(pyrimidin-5-ylamino)-pyridine-2-carboxylic acid (4-methyl-thiazol-2-yl)-amide.

Further compounds encompassed by the compounds of formula (I) are those compounds of formula (Id):

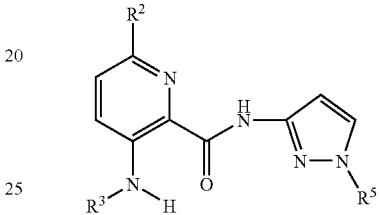

(Id)

wherein $R^2$, $R^3$ and $R^5$ are as defined hereinabove.

In certain embodiments, the compounds of formula (Id) according to the invention are those compounds wherein:

$R^2$ is H or $C_1$-$C_7$-alkyl;

$R^3$ is phenyl or 5- or 6-membered heteroaryl each of which is optionally substituted by:
CN, Cl, F, Br, $CF_3$, $CHF_2$, —O—$C_1$-$C_7$-alkyl, —(CO)—$R^b$, —$(CH_2)_m$—$R^c$, —NH—(CO)-$C_1$-$C_7$-alkyl, —O—$CH_2F$, —O—$CHF_2$, —O—$CF_3$, —$S(O)_2$—$R^d$, or heteroaryl which is optionally substituted by $C_1$-$C_7$-alkyl;

$R^5$ is $C_1$-$C_7$-alkyl, $C_1$-$C_7$-alkyl-$C_3$-$C_6$-cycloalkyl, —$(CH_2)_n$—O—$R^f$, $C_3$-$C_8$-alkenyl-O—$R^f$, —$(CH_2)_n$—$NR^gR^h$, —$C_2$-$C_6$-alkenyl-$NR^gR^h$, or —$(CH_2)_n$—$R^e$; and $R^b$, $R^c$, $R^d$, $R^e$, $R^f$, $R^g$ and $R^h$ are as defined hereinabove, as well as pharmaceutically acceptable salts thereof such as the following compounds:

6-Methyl-3-(pyridin-3-ylamino)-pyridine-2-carboxylic acid (1-methyl-1H-pyrazol-3-yl)-amide;
6-Methyl-3-(pyrimidin-5-ylamino)-pyridine-2-carboxylic acid (1-methyl-1H-pyrazol-3-yl)-amide;
3-(5-Cyano-pyridin-3-ylamino)-6-methyl-pyridine-2-carboxylic acid (1-methyl-1H-pyrazol-3-yl)-amide;
6-Methyl-3-(4-methyl-pyridin-3-ylamino)-pyridine-2-carboxylic acid (1-methyl-1H-pyrazol-3-yl)-amide;
6-Methyl-3-(2-methyl-pyridin-3-ylamino)-pyridine-2-carboxylic acid (1-methyl-1H-pyrazol-3-yl)-amide;
3-(5-Fluoro-pyridin-3-ylamino)-6-methyl-pyridine-2-carboxylic acid (1-methyl-1H-pyrazol-3-yl)-amide;
3-(3,5-Difluoro-phenylamino)-6-methyl-pyridine-2-carboxylic acid (1-methyl-1H-pyrazol-3-yl)-amide;
3-(3-Cyano-phenylamino)-6-methyl-pyridine-2-carboxylic acid (1-methyl-1H-pyrazol-3-yl)-amide;
3-(3-Fluoro-phenylamino)-6-methyl-pyridine-2-carboxylic acid (1-methyl-1H-pyrazol-3-yl)-amide;
3-(3-Cyano-5-fluoro-phenylamino)-6-methyl-pyridine-2-carboxylic acid (1-methyl-1H-pyrazol-3-yl)-amide;
6-Methyl-3-phenylamino-pyridine-2-carboxylic acid (1-methyl-1H-pyrazol-3-yl)-amide;
3-(2-Chloro-pyridin-4-ylamino)-6-methyl-pyridine-2-carboxylic acid (1-methyl-1H-pyrazol-3-yl)-amide;

6-Methyl-3-(5-trifluoromethyl-pyridin-3-ylamino)-pyridine-2-carboxylic acid (1-methyl-1H-pyrazol-3-yl)-amide;
3-(3,5-Difluoro-phenylamino)-6-methyl-pyridine-2-carboxylic acid [1-(2-methoxy-ethyl)-1H-pyrazol-3-yl]-amide;
3-(5-Fluoro-pyridin-3-ylamino)-6-methyl-pyridine-2-carboxylic acid [1-(2-methoxy-ethyl)-1H-pyrazol-3-yl]-amide;
6-Methyl-3-(pyrimidin-5-ylamino)-pyridine-2-carboxylic acid [1-(2-methoxy-ethyl)-1H-pyrazol-3-yl]-amide;
3-(3-Cyano-phenylamino)-6-methyl-pyridine-2-carboxylic acid [1-(2-methoxy-ethyl)-1H-pyrazol-3-yl]-amide;
3-(4-Fluoro-pyridin-2-ylamino)-6-methyl-pyridine-2-carboxylic acid [1-(2-methoxy-ethyl)-1H-pyrazol-3-yl]-amide;
3-(3-Fluoro-phenylamino)-6-methyl-pyridine-2-carboxylic acid [1-(2-methoxy-ethyl)-1H-pyrazol-3-yl]-amide;
3-(3-Cyano-5-fluoro-phenylamino)-6-methyl-pyridine-2-carboxylic acid [1-(2-methoxy-ethyl)-1H-pyrazol-3-yl]-amide;
6-Methyl-3-(1-methyl-1H-pyrazol-3-ylamino)-pyridine-2-carboxylic acid (1-methyl-1H-pyrazol-3-yl)-amide;
3-(4-Fluoro-phenylamino)-6-methyl-pyridine-2-carboxylic acid (1-methyl-1H-pyrazol-3-yl)-amide;
6-Methyl-3-(4-methyl-thiazol-2-ylamino)-pyridine-2-carboxylic acid (1-methyl-1H-pyrazol-3-yl)-amide;
6-Methyl-3-(pyrazin-2-ylamino)-pyridine-2-carboxylic acid (1-methyl-1H-pyrazol-3-yl)-amide;
6-Methyl-3-(2-methyl-2H-pyrazol-3-ylamino)-pyridine-2-carboxylic acid (1-methyl-1H-pyrazol-3-yl)-amide;
6-Methyl-3-(1-methyl-1H-pyrazol-4-ylamino)-pyridine-2-carboxylic acid (1-methyl-1H-pyrazol-3-yl)-amide;
3-(2,5-Dimethyl-2H-pyrazol-3-ylamino)-6-methyl-pyridine-2-carboxylic acid (1-methyl-1H-pyrazol-3-yl)-amide;
6-Methyl-3-(6-methyl-pyrazin-2-ylamino)-pyridine-2-carboxylic acid (1-methyl-1H-pyrazol-3-yl)-amide;
6-Methyl-3-(4-methyl-pyrimidin-5-ylamino)-pyridine-2-carboxylic acid (1-methyl-1H-pyrazol-3-yl)-amide;
3-(5-Fluoro-6-methyl-pyridin-2-ylamino)-6-methyl-pyridine-2-carboxylic acid (1-methyl-1H-pyrazol-3-yl)-amide;
3-(5-Chloro-pyridin-3-ylamino)-6-methyl-pyridine-2-carboxylic acid (1-methyl-1H-pyrazol-3-yl)-amide;
6-Methyl-3-(5-methyl-pyridin-3-ylamino)-pyridine-2-carboxylic acid (1-methyl-1H-pyrazol-3-yl)-amide;
3-(5-Cyclopropyl-2-methyl-2H-pyrazol-3-ylamino)-6-methyl-pyridine-2-carboxylic acid (1-methyl-1H-pyrazol-3-yl)-amide;
6-Cyclopropyl-3-(pyrimidin-5-ylamino)-pyridine-2-carboxylic acid (1-methyl-1H-pyrazol-3-yl)-amide; and
6-Cyclopropyl-3-(pyridin-3-ylamino)-pyridine-2-carboxylic acid (1-methyl-1H-pyrazol-3-yl)-amide.

Further compounds encompassed by the compounds of formula (I) are those compounds of formula (Ie):

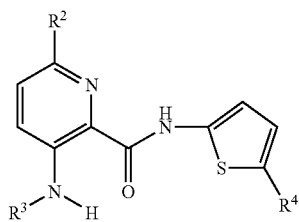

(Ie)

wherein $R^2$, $R^3$ and $R^4$ are as defined hereinabove.

In certain embodiments, the compounds of formula (Ie) according to the invention are those compounds wherein:
$R^2$ is H or $C_1$-$C_7$-alkyl;
$R^3$ is phenyl or 5- or 6-membered heteroaryl each of which is optionally substituted by:
CN, Cl, F, Br, $CF_3$, $CHF_2$, —O—$C_1$-$C_7$-alkyl, —(CO)—$R^b$, —$(CH_2)_m$—$R^c$, —NH—(CO)—$C_1$-$C_7$-alkyl, —O—$CH_2F$, —O—$CHF_2$, —O—$CF_3$, —$S(O)_2$—$R^d$, or heteroaryl which is optionally substituted by $C_1$-$C_7$-alkyl;
$R^4$ is H, —OH, Cl, F, Br, CN, —$CHF_2$, $CF_3$, $C_1$-$C_7$-alkyl, —O—(CO)—$C_1$-$C_7$-alkyl, or —$(CH_2)_m$—$R^e$; and
$R^b$, $R^c$, $R^d$ and $R^e$ are as defined hereinabove, as well as pharmaceutically acceptable salts thereof.

Further compounds encompassed by the compounds of formula (I) are those compounds of formula (If):

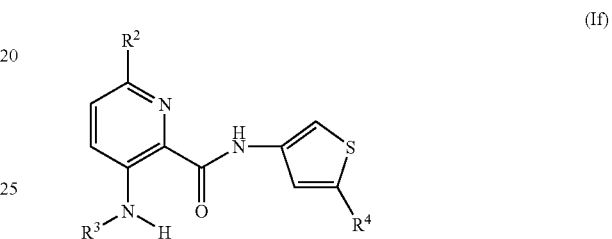

(If)

wherein $R^2$, $R^3$ and $R^4$ are as defined hereinabove.

In certain embodiments, the compounds of formula (If) according to the invention are those compounds wherein:
$R^2$ is H or $C_1$-$C_7$-alkyl;
$R^3$ is phenyl or 5- or 6-membered heteroaryl each of which is optionally substituted by:
CN, Cl, F, Br, $CF_3$, $CHF_2$, —O—$C_1$-$C_7$-alkyl, —(CO)—$R^b$, —$(CH_2)_m$—$R^c$, —NH—(CO)—$C_1$-$C_7$-alkyl, —O—$CH_2F$, —O—$CHF_2$, —O—$CF_3$, —$S(O)_2$—$R^d$, or heteroaryl which is optionally substituted by $C_1$-$C_7$-alkyl;
$R^4$ is H, —OH, Cl, F, Br, CN, —$CHF_2$, $CF_3$, $C_1$-$C_7$-alkyl, —O—(CO)—$C_1$-$C_7$-alkyl, or —$(CH_2)_m$—$R^e$; and
$R^b$, $R^c$, $R^d$ and $R^e$ are as defined hereinabove, as well as pharmaceutically acceptable salts thereof.

Further compounds encompassed by the compounds of formula (I) are those compounds of formula (Ig):

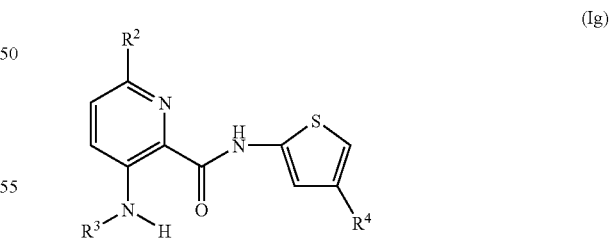

(Ig)

wherein $R^2$, $R^3$ and $R^4$ are as defined hereinabove.

In certain embodiments, the compounds of formula (Ig) according to the invention are those compounds wherein:
$R^2$ is H or $C_1$-$C_7$-alkyl;
$R^3$ is phenyl or 5- or 6-membered heteroaryl each of which is optionally substituted by:
CN, Cl, F, Br, $CF_3$, $CHF_2$, —O—$C_1$-$C_7$-alkyl, —(CO)—$R^b$, —$(CH_2)_m$—$R^c$, —NH—(CO)—$C_1$-$C_7$-alkyl, —O—CH₂F, —O—CHF₂, —O—CF₃, —S(O)₂—$R^d$, or heteroaryl which is optionally substituted by $C_1$-$C_7$-alkyl;

$R^4$ is H, —OH, Cl, F, Br, CN, —CHF₂, CF₃, $C_1$-$C_7$-alkyl, —O—(CO)—$C_1$-$C_7$-alkyl, or —(CH₂)$_m$—$R^e$; and $R^b$, $R^c$, $R^d$ and $R^e$ are as defined hereinabove, as well as pharmaceutically acceptable salts thereof.

Further compounds encompassed by the compounds of formula (I) are those compounds of formula (Ih):

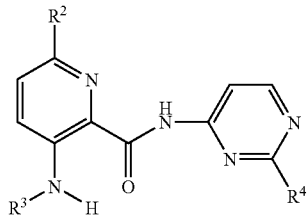

(Ih)

wherein $R^2$, $R^3$ and $R^4$ are as defined hereinabove.

In certain embodiments, the compounds of formula (Ih) according to the invention are those compounds wherein:

$R^2$ is H or $C_1$-$C_7$-alkyl;

$R^3$ is phenyl or 5- or 6-membered heteroaryl each of which is optionally substituted by:

CN, Cl, F, Br, CF₃, CHF₂, —O—$C_1$-$C_7$-alkyl, —(CO)—$R^b$, —(CH₂)$_m$—$R^c$, —NH—(CO)—$C_1$-$C_7$-alkyl, —O—CH₂F, —O—CHF₂, —O—CF₃, —S(O)₂—$R^d$, or heteroaryl which is optionally substituted by $C_1$-$C_7$-alkyl;

$R^4$ is H, —H, Cl, F, Br, CN, —CHF₂, CF₃, $C_1$-$C_7$-alkyl, —O—(CO)—$C_1$-$C_7$-alkyl, or —(CH₂)$_m$—$R^e$; and $R^b$, $R^c$, $R^d$ and $R^e$ are as defined hereinabove, as well as pharmaceutically acceptable salts thereof.

Further compounds encompassed by the compounds of formula (I) are those compounds of formula (Ii):

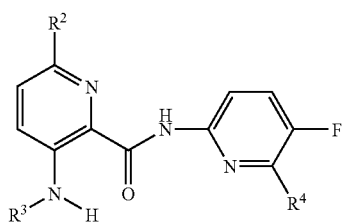

(Ii)

wherein $R^2$, $R^3$ and $R^4$ are as defined hereinabove. In this embodiment, $R^4$ can also be H.

In certain embodiments, the compounds of formula (Ii) according to the invention are those compounds wherein:

$R^2$ is H or $C_1$-$C_7$-alkyl;

$R^3$ is phenyl or 5- or 6-membered heteroaryl each of which is optionally substituted by:

CN, Cl, F, Br, CF₃, CHF₂, —O—$C_1$-$C_7$-alkyl, —(CO)—$R^b$, —(CH₂)$_m$—$R^c$, —NH—(CO)—$C_1$-$C_7$-alkyl, —O—CH₂F, —O—CHF₂, —O—CF₃, —S(O)₂—$R^d$, or heteroaryl which is optionally substituted by $C_1$-$C_7$-alkyl;

$R^4$ is H, —OH, Cl, F, Br, CN, —CHF₂, CF₃, $C_1$-$C_7$-alkyl, —O—(CO)—$C_1$-$C_7$-alkyl, or —(CH₂)$_m$—$R^e$; and $R^b$, $R^c$, $R^d$ and $R^e$ are as defined hereinabove, as well as pharmaceutically acceptable salts thereof, for example the following compounds:

6-Methyl-3-(pyridin-3-ylamino)-pyridine-2-carboxylic acid (5-fluoro-pyridin-2-yl)-amide;

6-Methyl-3-(pyrimidin-5-ylamino)-pyridine-2-carboxylic acid (5-fluoro-pyridin-2-yl)-amide;

3-(5-Fluoro-pyridin-3-ylamino)-6-methyl-pyridine-2-carboxylic acid (5-fluoro-pyridin-2-yl)-amide;

6-Methyl-3-(pyridin-3-ylamino)-pyridine-2-carboxylic acid (5-fluoro-6-methyl-pyridin-2-yl)-amide;

6-Methyl-3-(pyrimidin-5-ylamino)-pyridine-2-carboxylic acid (5-fluoro-6-methyl-pyridin-2-yl)-amide;

3-(5-Fluoro-pyridin-3-ylamino)-6-methyl-pyridine-2-carboxylic acid (5-fluoro-6-methyl-pyridin-2-yl)-amide;

6-Methyl-3-(4-methyl-pyridin-3-ylamino)-pyridine-2-carboxylic acid (5-fluoro-pyridin-2-yl)-amide:

6-Methyl-3-(2-methyl-pyridin-3-ylamino)-pyridine-2-carboxylic acid (5-fluoro-pyridin-2-yl)-amide:

3-(3-Fluoro-phenylamino)-6-methyl-pyridine-2-carboxylic acid (5-fluoro-pyridin-2-yl)-amide:

3-(3-Cyano-phenylamino)-6-methyl-pyridine-2-carboxylic acid (5-fluoro-pyridin-2-yl)-amide:

3-(3,5-Difluoro-phenylamino)-6-methyl-pyridine-2-carboxylic acid (5-fluoro-pyridin-2-yl)-amide:

6-Methyl-3-(4-methyl-pyridin-3-ylamino)-pyridine-2-carboxylic acid (5-fluoro-6-methyl-pyridin-2-yl)-amide;

6-Methyl-3-(2-methyl-pyridin-3-ylamino)-pyridine-2-carboxylic acid (5-fluoro-6-methyl-pyridin-2-yl)-amide;

3-(3-Fluoro-phenylamino)-6-methyl-pyridine-2-carboxylic acid (5-fluoro-6-methyl-pyridin-2-yl)-amide;

3-(3,5-Difluoro-phenylamino)-6-methyl-pyridine-2-carboxylic acid (5-fluoro-6-methyl-pyridin-2-yl)-amide;

3-(3-Cyano-phenylamino)-6-methyl-pyridine-2-carboxylic acid (5-fluoro-6-methyl-pyridin-2-yl)-amide;

6-Methyl-3-(2-methyl-2H-pyrazol-3-ylamino)-pyridine-2-carboxylic acid (5-fluoro-pyridin-2-yl)-amide;

6-Methyl-3-(1-methyl-1H-pyrazol-4-ylamino)-pyridine-2-carboxylic acid (5-fluoro-pyridin-2-yl)-amide;

6-Methyl-3-(1-methyl-1H-pyrazol-4-ylamino)-pyridine-2-carboxylic acid (5-fluoro-pyridin-2-yl)-amide;

3-(5-Cyclopropyl-2-methyl-2H-pyrazol-3-ylamino)-6-methyl-pyridine-2-carboxylic acid (5-fluoro-6-methyl-pyridin-2-yl)-amide; and 3-(5-Cyclopropyl-2-methyl-2H-pyrazol-3-ylamino)-6-methyl-pyridine-2-carboxylic acid (5-fluoro-pyridin-2-yl)-amide.

Still further compounds encompassed by the compounds of formula (I) are those compounds of formula (Ij):

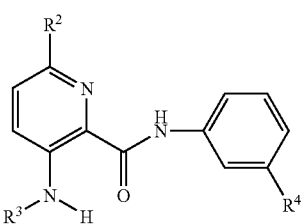

(Ij)

wherein $R^2$, $R^3$ and $R^4$ are as defined hereinabove.

In certain embodiments, the compounds of formula (Ij) according to the invention are those compounds wherein:

$R^2$ is H or $C_1$-$C_7$-alkyl;

$R^3$ is phenyl or 5- or 6-membered heteroaryl each of which is optionally substituted by:

CN, Cl, F, Br, CF₃, CHF₂, —O—$C_1$-$C_7$-alkyl, —(CO)—$R^b$, —(CH₂)$_m$—$R^c$, —NH—(CO)—$C_1$-$C_7$-alkyl, —O—CH₂F, —O—CHF₂, —O—CF₃, —S(O)₂—$R^d$, or heteroaryl which is optionally substituted by $C_1$-$C_7$-alkyl;

$R^4$ is H, —OH, Cl, F, Br, CN, —CHF₂, CF₃, $C_1$-$C_7$-alkyl, —O—(CO)—$C_1$-$C_7$-alkyl, or —(CH₂)$_m$—$R^e$; and $R^b$, $R^c$, $R^d$ and $R^e$ are as defined hereinabove, as well as pharmaceutically acceptable salts thereof, for example the following compounds:

6-Methyl-3-(pyridin-3-ylamino)-pyridine-2-carboxylic acid (3-chloro-phenyl)-amide;
6-Methyl-3-(pyrimidin-5-ylamino)-pyridine-2-carboxylic acid (3-chloro-phenyl)-amide; and
3-(5-Chloro-pyridin-3-ylamino)-6-methyl-pyridine-2-carboxylic acid (3-chloro-phenyl)amide.

Still further compounds encompassed by the compounds of formula (I) are those compounds of formula (Ik):

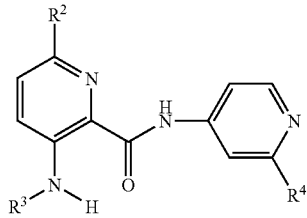

(Ik)

wherein $R^2$, $R^3$ and $R^4$ are as defined hereinabove.

In certain embodiments, the compounds of formula (Ik) according to the invention are those compounds wherein:
$R^2$ is H or $C_1$-$C_7$-alkyl;
$R^3$ is phenyl or 5- or 6-membered heteroaryl each of which is optionally substituted by:
   CN, Cl, F, Br, $CF_3$, $CHF_2$, —O—$C_1$-$C_7$-alkyl, —(CO)—$R^b$, —$(CH_2)_m$—$R^c$, —NH—(CO)—$C_1$-$C_7$-alkyl, —O—$CH_2$F, —O—$CHF_2$, —O—$CF_3$, —$S(O)_2$—$R^d$, or heteroaryl which is optionally substituted by $C_1$-$C_7$-alkyl;
$R^4$ is H, —OH, Cl, F, Br, CN, —$CHF_2$, $CF_3$, $C_1$-$C_7$-alkyl, —O—(CO)—$C_1$-$C_7$-alkyl, or —$(CH_2)_m$—$R^e$; and
$R^b$, $R^c$, $R^d$ and $R^e$ are as defined hereinabove, as well as pharmaceutically acceptable salts thereof, for example the following compounds:
6-Methyl-3-(pyridin-3-ylamino)-pyridine-2-carboxylic acid (2-chloro-pyridin-4-yl)-amide;
6-Methyl-3-(pyridin-3-ylamino)-pyridine-2-carboxylic acid (2-methyl-pyridin-4-yl)-amide;
6-Methyl-3-(pyrimidin-5-ylamino)-pyridine-2-carboxylic acid (2-methyl-pyridin-4-yl)-amide;
3-(5-Fluoro-pyridin-3-ylamino)-6-methyl-pyridine-2-carboxylic acid (2-methyl-pyridin-4-yl)-amide;
6-Methyl-3-(4-methyl-pyridin-3-ylamino)-pyridine-2-carboxylic acid (2-methyl-pyridin-4-yl)-amide;
6-Methyl-3-(2-methyl-pyridin-3-ylamino)-pyridine-2-carboxylic acid (2-methyl-pyridin-4-yl)-amide;
3-(5-Cyano-pyridin-3-ylamino)-6-methyl-pyridine-2-carboxylic acid (2-methyl-pyridin-4-yl)-amide;
3-(3-Fluoro-phenylamino)-6-methyl-pyridine-2-carboxylic acid (2-methyl-pyridin-4-yl)-amide;
3-(3-Cyano-phenylamino)-6-methyl-pyridine-2-carboxylic acid (2-methyl-pyridin-4-yl)-amide; and
3-(3,5-Difluoro-phenylamino)-6-methyl-pyridine-2-carboxylic acid (2-methyl-pyridin-4-yl)-amide.

In certain embodiments, the compounds of formula (I) are those wherein:
$R^3$ is aryl optionally substituted by CN, Cl, F, Br, $CF_3$, $CHF_2$, —O—$C_1$-$C_7$-alkyl, —(CO)—$R^b$, —$(CH_2)_m$—$R^c$, —NH—(CO)—$C_1$-$C_7$-alkyl, —O—$CH_2$F, —O—$CHF_2$, —O—$CF_3$, —$S(O)_2$—$R^d$, —$C_3$-$C_6$-cycloalkyl, or heteroaryl which is optionally substituted by $C_1$-$C^7$-alkyl. In particular, compounds of formula (I) are those wherein:
$R^3$ is phenyl optionally substituted by CN, Cl, F, Br, $CF_3$, —O—$C_1$-$C_7$-alkyl, —(CO)—$R^b$, —$(CH_2)_m$—$R^c$, —NH—(CO)—$C_1$-$C_7$-alkyl, —O—$CH_2$F, —O—$CHF_2$, —O—$CF_3$, —$S(O)_2$—$R^d$ or heteroaryl which is optionally substituted by $C_1$-$C_7$-alkyl.

In certain other embodiments, the compounds of formula (I) are those wherein:
$R^3$ is heteroaryl optionally substituted by CN, Cl, F, Br, $CF_3$, $CHF_2$, —O—$C_1$-$C_7$-alkyl, —(CO)—$R^b$, —$(CH_2)_m$—$R^c$, —NH—(CO)—$C_1$-$C_7$-alkyl, —O—$CH_2$F, —O—$CHF_2$, —O—$CF_3$, —$S(O)_2$—$R^d$, —$C_3$-$C_6$-cycloalkyl, or heteroaryl which is optionally substituted by $C^1$-$C^7$-alkyl. In particular, compounds of formula (I) are those wherein:
$R^3$ is a 5- or 6- membered heteroaryl which is optionally substituted by CN, Cl, F, Br, $CF_3$, $CHF_2$, —O—$C_1$-$C_7$-alkyl, —(CO)—$R^b$, —$(CH_2)_m$—$R^c$, —NH—(CO)—$C_1$-$C_7$-alkyl, —O—$CH_2$F, —O—$CHF_2$, —O—$CF_3$, —$S(O)_2$—$R^d$, or heteroaryl which is optionally substituted by $C_1$-$C^7$-alkyl.

In certain embodiments, the compounds of formula (I) are those in which $R^f$ is $C_1$-$C_7$-alkyl, $C_3$-$C_8$-alkenyl, $C_3$-$C_6$-cycloalkyl, or —(CO)—R'. In other embodiments, compounds of formula (I) are those in which $R^f$ is phenyl or benzyl.

In certain embodiments, the compounds of formula (I) are those wherein at least one of $R^g$ and $R^h$ is H, —$C_1$-$C_7$-alkyl, $C_3$-$C_6$-cycloalkyl, $C_3$-$C_8$-alkenyl, or —(CO)—R'. In other embodiments, the compounds of formula (I) are those wherein at least one of $R^g$ and $R^h$ is phenyl or benzyl. In other embodiments, the compounds of formula (I) are those wherein $R^g$ and $R^h$, together with the nitrogen atom to which they are attached, form a 5- to 7-membered heterocyclic ring optionally substituted with 1 or 2 OH. In other embodiments, the compounds of formula (I) are those wherein $R^g$ and $R^h$, together with the nitrogen atom to which they are attached, form a 5- to 7-membered heteroaryl ring optionally substituted with 1 or 2 OH.

The invention also encompasses methods for the preparation of the compounds of the invention.

The compounds of formula (I) can be prepared according to the following method of the invention which method comprises the steps of:
a) reacting an amino protected compound of formula (V):

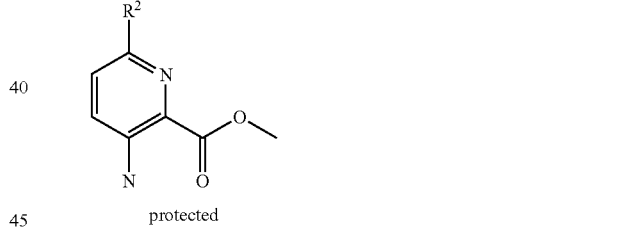

(V)

protected with a compound of formula (VI):

$R^1$—$NH_2$        (VI)

and then deprotecting the resulting compound in order to obtain a compound of formula (VIII):

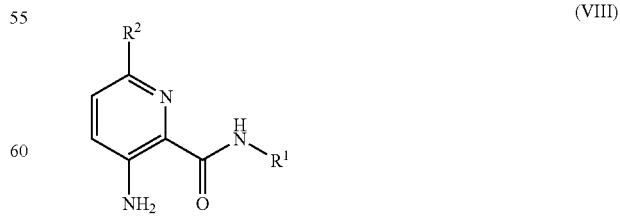

(VIII)

b) reacting the compound of formula (VIII) with a compound of formula (IX):

$R^3$—X        (IX)

in order to obtain the compound of formula (I) wherein $R^1$, $R^2$ and $R^3$ are as defined hereinabove, X is halo and N protected means that the nitrogen atom is protected by any suitable conventional protection group. N protected group can, for example, be NHBoc or $N(Boc)_2$. BOC means tert-butyloxy-carbonyl.

This method is further described in detail in scheme I and general procedure I hereafter. The compounds of formula (Ij) can be prepared according to the following method of the invention which method comprises the steps of reacting a compound of formula (XIII):

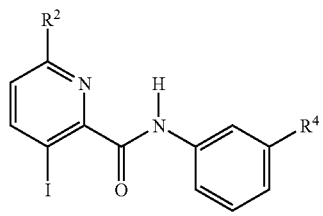
(XIII)

with a compound of formula (XIV):

$R^3$—$NH_2$ (XIV)

in order to obtain a compound of formula (Ij) wherein $R^2$, $R^3$) $R^4$ are as defined hereinabove.

The compounds of formula (I) can also be prepared according to the following method of the invention which method comprises the steps of reacting a compound of formula (XIII):

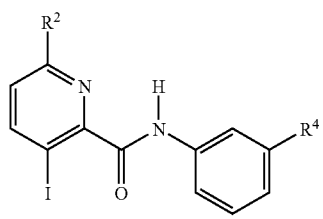
(XIII)

a) by using concentrated aqueous mineral acid in order to obtain the corresponding carboxylic acid which is then esterified to yield a compound of formula (XV):

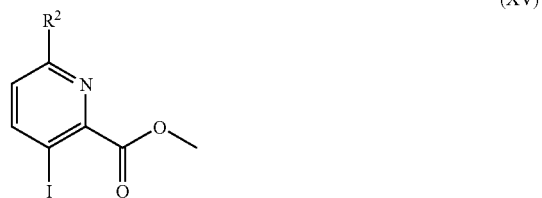
(XV)

b) reacting the compound of formula (XV) with a compound of formula (VI):

$R^1$—$NH_2$ (VI)

to obtain a compound of formula (XVI):

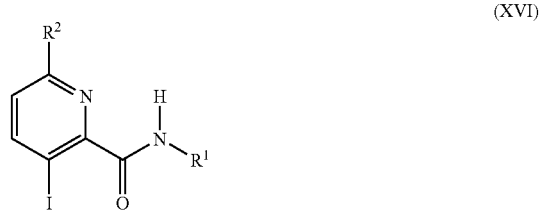
(XVI)

c) reacting the compound of formula (XVI) with a compound of formula (XIV):

$R^3$—$NH_2$ (XIV)

to obtain the compound of formula (I) wherein $R^1$, $R^2$ and $R^3$ are as defined hereinabove.

In certain embodiments of the invention, the mineral acid is HCl.

These methods are further described in details in scheme II and general procedure II hereafter.

Scheme 1:

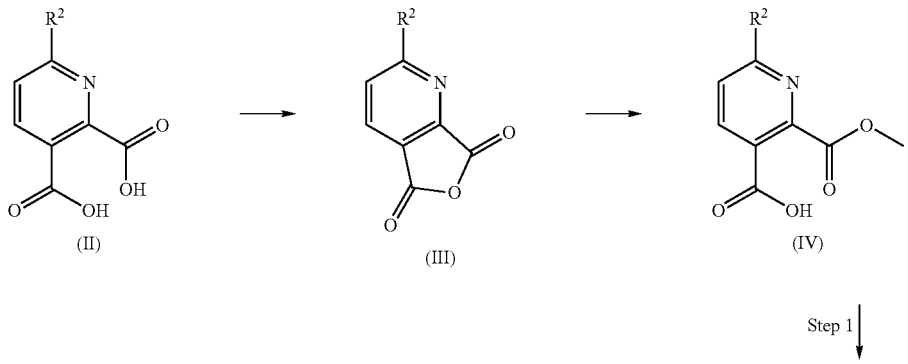

Step 1

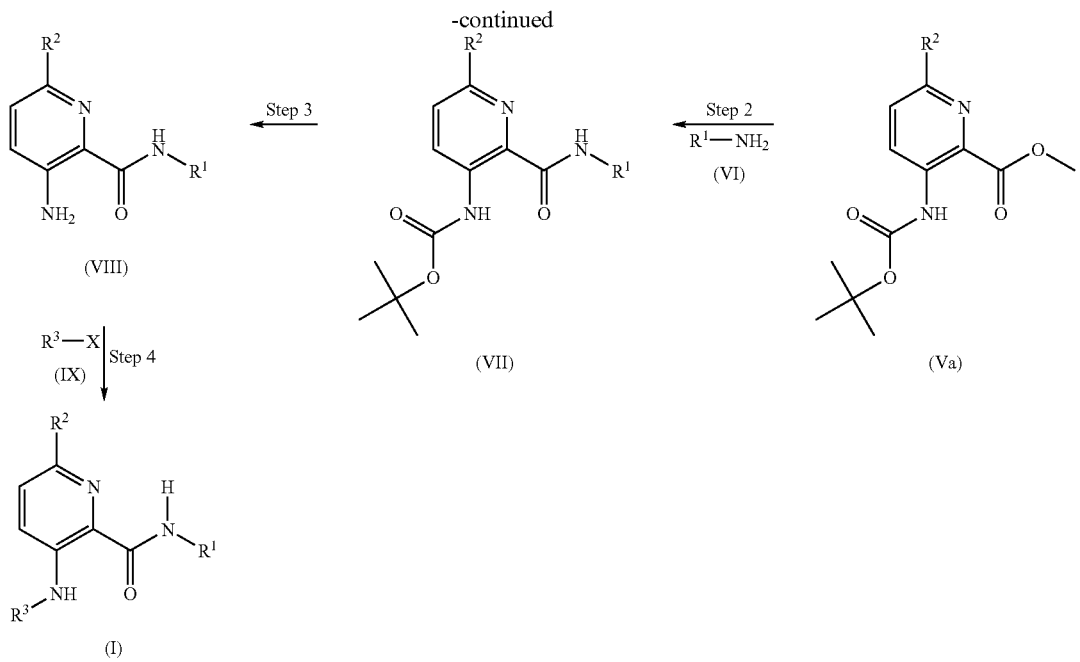

General Procedure I:

Step 1

To a solution of compound (IV) (CAS:[135338-27-1]) which can be prepared starting from commercially available compounds of formula (II) using e.g. Ac$_2$O and MeOH, N-methylmorpholine in a solvent (e.g. methylene chloride) is added diphenylphosphoryl-azide. Then tert-Butanol and a catalyst, e.g. copper(I) chloride are added, and the mixture is heated. The compound of formula (V) can be isolated and purified using conventional methods.

Step 2

To a solution of a commercially available compound of formula (VI) in a solvent (e.g. dry dioxane) a solution of trimethyl aluminium in hexane is added. A compound of formula (V) is then added. The compound of formula (VII) can be isolated and purified using conventional methods.

Step 3

The compound of formula (VIII) can be obtained by stirring an acidic solution of a compound of formula (VII) in a suitable solvent (e.g. methanol). The compound of formula (VIII) can be isolated and purified using conventional methods.

Step 4

The compound of formula (I) can be obtained by a catalyzed coupling of the compound of formula (VIII) with a commercially available compound of formula (IX), using e.g. Cesium carbonate, 4,5-bis(diphenylphosphino)-9,9-dimethylxanthene (Xanthphos) and tri(dibenzylidene-acetone)dipalladium chloroform complex (Pd$_2$(dba)$_3$·CHCl$_3$). The compound of formula (I) can then be isolated and purified using conventional methods. In certain cases where X is a chlorine or a fluorine atom and R$^3$ is a heterocyclic residue, it is also possible to conduct the coupling step in absence of a Palladium catalyst using Cesium carbonate in DMF. The compound of formula (I) can then be isolated and purified using conventional methods.

Scheme II:

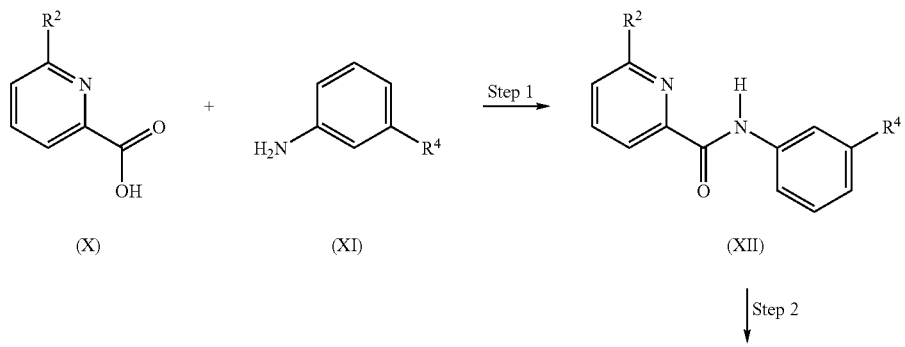

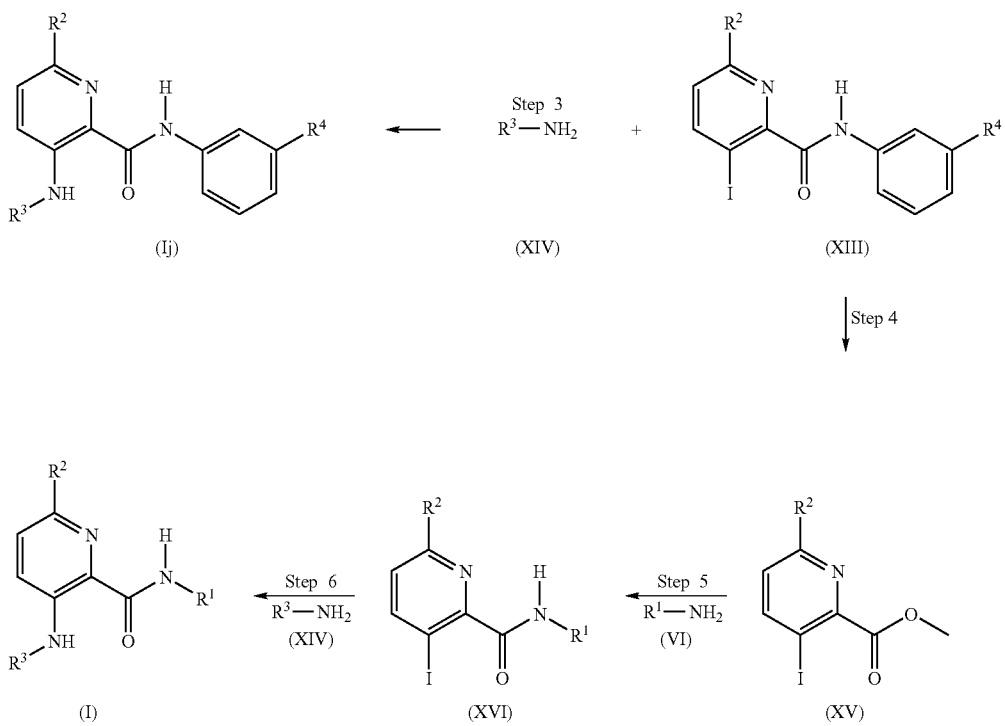

General Procedure II

Step 1:

The compound of formula (XII) can be obtained by reacting a commercially available compound of formula (X) with a compound of formula (XI) using, for example, oxalyl chloride and triethylamine. The compound of formula (XII) can then be isolated and purified using conventional methods.

Step 2:

The compound of formula (XIII) can be obtained by iodating the compound of formula (XII), using, e.g., n-BuLi and iodine as described by Epsztajn & al. [Synth. Commun. 27(6), 1075 (1997)]. The compound of formula (XIII) can then be isolated and purified using conventional methods.

Step 3:

The compound of formula (Ij) wherein Y is CH can be obtained by a catalyzed coupling with a compound of formula (XIV), using, e.g., Cesium carbonate, Xanthphos and $Pd_2(dba)_3 \cdot CHCl_3$. The compound of formula (Ij) can then be isolated and purified using conventional methods.

Step 4:

The compound of formula (XV) can be obtained by hydrolyzing the amide to the corresponding carboxylic acid using concentrated mineral acid, for example, by refluxing in 25% HCl overnight followed by conversion of the crude acid to its salt using sodium hydroxyde and esterification using methyl iodide as described by Epsztajn & al. [Synth. Commun. 27(6), 1075 (1997)]. The compound of formula (XV) can then be isolated and purified using conventional methods.

Step 5:

The compound of formula (XVI) can be obtained by reacting an amine of formula $R^1$—$NH_2$ (VI) with trimethylaluminium, followed by treatment with compound (XV). It is also possible to react the crude acid described in step 4 directly with an amine of formula $R^1$—$NH_2$ (VI) in the presence of a coupling reagent, or to convert the acid to its acid chloride and then react it with the amine in the presence of base as described in step 1. The compound of formula (XVI) can then be isolated and purified using conventional methods.

Step 6:

The compound of formula (I) can be obtained by Palladium catalyzed amination using the same methods as described for step 3. The compound of formula (I) can then be isolated and purified using conventional methods.

Scheme III:

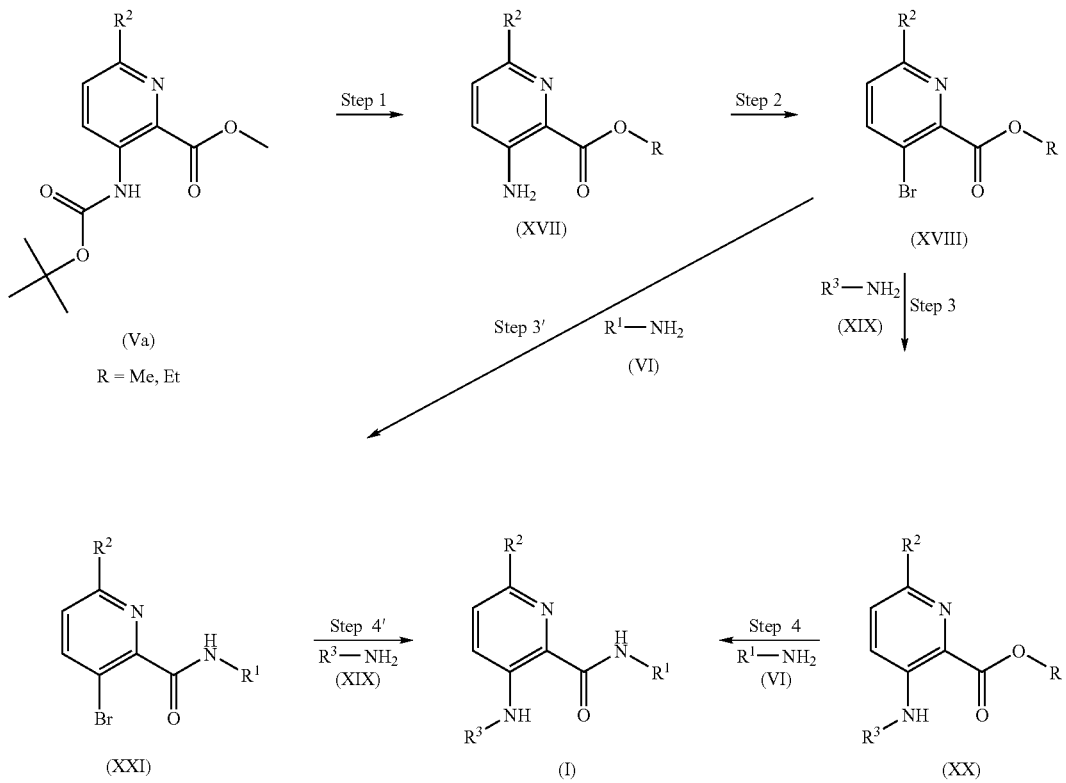

General Procedure III

Step 1:

The compound of formula (XVII) can be obtained by stirring an acidic solution of a compound of formula (Va) in a suitable solvent (e.g. methanol). The compound of formula (XVII) can be isolated and purified using conventional methods.

Step 2:

The compound of formula (XVIII) can be obtained by diazonization of the compound of formula (XVII) with sodium nitrite or an organic nitrite derivative, such as tert-Butyl- or isoamyl-nitrite, in the presence of copper (II) bromide in an organic solvent (Sandmeyer reaction). The compound of formula (XVIII) can then be isolated and purified using conventional methods.

Step 3:

The compound of formula (XX) can be obtained by a catalyzed coupling with an amine compound of formula (XIX), using, e.g., Cesium carbonate, Xanthphos and $Pd_2(dba)_3 \cdot CHCl_3$. The compound of formula (XX) can then be isolated and purified using conventional methods.

Step 4:

To a solution of a commercially available amine compound of formula (VI) in a solvent (e.g. dry dioxane) a solution of trimethyl aluminium in hexane is added. A compound of formula (XX) is then added. After the reaction is finished, the compound of formula (I) can be isolated and purified using conventional methods.

Step 3':

To a solution of a commercially available amine compound of formula (VI) in a solvent (e.g. dry dioxane) a solution of trimethyl aluminium in hexane is added. A compound of formula (XVIII) is then added. After the reaction is finished, the compound of formula (XXI) can then be isolated and purified using conventional methods.

Step 4':

The compound of formula (I) wherein can be obtained by a Palladium catalyzed coupling of a compound of formula (XXI) with an amine compound of formula (XIX), using, e.g., Cesium carbonate, Xanthphos and $Pd_2(dba)_3 \cdot CHCl_3$. The compound of formula (I) can then be isolated and purified using conventional methods.

Scheme 4:

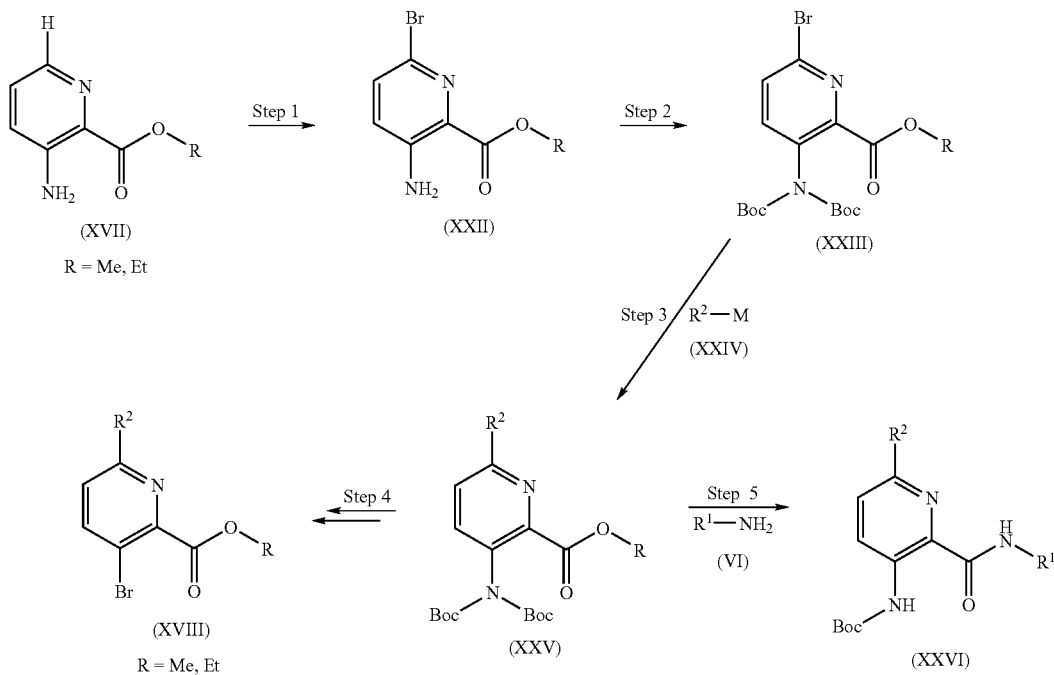

General Procedure IV: (Variations of the Group $R^2$):

Step 1:

The compound of formula (XXII) can be obtained by reaction of a compound of formula (XVII) (where $R^2$ is hydrogen) with a bromination reagent (e.g. Bromine, NBS, etc.) in a suitable solvent (e.g. Acetonitrile). The compound of formula (XXII) can be isolated and purified using conventional methods.

Step 2:

The compound of formula (XXIII) can be obtained by Boc protection of the compound of formula (XXII) with Di-tert-butyl-dicarbonate (Boc)$_2$O in presence of an organic or inorganic base (e.g. DMAP, Triethylamine) in an organic solvent. The compound of formula (XXIII) can then be isolated and purified using conventional methods.

Step 3:

The compound of formula (XXV) can be obtained by a Pd-catalyzed coupling with an organometallic reagent of formula (XXIV) (e.g. organozinc reagents such as dialkyzinc derivatives, alkylzinc halides, or organotin reagents such as tetraalkyltin compounds) using, e.g., Tetrakis(triphenylphosphine)palladium in an appropriate organic solvent (e.g. Dioxane or THF). The compound of formula (XXV) can then be isolated and purified using conventional methods.

Step 4:

The compound of formula (XVIII) can be obtained by Boc-deprotection of a compound of formula (XXV) in presence of an organic or inorganic acid (e.g. HCl, of trifluoroacetic acid) in a suitable solvent (e.g. methanol, methylene chloride). The deprotection step is followed by diazonization of the resulting aromatic amine with sodium nitrite or an organic nitrite derivative such as tert-Butyl- or isoamyl-nitrite in presence of copper (II) bromide in an organic solvent (Sandmeyer reaction). The compound of formula (XVIII) can then be isolated and purified using conventional methods.

Step 5:

To a solution of an amine compound of formula (VI) in a solvent (e.g. dry dioxane) a solution of trimethyl aluminium in hexane is added. A compound of formula (XXV) is then added. After the reaction is finished, the compound of formula (XXVI) can be isolated and purified using conventional methods.

The compounds of formula (XVIII) can be further transformed into compounds of formula (I) using methods described under the general procedure III. The compounds of formula (XXVI) can be Boc-deprotected to form compounds of formula (VIII) which can then be transformed into compounds of formula (I) using methods already described under the general procedure I.

Pharmaceutically acceptable salts of compounds of formula I can be manufactured readily according to methods known per se and taking into consideration the nature of the compound to be converted into a salt. Inorganic or organic acids such as, for example, hydrochloric acid, hydrobromic acid, sulphuric acid, nitric acid, phosphoric acid or citric acid, formic acid, fumaric acid, maleic acid, acetic acid, succinic acid, tartaric acid, methanesulphonic acid, p-toluene-sulphonic acid and the like are suitable for the formation of pharmaceutically acceptable salts of basic compounds of formula I. Compounds which contain the alkali metals or alkaline earth metals, for example sodium, potassium, calcium, magnesium or the like, basic amines or basic amino acids are suitable for the formation of pharmaceutically acceptable salts of acidic compounds.

As already mentioned above, the compounds of formula (I) and their pharmaceutically acceptable salts are, as already mentioned above, metabotropic glutamate receptor antagonists and can be used for the treatment of mGluR5 receptor mediated disorders, such as acute and/or chronic neurological disorders, cognitive disorders and memory deficits, as well as acute and chronic pain. Treatable neurological disorders are, for instance, epilepsy, schizophrenia, anxiety, acute, traumatic or chronic degenerative processes of the nervous system, such as Alzheimer's disease, senile dementia, Huntington's chorea, ALS, multiple sclerosis, dementia caused by AIDS, eye injuries, retinopathy, idiopathic parkinsonism or parkinsonism caused by medicaments as well as conditions which lead to glutamate-deficient functions, such as e.g. muscle spasms, convulsions, migraine, urinary incontinence, ethanol addiction, nicotine addiction, psychoses, opiate addiction, anxiety, vomiting, dyskinesia and depression. Other treatable indications are restricted brain function caused by bypass operations or transplants, poor blood supply to the brain, spinal cord injuries, head injuries, hypoxia caused by pregnancy, cardiac arrest and hypoglycaemia. Furthermore restricted brain function leading to mental retardation due to abnormalities during pregnancy, retarded brain development or genetic anomalies such as Fragile-X syndrome, Down syndrome, or Autism spectrum disorders (Kanner's syndrome, Pervasive developmental disorder (PDD), Asperger's syndrome), attention deficit disorder (ADD), behavioral disorders such as obsessive compulsive disorder (OCD), eating disorders (anorexia, bulimia), are also possible treatable indications.

The compounds of formula I and their pharmaceutically acceptable salts are especially useful as analgesics. Treatable kinds of pain include inflammatory pain such as arthritis and rheumatoid disease, vasculitis, neuropathic pain such as trigeminal or herpetic neuralgia, diabetic neuropathy pain, causalgia, hyperalgesia, severe chronic pain, post-operative pain and pain associated with various conditions like cancer, angina, renal or billiary colic, menstruation, migraine and gout.

The pharmacological activity of the compounds was tested using the following method: For binding experiments, cDNA encoding human mGlu 5a receptor was transiently transfected into EBNA cells using a procedure described by Schlaeger and Christensen [Cytotechnology 15:1-13 (1998)]. Cell membrane homogenates were stored at −80° C. until the day of assay where upon they were thawed and resuspended and polytronized in 15 mM Tris-HCl, 120 mM NaCl, 100 mM KCl, 25 mM CaCl$_2$, 25 mM MgCl$_2$ binding buffer at pH 7.4 to a final assay concentration of 20 µg protein/well.

Saturation isotherms were determined by addition of twelve [$^3$H]MPEP concentrations (0.04-100 nM) to these membranes (in a total volume of 200 µl) for 1 h at 4° C. Competition experiments were performed with a fixed concentration of [$^3$H]MPEP (2 nM), and IC$_{50}$ values of test compounds evaluated using 11 concentrations (0.3-10,000 nM). Incubations were performed for 1 h at 4° C.

At the end of the incubation, membranes were filtered onto unifilter (96-well white microplate with bonded GF/C filter preincubated 1 h in 0.1% PEI in wash buffer, Packard BioScience, Meriden, Conn.) with a Filtermate 96 harvester (Packard BioScience) and washed 3 times with cold 50 mM Tris-HCl, pH 7.4 buffer. Nonspecific binding was measured in the presence of 10 µM MPEP. The radioactivity on the filter was counted (3 min) on a Packard Top-count microplate scintillation counter with quenching correction after addition of 45 µl of microscint 40 (Canberra Packard S. A., Zürich, Switzerland) and shaking for 20 min.

For functional assays, [Ca$^{2+}$]i measurements were performed as described previously by Porter et al. [Br. J. Pharmacol. 128:13-20 (1999)] on recombinant human mGlu 5a receptors in HEK-293 cells. The cells were dye loaded using Fluo 4-AM (obtainable by FLUKA, 0.2 µM final concentration). [Ca$^{2+}$]i measurements were performed using :a fluorometric imaging plate reader (FLIPR, Molecular Devices Corporation, La Jolla, Calif., USA). Antagonist evaluation was performed following a 5 min preincubation with the test compounds followed by the addition of a submaximal addition of agonist.

The inhibition (antagonists) curves were fitted with a four parameter logistic equation giving IC$_{50}$, and Hill coefficient using iterative non linear curve fitting software (Xcel fit).

For binding experiments the Ki values of the compounds tested are given. The Ki value is defined by the following formula:

$$K_i = IC_{50}/[1+L/K_d]$$

in which the IC$_{50}$ values are those concentrations of the compounds tested which cause 50% inhibition of the competing radioligand ([$^3$H]MPEP). L is the concentration of radioligand used in the binding experiment and the K$_d$ value of the radioligand is empirically determined for each batch of membranes prepared.

The compounds of the present invention are mGluR 5a receptor antagonists. The activities of compounds of formula I as measured in the assay described above are in the range of K$_i$<4 µM and preferably <150 nM.

| Ex. | Ki (mGluR5) [nM] |
|---|---|
| 2 | 30 |
| 4 | 42 |
| 8 | 21 |
| 14 | 28 |
| 16 | 27 |
| 18 | 78 |
| 22 | 66 |
| 51 | 82 |
| 54 | 55 |
| 60 | 367 |
| 92 | 10 |
| 96 | 57 |
| 103 | 14 |
| 106 | 56 |

The present invention also provides pharmaceutical compositions containing compounds of the invention or pharmaceutically acceptable salts thereof and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula I, but as a rule or not necessary. Suitable carriers for suppositories are, for example, natural or hardened oils, waxes, fats, semi-liquid or liquid polyols and the like.

In addition, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a process for the manufacture of pharmaceutical compositions. Such process comprises bringing the compound of formula I and/or pharmaceutically acceptable salts thereof and, if desired, one or more other therapeutically valuable substances into a galenical administration form together with one or more therapeutically inert carriers.

The present invention further provides methods for the treatment of mGluR5 mediated disorders. In particular, the invention provides a method for treating a disorder selected from the group consisting of acute and/or chronic neurological disorders, anxiety, behavioral disorders, and obsessive compulsive disorder (OCD). The invention also provides a method for treating a disorder selected from anorexia and bulimia. The invention further provides a method for treating a disorder selected from the group consisting of schizophrenia, Alzheimer's disease, and Parkinson's disease. Such methods comprise administering to an individual a therapeutically effective amount of a compound of the invention and a pharmaceutically acceptable carrier.

The dosage at which compounds of the invention can be administered can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult human being weighing 70 kg accordingly lies between 0.7-1400 mg per day, preferably between 7 and 700 mg per day.

The following examples are provided to further elucidate the invention and are not intended to limit the invention to the sole compounds exemplified:

EXAMPLE 1

6-Methyl-3-(pyridin-3-ylamino)-pyridine-2-carboxylic acid (3-chloro-phenyl)-amide Step 1: 6-Methyl-pyridine-2-carboxylic acid-(3-chloro-phenyl)-amide A solution of 6-methylpicolinic acid (5.0 g, 36 mmol) in THF (60.0 ml) was treated with two drops of DMF and 3.5 ml (5.09 g, 40 mmol, 1.1 equiv.) of oxalyl chloride were added dropwise. The solution was stirred for 30 min at room temperature. The reaction mixture was then evaporated to dryness in vaccuo. The residue was taken up in 40 ml of dry THF, and cooled to 0° C. Triethylamine (6.1 ml, 4.43 g, 44 mmol, 1.2 equiv.), and a solution of 4.23 ml (5.12 g, 40 mmol, 1.1 equiv.) of 3-chloro-aniline in 15 ml of dry THF were added dropwise at 0° C. The reaction mixture was stirred for 5 min. at 0° C. and then allowed to warm up to room temperature. After stirring for 1 h at r.t., the dark brown suspension was filtered. The filtrate was concentrated in vaccuo, and the residue was dissolved in 200 ml of ethyl acetate, which was washed once with brine. The aqueous phase was extracted with ethyl acetate. The combined organic phases were dried over magnesium sulfate, filtered and concentrated in vaccuo. Concentration in vaccuo yielded 7.7 g of a dark brown residue which was purified by flash chromatography (heptane/ethyl acetate 4:1) to yield a the title compound as a white solid (total 5.05 g, 56%), MS (ISP): m/e=247.1, 249.1 (M+H$^+$).

Step 2: 3-Iodo-6-methyl-pyridine-2-carboxylic acid (3-chloro-phenyl)-amide

A solution of 6-Methyl-pyridine-2-carboxylic acid-(3-chloro-phenyl)-amide (1.96 g, 7.9 mmol) in THF (20.0 ml) was cooled to −78° C. A 1.6 M solution of n-BuLi in hexane (11.0 ml, 17.6 mmol, 2.2 equiv.) was added dropwise and the reaction was stirred for 30 min at −78° C. A solution of 2.02 g (7.9 mmol) of iodine in THF (20.0 ml) was added dropwise maintaining the temperature below −75° C. After 5 min, the reaction mixture was allowed to warm up to r.t. The mixture was quenched by the addition of sat. ammonium sulfate soln. (5 ml) and 40% sodium hydrogensulfite solution (5 ml). The pH of the solution was adjusted to 8 by the addition of sat. bicarbonate soln. The mixture was then extracted twice with ethyl acetate. The combined organic phases were washed with water, dried over magnesium sulfate and concentrated in vaccuo. The dark brown residue (2.66 g) was purified by flash chromatography (heptane/ethyl acetate 9:1) to yield a the title compound as a beige solid (total 1.42 g, 48%), MS (ISP): m/e=373.0, 375.0 (M+H$^+$).

Step 3: 6-Methyl-3-(pyridin-3-ylamino)-pyridine-2-carboxylic acid (3-chloro-phenyl)-amide In a 5 ml microwave reaction vessel were dissolved 50 mg (0.134 mmol) 3-Iodo-6-methyl-pyridine-2-carboxylic acid (3-chloro-phenyl)-amide and 16 mg (0.168 mmol, 1.25 equiv.) of 3-aminopyridine in 2 ml of dioxane. Cesium carbonate (61 mg, 188 mmol, 1.4 equiv.) were added and argon was bubbled through the suspension for 3 min. Then Xanthphos (26 mg, 0.044 mmol, 0.33 equiv.) and Pd$_2$(dba)$_3$.CHCl$_3$ 14 mg (0.013 mmol, 0.1 equiv.) were added and the mixture was heated for 30 min at 150° C. under microwave irradiation. The mixture was diluted with methylene chloride, filtered and concentrated in vaccuo. The resulting dark brown oil (129 mg) was purified by flash chromatography (gradient: heptane/ethyl acetate 4:1 to 3:2) to yield the title compound as a yellow solid (total 11 mg, 24%), MS (ISP): m/e=339.1, 341.1 (M+H$^+$).

EXAMPLE 2

6-Methyl-3-(pyrimidin-5-ylamino)-pyridine-2-carboxylic acid (3-chloro-phenyl)-amide The title compound, MS (ISP): m/e=340.1, 342.0 (M+H$^+$), was prepared from 3-Iodo-6-methyl-pyridine-2-carboxylic acid (3-chloro-phenyl)-amide in accordance with the general method of example 1. Step 3 was performed using 5-aminopyrimidine (CAS:[591-55-9]) instead of 3-aminopyridine.

EXAMPLE 3

3-(5-Chloro-pyridin-3-ylamino)-6-methyl-pyridine-2-carboxylic acid (3-chloro-phenyl)amide The title compound, MS (ISP): m/e=373.1, 375.1 (M+H$^+$), was prepared from 3-Iodo-6-methyl-pyridine-2-carboxylic acid (3-chloro-phenyl)-amide in accordance with the general method of example 1. Step 3 was performed using 3-amino-5-chloropyridine (CAS:[22353-34-0]) instead of 3-aminopyridine.

EXAMPLE 4

6-Methyl-3-(pyridin-3-ylamino)-pyridine-2-carboxylic acid (2-chloro-pyridin-4-yl)-amide Step 1: 3-tert-Butoxycarbonylamino-6-methyl-pyridine-2-carboxylic acid methyl ester To a solution of 6-Methyl-pyridine-2,3-dicarboxylic acid 2-methyl ester (CAS:[135338-27-1]) (4.93 g, 25 mmol) and N-methylmorpholine (3.05 ml, 2.81 g, 28 mmol, 1.1 equiv.) in methylene chloride (100.0 ml) was added diphenylphosphoryl-azide (DPPA, 6.14 ml, 7.88 g, 28 mmol, 1.1 equiv.) dropwise at room temperature. The mixture was stirred for 30 min at r.t. and then heated to 70° C. for 2 h whereby nitrogen evolution is observed. Then tert-Butanol (3.56 ml, 2.81 g, 38 mmol, 1.5 equiv.) and copper(I) chloride (25 mg, 0.25 mmol, 0.01 equiv.) were added and the mixture was heated at 70° C. for another 4 h. The reaction mixture was allowed to cool to r.t., stirred overnight, and concentrated in vaccuo. The resulting dark brown oil (16.9 g) was purified by flash chromatography (heptane/ethyl acetate 3:2) to yield the title compound as a white solid (total 5.06 g, 75%), MS (ISP): m/e=267.2 (M+H$^+$).

Step 2: [2-(2-Chloro-pyridin-4-ylcarbamoyl)-6-methyl-pyridin-3-yl]-carbamic acid tert-butyl ester To a solution of 2-chloro-4-aminopyridine (0.97 g, 7.5 mmol, 4.0 equiv.) in dry dioxane (20.0 ml) were added 3.75 ml of a 2M solution of trimethyl aluminium in hexane (7.5 mmol, 4.0 equiv.) and the mixture was stirred for 1 h at r.t.. Then 3-tert-Butoxycarbonylamino-6-methyl-pyridine-2-carboxylic acid methyl ester (0.50 g, 1.88 mmol) were added and the reaction was refluxed for 2 h. After allowing the reaction to cool to r.t., the reaction was quenched with water (0.5 ml), stirred for 5 min, dried by addition of magnesium sulfate and filtered over Dicalite which was further washed with methylene chloride. The filtrate was concentrated in vaccuo. The residue was purified by flash chromatography (heptane/ethyl acetate 2:1) to yield the title compound as a white solid (total 0.50 g, 73%), MS (ISP): m/e=363.1, 365.0 (M+H$^+$).

Step 3: 3-Amino-6-methyl-pyridine-2-carboxylic acid (2-chloro-pyridin-4-yl)-amide A HCl saturated solution of [2-(2-Chloro-pyridin-4-ylcarbamoyl)-6-methyl-pyridin-3-yl]-carbamic acid tert-butyl ester (0.50 g, 1.38 mmol) in methanol (13.0 ml) was stirred overnight at r.t. and evaporated to dryness in vaccuo. The residual hydrochloride salt was taken up in 15 ml of water, the pH was adjusted to 8.5 by addition of sat. sodium carbonate solution. The resulting suspension was extracted twice with ethyl acetate. The combined organic phases were dried over magnesium sulfate and concentrated in vaccuo to yield the title compound as a white solid (total 0.35 g, 97%), MS (ISP): m/e=263.1, 265.1 (M+H$^+$).

Step 4: 6-Methyl-3-(pyridin-3-ylamino)-pyridine-2-carboxylic acid (2-chloro-pyridin-4-yl)-amide In a 5 ml microwave reaction vessel were dissolved 80 mg (0.31 mmol) 3-Amino-6-methyl-pyridine-2-carboxylic acid (2-chloro-pyridin-4-yl)-amide and 60 mg (0.38 mmol, 1.25 equiv.) of 3-Bromopyridine in 4 ml of dioxane. Cesium carbonate (139 mg, 0.43 mmol, 1.4 equiv.) were added and argon was bubbled through the suspension for 3 min. Then Xanthphos (58 mg, 0.10 mmol, 0.33 equiv.) and Pd$_2$(dba)$_3$.CHCl$_3$ (32 mg, 0.03 mmol, 0.1 equiv.) were added and the mixture was heated for 2 h at 160° C. under microwave irradiation. To the mixture was added silica gel (5 g) and the mixture was evaporated to dryness in vaccuo. The powder was charged onto a flash chromatography column and eluted (heptane/ethyl acetate 2:1) to yield the title compound as a yellow solid (total 43 mg, 41%), MS (ISP): m/e=340.1, 342.0 (M+H$^+$).

EXAMPLE 5

6-Methyl-3-(pyridin-3-ylamino)-pyridine-2-carboxylic acid (2-methyl-pyridin-4-yl)-amide The title compound was prepared from 3-tert-Butoxycarbonylamino-6-methyl-pyridine-2-carboxylic acid methyl ester in accordance with the general method of example 4; step 2 using 2-methyl-4-aminopyridine (CAS: [18437-58-6]) instead of 2-chloro-4-aminopyridine to yield [2-(2-Methyl-pyridin-4-ylcarbamoyl)-6-methyl-pyridin-3-yl]-carbamic acid tert-butyl ester, MS (ISP): m/e=343.1 (M+H+). Boc-deprotection as described in example 4 step 3 yielded 3-Amino-6-methyl-pyridine-2-carboxylic acid (2-methyl-pyridin-4-yl)-amide, MS (ISP): m/e=243.4 (M+H+). Palladium catalysed arylation with 3-Bromopyridine as described in example 4 step 4 yielded the final product as a light yellow solid, MS (ISP): m/e=320.0 (M+H+).

EXAMPLE 6

6-Methyl-3-(pyrimidin-5-ylamino)-pyridine-2-carboxylic acid (2-methyl-pyridin-4-yl)-amide The title compound, was prepared from 3-Amino-6-methyl-pyridine-2-carboxylic acid (2-methyl-pyridin-4-yl)-amide in accordance with the general method of example 20 using 5-bromopyrimidine instead of 3-Bromopyridine to yield the final compound as a beige solid, MS (ISP): m/e=321.0 (M+H+).

EXAMPLE 7

3-(5-Fluoro-pyridin-3-ylamino)-6-methyl-pyridine-2-carboxylic acid (2-methyl-pyridin-4-yl)-amide In a 5 ml microwave reaction vessel were dissolved 70 mg (0.29 mmol) 3-Amino-6-methyl-pyridine-2-carboxylic acid (2-methyl-pyridin-4-yl)-amide (Example 5) and 266 mg (2.31 mmol, 8.0 equiv.) of 3,5-difluoropyridine in 1.5 ml of DMF. Cesium carbonate (376 mg, 1.16 mmol, 4.0 equiv.) was added and the suspension was sonicated under argon for 10 min. The mixture was heated for 72 h at 120° C. in an oil bath and then 1 h at 160° C. under microwave irradiation. The dark brown suspension was filtered over Dicalite which was washed with ethyl acetate. The filtrate was evaporated to dryness in vaccuo, and the residue dissolved in 200 ml of ethyl acetate, which was washed once with brine. After drying over magnesium sulfate and concentration in vaccuo, the residue (90 mg) was purified by flash chromatography (gradient heptane/ethyl acetate 1:1 to 0:1 ) to yield the title compound, light yellow solid, (23 mg, 24%). MS (ISP): m/e=338.1 (M+H+).

EXAMPLE 8

6-Methyl-3-(pyridin-3-ylamino)-pyridine-2-carboxylic acid (5-fluoro-pyridin-2-yl)-amide The title compound, was prepared in accordance with the general method of example 4, step 2 using 2-amino-5-fluoropyridine instead of 2-chloro-4-aminopyridine to yield [2-(5-Fluoro-pyridin-2-ylcarbamoyl)-6-methyl-pyridin-3-yl]- carbamic acid tert-butyl ester as a white solid. MS (ISP): m/e=347.0 (M+H+). Boc-deprotection as described in example 4 step 3 yielded 3-Amino-6-methyl-pyridine-2-carboxylic acid (5-fluoro-pyridin-2-yl)-amide as a light yellow solid, MS (ISP): m/e=247.3 (M+H+). Palladium catalysed arylation with 3-Bromopyridine as described in example 4 step 4 yielded the final product as a light yellow solid, MS (ISP): m/e=324.3 (M+H+).

EXAMPLE 9

6-Methyl-3-(pyrimidin-5-ylamino)-pyridine-2-carboxylic acid (5-fluoro-pyridin-2-yl)-amide The title compound, MS (ISP): m/e=325.0 (M+H+), was prepared from 3-Amino-6-methyl-pyridine-2-carboxylic acid (5-fluoro-pyridin-2-yl)-amide in accordance with the general method of example 20 using 5-bromopyrimidine instead of 3-Bromopyridine.

EXAMPLE 10

3-(5-Fluoro-pyridin-3-ylamino)-6-methyl-pyridine-2-carboxylic acid (5-fluoro-pyridin-2-yl)-amide The title compound, light yellow solid, MS (ISP): m/e=342.1 (M+H+), was prepared from 3-Amino-6-methyl-pyridine-2-carboxylic acid (5-fluoro-pyridin-2-yl)-amide and 3,5-Difluoropyridine in accordance with the general method of example 7.

EXAMPLE 11

6-Methyl-3-(pyridin-3-ylamino)-pyridine-2-carboxylic acid (5-fluoro-6-methyl-pyridin-2-yl)-amide The title compound was prepared from 3-tert-Butoxy-carbonylamino-6-methyl-pyridine-2-carboxylic acid methyl ester in accordance with the general method of example 4; step 2 using 2-amino-5-fluoro-6-methylpyridine (Sanchez & al., J. Heterocycl. Chem. 24, 215(1987); CAS:[110919-71-6]) instead of 2-chloro-4-aminopyridine to yield [2-(5-Fluoro-6-methyl-pyridin-2-ylcarbamoyl)-6-methyl-pyridin-3-yl]-carbamic acid tert-butyl ester, white solid, MS (ISP): m/e=361.0 (M+H+). Boc-deprotection as described in example 4 step 3 yielded 3-Amino-6-methyl-pyridine-2-carboxylic acid (5-fluoro-6-methyl-pyridin-2-yl)-amide, white solid, MS (ISP): m/e=261.3 (M+H+). Palladium catalysed arylation with 3-Bromopyridine as described in example 4 step 4 yielded the final product as a yellow solid, (ISP): m/e=338.1 (M+H+).

EXAMPLE 12

6-Methyl-3-(pyrimidin-5-ylamino)-pyridine-2-carboxylic acid (5-fluoro-6-methyl-pyridin-2-yl)-amide The title compound, light yellow solid, MS (ISP): m/e=339.3 (M+H+), was prepared from 3-Amino-6-methyl-pyridine-2-carboxylic acid (5-fluoro-6-methyl-pyridin-2-yl)-amide in accordance with the general method of example 20 using 5-bromopyrimidine instead of 3-Bromopyridine.

EXAMPLE 13

3-(5-Fluoro-pyridin-3-ylamino)-6-methyl-pyridine-2-carboxylic acid (5-fluoro-6-methyl-pyridin-2-yl)-amide The title compound, light yellow solid, MS (ISP): m/e=356.1 (M+H+), was prepared from 3-Amino-6-methyl-pyridine-2-carboxylic acid (5-fluoro-6-methyl-pyridin-2-yl)-amide and 3,5-Difluoropyridine in accordance with the general method of example 7.

EXAMPLE 14

6-Methyl-3-(pyridin-3-ylamino)-pyridine-2-carboxylic acid (4-methyl-thiazol-2-yl)-amide The title compound, was prepared in accordance with the general method of example 4, step 2 using 2-amino-4-methylthiazole instead of 2-chloro-4-aminopyridine to yield 6-Methyl-2-(4-methyl-thiazol-2-ylcarbamoyl)-pyridin-3-yl]-carbamic acid tert-butyl ester as a light yellow solid. MS (ISP): m/e=349.0 (M+H+). Boc-deprotection as described in example 4 step 3 yielded 3-Amino-6-methyl-pyridine-2-carboxylic acid (4-methyl-thiazol-2-yl)-amide as an off-white solid, MS (ISP): m/e=249.4 (M+H+). Palladium catalysed arylation with 3-Bromopyridine as described in example 4 step 4 yielded the final product as a yellow solid, MS (ISP): m/e=326.0 (M+H+).

EXAMPLE 15

6-Methyl-3-(pyrimidin-5-ylamino)-pyridine-2-carboxylic acid (4-methyl-thiazol-2-yl)-amide The title compound, light brown solid, MS (ISP): m/e=327.0 (M+H+), was prepared from 3-Amino-6-methyl-pyridine-2-carboxylic acid (4-methyl-thiazol-2-yl)-amide in accordance with the general method of example 20 using 5-bromopyrimidine instead of 3-bromo-pyridine.

EXAMPLE 16

6-Methyl-3-(pyridin-3-ylamino)-pyridine-2-carboxylic acid (1-methyl-1H-pyrazol-3-yl)-amide The title compound, was prepared in accordance with the general method of example 4, step 2 using 1-Methyl-1H-pyrazol-3-ylamine instead of 2-chloro-4-aminopyridine to yield [6-Methyl-2-(1-methyl-1H-pyrazol-3-ylcarbamoyl)-pyridin-3-yl]-carbamic acid tert-butyl ester as an off-white solid. MS (ISP): m/e=332.0 (M+H+). Boc-deprotection as described in example 4 step 3 yielded 3-Amino-6-methyl-pyridine-2-carboxylic acid (1-methyl-1H-pyrazol-3-yl)-amide as an off-white solid, MS (ISP): m/e=232.3 (M+H+). Palladium catalysed arylation with 3-Bromopyridine as described in example 4 step 4 yielded the final product as a light brown solid, MS (ISP): m/e=309.1 (M+H+).

EXAMPLE 17

6-Methyl-3-(pyrimidin-5-ylamino)-pyridine-2-carboxylic acid (1-methyl-1H-pyrazol-3-yl)-amide The title compound, light brown solid, MS (ISP): m/e=310.4 (M+H+), was prepared from 3-Amino-6-methyl-pyridine-2-carboxylic acid (1-methyl-1H-pyrazol-3-yl)- amide in accordance with the general method of example 20 using 5-bromopyrimidine instead of 3-bromo-pyridine.

EXAMPLE 18

6-Methyl-3-(pyridin-3-ylamino)-pyridine-2-carboxylic acid (4-trifluoromethyl-thiazol-2-yl)-amide The title compound, was prepared in accordance with the general method of example 4, step 2 using 4-Trifluoromethyl-thiazol-2-ylamine instead of 2-Chloro-4-aminopyridine to yield [6-Methyl-2-(4-trifluoromethyl-thiazol-2-ylcarbamoyl)-pyridin-3-yl]-carbamic acid tert-butyl ester as an off-white solid. MS (ISP): m/e=403.0 (M+H+). Boc-deprotection as described in example 4 step 3 yielded 3-Amino-6-methyl-pyridine-2-carboxylic acid (4-trifluoromethyl-thiazol-2-yl)-amide as an off-white solid, MS (ISP): m/e=303.0 (M+H+). Palladium catalysed arylation with 3-Bromopyridine as described in example 4 step 4 yielded the final product as a yellow solid, MS (ISP): m/e=380.0 (M+H+).

EXAMPLE 19

6-Methyl-3-(pyrimidin-5-ylamino)-pyridine-2-carboxylic acid (4-trifluoromethyl-thiazol-2-yl)-amide The title compound, light yellow solid, MS (ISP): m/e=381.0 (M+H+), was prepared from 3-Amino-6-methyl-pyridine-2-carboxylic acid (4-trifluoromethyl-thiazol-2-yl)-amide in accordance with the general method of example 20 using 5-bromopyrimidine instead of 3-bromo-pyridine.

EXAMPLE 20

6-Methyl-3-(4-methyl-pyridin-3-ylamino)-pyridine-2-carboxylic acid (2-methyl-pyridin-4-yl)-amide In a 10 ml reaction vessel were dissolved 55 mg (0.23 mmol) 3-Amino-6-methyl-pyridine-2-carboxylic acid (2-chloro-pyridin-4-yl)-amide (example 5) and 81 mg (0.45 mmol, 2.0 equiv.) of 3-Bromo-4-methylpyridine in 3 ml of dioxane. Cesium carbonate (148 mg, 0.45 mmol, 2.0 equiv.) were added and argon was bubbled through the suspension for 3 min. Then Xanthphos (43 mg, 0.075 mmol, 0.33 equiv.) and Pd$_2$(dba)$_3$.CHCl$_3$ (23.5 mg, 0.023 mmol, 0.1 equiv.) were added, the vessel was closed and the mixture was heated for 19 h at 130° C. To the mixture was added silicagel (5 g) and the mixture was evaporated to dryness in vaccuo. The powder was charged onto a flash chromatography column and eluted (heptane/ethyl acetate 4:1) to yield the title compound as a yellow crystalline solid (total 28 mg, 28%), MS (ISP): m/e=334.0 (M+H+).

EXAMPLE 21

6-Methyl-3-(2-methyl-pyridin-3-ylamino)-pyridine-2-carboxylic acid (2-methyl-pyridin-4-yl)-amide The title compound, was prepared from 3-Amino-6-methyl-pyridine-2-carboxylic acid (2-methyl-pyridin-4-yl)-amide (example 5) in accordance with the general method of example 20 using 3-Bromo-2-methylpyridine instead of 3-Bromo-4-methylpyridine to yield the final compound as a yellow crystalline solid, MS (ISP): m/e=334.1 (M+H+).

EXAMPLE 22

3-(5-Cyano-pyridin-3-ylamino)-6-methyl-pyridine-2-carboxylic acid (2-methyl-pyridin-4-yl)-amide The title compound, was prepared from 3-Amino-6-methyl-pyridine-2-carboxylic acid (2-methyl-pyridin-4-yl)-amide (example 5) in accordance with the general method of example 20 using 5-Bromo-3-cyanopyridine instead of 3-Bromo-4-methylpyridine to yield the final compound as a light yellow crystalline solid, MS (ISP): m/e=345.0 (M+H+).

EXAMPLE 23

3-(3-Fluoro-phenylamino)-6-methyl-pyridine-2-carboxylic acid (2-methyl-pyridin-4-yl)-amide The title compound, was prepared from 3-Amino-6-methyl-pyridine-2-carboxylic acid (2-methyl-pyridin-4-yl)-amide (example 5) in accordance with the general method of example 20 using 1-Bromo-3-fluorobenzene instead of 3-Bromo-4-methylpyridine to yield the final compound as a yellow crystalline solid, MS (ISP): m/e=337.3 (M+H+).

EXAMPLE 24

3-(3-Cyano-phenylamino)-6-methyl-pyridine-2-carboxylic acid (2-methyl-pyridin-4-yl)-amide The title compound, was prepared from 3-Amino-6-methyl-pyridine-2-carboxylic acid (2-methyl-pyridin-4-yl)-amide (example 5) in accordance with the general method of example 20 using 3-Brombenzonitrile instead of 3-Bromo-4-methylpyridine to yield the final compound as a yellow crystalline solid, MS (ISP): m/e=344.0 (M+H+).

EXAMPLE 25

3-(3,5-Difluoro-phenylamino)-6-methyl-pyridine-2-carboxylic acid (2-methyl-pyridin-4-yl)-amide The title compound, was prepared from 3-Amino-6-methyl-pyridine-2-carboxylic acid (2-methyl-pyridin-4-yl)-amide (example 5) in accordance with the general method of example 20 using 1-Bromo-3,5-difluorobenzene instead of 3-Bromo-4-methylpyridine to yield the final compound as a yellow crystalline solid, MS (ISP): m/e=355.1 (M+H+).

EXAMPLE 26

6-Methyl-3-(4-methyl-pyridin-3-ylamino)-pyridine-2-carboxylic acid (5-fluoro-pyridin-2-yl)-amide The title compound, was prepared from 3-Amino-6-methyl-pyridine-2-carboxylic acid (5-fluoro-pyridin-2-yl)-amide (example 8) in accordance with the general method of example 5, step 6 using 3-Bromo-4-methylpyridine instead of 3-Bromopyridine to yield the final compound as a light yellow crystalline solid, MS (ISP): m/e=338.3 (M+H+).

EXAMPLE 27

6-Methyl-3-(2-methyl-pyridin-3-ylamino)-pyridine-2-carboxylic acid (5-fluoro-pyridin-2-yl)-amide The title compound, was prepared from 3-Amino-6-methyl-pyridine-2-carboxylic acid (5-fluoro-pyridin-2-yl)- amide (example 8) in accordance with the general method of example 20 using 3-Bromo-2-methylpyridine instead of 3-Bromo-4-methylpyridine to yield the final compound as a light yellow crystalline solid, MS (ISP): m/e=338.3 (M+H+).

EXAMPLE 28

3-(3-Fluoro-phenylamino)-6-methyl-pyridine-2-carboxylic acid (5-fluoro-pyridin-2-yl)-amide The title compound, was prepared from 3-Amino-6-methyl-pyridine-2-carboxylic acid (5-fluoro-pyridin-2-yl)-amide (example 8) in accordance with the general method of example 20 using 1-Bromo-3-fluorobenzene instead of 3-Bromo-4-methylpyridine to yield the final compound as a yellow crystalline solid, MS (ISP): m/e=341.1 (M+H+).

EXAMPLE 29

3-(3-Cyano-phenylamino)-6-methyl-pyridine-2-carboxylic acid (5-fluoro-pyridin-2-yl)-amide The title compound, was prepared from 3-Amino-6-methyl-pyridine-2-carboxylic acid (5-fluoro-pyridin-2-yl)-amide (example 8) in accordance with the general method of example 20 using 3-Bromobenzonitrile instead of 3-Bromo-4-methylpyridine to yield the final compound as a yellow crystalline solid, MS (ISP): m/e=348.0 (M+H+).

EXAMPLE 30

3-(3,5-Difluoro-phenylamino)-6-methyl-pyridine-2-carboxylic acid (5-fluoro-pyridin-2-yl)-amide The title compound, was prepared from 3-Amino-6-methyl-pyridine-2-carboxylic acid (5-fluoro-pyridin-2-yl)-amide (example 8) in accordance with the general method of example 20 using 1-Bromo-3,5-difluorobenzene instead of 3-Bromo-4-methylpyridine to yield the final compound as an off-white crystalline solid, MS (ISP): m/e=358.9 (M+H+).

EXAMPLE 31

6-Methyl-3-(4-methyl-pyridin-3-ylamino)-pyridine-2-carboxylic acid (4-methyl-thiazol-2-yl)-amide The title compound, was prepared from 3-Amino-6-methyl-pyridine-2-carboxylic acid (4-methyl-thiazol-2-yl)-amide (example 14) in accordance with the general method of example 20 using 3-Bromo-4-methylpyridine instead of 3-Bromo-4-methylpyridine to yield the final compound as an off-white solid, MS (ISP): m/e=340.3 (M+H+).

EXAMPLE 32

3-(5-Cyano-pyridin-3-ylamino)-6-methyl-pyridine-2-carboxylic acid (4-methyl-thiazol-2-yl)-amide The title compound, was prepared from 3-Amino-6-methyl-pyridine-2-carboxylic acid (4-methyl-thiazol-2-yl)-amide (example 14) in accordance with the general method of example 20 using 5-Bromo-3-cyanopyridine instead of 3-Bromo-4-methylpyridine to yield the final compound as an off-white solid, MS (ISP): m/e=351.1 (M+H+).

EXAMPLE 33

6-Methyl-3-(2-methyl-pyridin-3-ylamino)-pyridine-2-carboxylic acid (4-methyl-thiazol-2-yl)-amide The title compound, was prepared from 3-Amino-6-methyl-pyridine-2-carboxylic acid (4-methyl-thiazol-2-yl)-amide (example 14) in accordance with the general method of example 20 using 3-Bromo-2-methylpyridine instead of 3-Bromo-4-methylpyridine to yield the final compound as a yellow solid, MS (ISP): m/e=340.0 (M+H+).

EXAMPLE 34

3-(5-Fluoro-pyridin-3-ylamino)-6-methyl-pyridine-2-carboxylic acid (4-methyl-thiazol-2-yl)-amide The title compound, was prepared from 3-Amino-6-methyl-pyridine-2-carboxylic acid (4-methyl-thiazol-2-yl)-amide (example 14) in accordance with the general method of example 20 using 3-Bromo-5-fluoropyridine (CAS [407-20-5]) instead of 3-Bromo-4-methylpyridine to yield the final compound as a yellow solid, MS (ISP): m/e=344.0 (M+H+).

The above mentioned starting material, 3-Bromo-5-fluoropyridine was synthesized from commercially available 5-Bromonicotinamide as follows:

Step 1: 3-Amino-5-bromopyridine:

To a ice-cold solution of 31.8 g (0.79 mol) of Sodium hydroxide and 40.7 g (0.255 mol) of Bromine in 340 ml of water were added 42.0 g (0.209 mol) of commercially available 5-Bromonicotinamide. The mixture was allowed to warm up to room temperature and then heated for 1 h at 70° C. The resulting brown suspension was allowed to cool to room temperature. The aqueous phase was saturated with brine and extracted three times with a 1:1 mixture of THF and t-Butyl-methyl ether. The combined organic phases were dried over magnesium sulfate, filtered and concentrated in vaccuo. Concentration in vaccuo yielded 39.1 g of a dark brown residue which was purified by flash chromatography (heptane/ethyl acetate 1:1) to yield the title compound as a brown solid (total 70.2 g, 70%), MS (ISP): m/e=173.1, 175.1 (M+H+).

Step 2: 3-Bromo-5-fluoropyridine:

A at −10° C. cooled solution of 10.0 g (0.058 mol) of 3-Amino-5-bromopyridine in 59 ml of 50% Tetrafluoroboric acid was treated by dropwise addition of a solution of 4.19 g (0.06 mol) of sodium nitrite in 13 ml of water. After stirring for 1 h at −8° C., 150 ml of ether was added to the brown suspension. The crude diazonium salt was filtered off, and washed with ether. This crude salt was then added in portions to 200 ml of toluene heated at 80° C. After stirring for 1 h at 90° C., the organic phase was concentrated. The light yellow residue was suspended in 150 ml of water and the pH was adjusted to 11 with 32% sodium hydroxide solution. The resulting solution was extracted three times with 200 ml of methylene chloride. The combined organic phases were washed with water, dried over magnesium sulfate and concentrated. The crude material 15.4 g (brown oil) was purified by vaccum distillation (10 mBar, 35° C.) and yielded 5.6 g (0.032 mol, 55%) of the title compound as a colorless oil (ISP): m/e=176.1, 178.1 (M+H$^+$).

EXAMPLE 35

3-(3-Fluoro-phenylamino)-6-methyl-pyridine-2-carboxylic acid (4-methyl-thiazol-2-yl)-amide The title compound, was prepared from 3-Amino-6-methyl-pyridine-2-carboxylic acid (4-methyl-thiazol-2-yl)-amide (example 14) in accordance with the general method of example 20 using 1-Bromo-3-fluorobenzene instead of 3-Bromo-4-methylpyridine to yield the final compound as a yellow solid, MS (ISP): m/e=343.1 (M+H+).

EXAMPLE 36

3-(3,5-Difluoro-phenylamino)-6-methyl-pyridine-2-carboxylic acid (4-methyl-thiazol-2-yl)-amide The title compound, was prepared from 3-Amino-6-methyl-pyridine-2-carboxylic acid (4-methyl-thiazol-2-yl)-amide (example 14) in accordance with the general method of example 20 using 1-Bromo-3,5-difluorobenzene instead of 3-Bromo-4-methylpyridine to yield the final compound as a yellow solid, MS (ISP): m/e=361.4 (M+H+).

EXAMPLE 37

6-Methyl-3-phenylamino-pyridine-2-carboxylic acid (4-methyl-thiazol-2-yl)-amide

The title compound, was prepared from 3-Amino-6-methyl-pyridine-2-carboxylic acid (4-methyl-thiazol-2-yl)-amide (example 14) in accordance with the general method of example 20 using Bromobenzene instead of 3-Bromo-4-methylpyridine to yield the final compound as a yellow solid, MS (ISP): m/e=325.0 (M+H+).

EXAMPLE 38

3-(3-Cyano-5-fluoro-phenylamino)-6-methyl-pyridine-2-carboxylic acid (4-methyl-thiazol-2-yl)-amide The title compound, was prepared from 3-Amino-6-methyl-pyridine-2-carboxylic acid (4-methyl-thiazol-2-yl)-amide (example 14) in accordance with the general method of example 20 using 3-Bromo-5-fluorobenzonitrile instead of 3-Bromo-4-methylpyridine to yield the final compound as a light yellow solid, MS (ISP): m/e=367.9 (M+H+).

EXAMPLE 39

3-(3-Cyano-phenylamino)-6-methyl-pyridine-2-carboxylic acid (4-methyl-thiazol-2-yl)-amide The title compound, was prepared from 3-Amino-6-methyl-pyridine-2-carboxylic acid (4-methyl-thiazol-2-yl)-amide (example 14) in accordance with the general method of example 20 using 3-Bromobenzonitrile instead of 3-Bromo-4-methylpyridine to yield the final compound as a yellow solid, MS (ISP): m/e=350.3 (M+H+).

EXAMPLE 40

3-(2-Chloro-pyridin-4-ylamino)-6-methyl-pyridine-2-carboxylic acid (4-methyl-thiazol-2-yl)-amide The title compound, was prepared from 3-Amino-6-methyl-pyridine-2-carboxylic acid (4-methyl-thiazol-2-yl)-amide (example 14) in accordance with the general method of example 20 using 4-Bromo-2-chloropyridine instead of 3-Bromo-4-methylpyridine to yield the final compound as a yellow solid, MS (ISP): m/e=360.1, 362.1 (M+H+).

EXAMPLE 41

3-(5-Cyano-pyridin-3-ylamino)-6-methyl-pyridine-2-carboxylic acid (1-methyl-1H-pyrazol-3-yl)-amide The title compound, was prepared from 3-Amino-6-methyl-pyridine-2-carboxylic acid (1-methyl-1H-pyrazol-3-yl)-amide (example 16) in accordance with the general method of example 20 using 5-Bromo-3-cyanopyridine instead of 3-Bromo-4-methylpyridine to yield the final compound as a light yellow solid, MS (ISP): m/e=334.3 (M+H+).

EXAMPLE 42

6-Methyl-3-(4-methyl-pyridin-3-ylamino)-pyridine-2-carboxylic acid (1-methyl-1H-pyrazol-3-yl)-amide The title compound, was prepared from 3-Amino-6-methyl-pyridine-2-carboxylic acid (1-methyl-1H-pyrazol-3-yl)-amide (example 16) in accordance with the general method of example 20 using 3-Bromo-4-methylpyridine instead of 3-Bromo-4-methylpyridine to yield the final compound as a light brown solid, MS (ISP): m/e=323.5 (M+H+).

EXAMPLE 43

6-Methyl-3-(2-methyl-pyridin-3-ylamino)-pyridine-2-carboxylic acid (1-methyl-1H-pyrazol-3-yl)-amide The title compound, was prepared from 3-Amino-6-methyl-pyridine-2-carboxylic acid (1-methyl-1H-pyrazol-3-yl)-amide (example 16) in accordance with the general method of example 20 using 3-Bromo-2-methylpyridine instead of 3-Bromo-4-methylpyridine to yield the final compound as a orange solid, MS (ISP): m/e=323.1 (M+H+).

EXAMPLE 44

3-(5-Fluoro-pyridin-3-ylamino)-6-methyl-pyridine-2-carboxylic acid (1-methyl-1H-pyrazol-3-yl)-amide The title compound, was prepared from 3-Amino-6-methyl-pyridine-2-carboxylic acid (1-methyl-1H-pyrazol-3-yl)-amide (example 16) in accordance with the general method of example 20 using 3-Bromo-5-fluoropyridine instead of 3-Bromo-4-methylpyridine to yield the final compound as a yellow solid, MS (ISP): m/e=327.1 (M+H+).

EXAMPLE 45

3-(3,5-Difluoro-phenylamino)-6-methyl-pyridine-2-carboxylic acid (1-methyl-1H-pyrazol-3-yl)-amide The title compound, was prepared from 3-Amino-6-methyl-pyridine-2-carboxylic acid (1-methyl-1H-pyrazol-3-yl)-amide (example 16) in accordance with the general method of example 20 using 1-Bromo-3,5-difluorobenzene instead of 3-Bromo-4-methylpyridine to yield the final compound as a light yellow solid, MS (ISP): m/e=344.0 (M+H+).

EXAMPLE 46

3-(3-Cyano-phenylamino)-6-methyl-pyridine-2-carboxylic acid (1-methyl-1H-pyrazol-3-yl)-amide The title compound, was prepared from 3-Amino-6-methyl-pyridine-2-carboxylic acid (1-methyl-1H-pyrazol-3-yl)- amide (example 16) in accordance with the general method of example 20 using 3-Bromobenzonitrile instead of 3-Bromo-4-methylpyridine to yield the final compound as a yellow solid, MS (ISP): m/e=333.3 (M+H+).

EXAMPLE 47

3-(3-Fluoro-phenylamino)-6-methyl-pyridine-2-carboxylic acid (1-methyl-1H-pyrazol-3-yl)-amide The title compound, was prepared from 3-Amino-6-methyl-pyridine-2-carboxylic acid (1-methyl-1H-pyrazol-3-yl)-amide (example 16) in accordance with the general method of example 20 using 1-Bromo-3-fluorobenzene instead of 3-Bromo-4-methylpyridine to yield the final compound as a light brown solid, MS (ISP): m/e=326.0 (M+H+).

EXAMPLE 48

3-(3-Cyano-5-fluoro-phenylamino)-6-methyl-pyridine-2-carboxylic acid (1-methyl-1H-pyrazol-3-yl)-amide The title compound, was prepared from 3-Amino-6-methyl-pyridine-2-carboxylic acid (1-methyl-1H-pyrazol-3-yl)-amide (example 16) in accordance with the general method of example 20 using 3-Bromo-5-fluorobenzonitrile instead of 3-Bromo-4-methylpyridine to yield the final compound as an off-white solid, MS (ISP): m/e=351.4 (M+H+).

EXAMPLE 49

6-Methyl-3-phenylamino-pyridine-2-carboxylic acid (1-methyl-1H-pyrazol-3-yl)-amide The title compound, was prepared from 3-Amino-6-methyl-pyridine-2-carboxylic acid (1-methyl-1H-pyrazol-3-yl)-amide (example 16) in accordance with the general method of example 20 using Bromobenzene instead of 3-Bromo-4-methylpyridine to yield the final compound as a yellow solid, MS (ISP): m/e=308.4 (M+H+).

EXAMPLE 50

3-(2-Chloro-pyridin-4-ylamino)-6-methyl-pyridine-2-carboxylic acid (1-methyl-1H-pyrazol-3-yl)-amide The title compound, was prepared from 3-Amino-6-methyl-pyridine-2-carboxylic acid (1-methyl-1H-pyrazol-3-yl)-amide (example 16) in accordance with the general method of example 20 using 4-Bromo-2-chloropyridine instead of 3-Bromo-4-methylpyridine to yield the final compound as an off-white solid, MS (ISP): m/e=343.0, 345.0 (M+H+).

EXAMPLE 51

6-Methyl-3-(5-trifluoromethyl-pyridin-3-ylamino)-pyridine-2-carboxylic acid (1-methyl-1H-pyrazol-3-yl)-amide The title compound, was prepared from 3-Amino-6-methyl-pyridine-2-carboxylic acid (1-methyl-1H-pyrazol-3-yl)-amide (example 16) in accordance with the general method of example 20 using 3-Bromo-5-(trifluoromethyl)pyridine instead of 3-Bromo-4-methylpyridine to yield the final compound as an off-white solid, MS (ISP): m/e=377.4 (M+H+).

EXAMPLE 52

6-Methyl-3-(4-methyl-pyridin-3-ylamino)-pyridine-2-carboxylic acid (5-fluoro-6-methyl-pyridin-2-yl)-amide The title compound, was prepared from 3-Amino-6-methyl-pyridine-2-carboxylic acid (5-fluoro-6-methyl-pyridin-2-yl)-amide (example 11) and 3-Bromo-4-methylpyridine in accordance with the general method of example 20 to yield the final compound as a light yellow crystalline solid, MS (ISP): m/e=352.0 (M+H+).

EXAMPLE 53

6-Methyl-3-(2-methyl-pyridin-3-ylamino)-pyridine-2-carboxylic acid (5-fluoro-6-methyl-pyridin-2-yl)-amide The title compound, was prepared from 3-Amino-6-methyl-pyridine-2-carboxylic acid (5-fluoro-6-methyl-pyridin-2-yl)-amide (example 11) in accordance with the general method of example 20 using 3-Bromo-2-methylpyridine instead of 3-Bromo-4-methylpyridine to yield the final compound as a light yellow crystalline solid, MS (ISP): m/e=352.1 (M+H+).

EXAMPLE 54

3-(3-Fluoro-phenylamino)-6-methyl-pyridine-2-carboxylic acid (5-fluoro-6-methyl-pyridin-2-yl)-amide The title compound, was prepared from 3-Amino-6-methyl-pyridine-2-carboxylic acid (5-fluoro-6-methyl-pyridin-2-yl)-amide (example 11) in accordance with the general method of example 20 using 1-Bromo-3-Fluorobenzene instead of 3-Bromo-4-methylpyridine to yield the final compound as a yellow crystalline solid, MS (ISP): m/e=355.3 (M+H+).

EXAMPLE 55

3-(3,5-Difluoro-phenylamino)-6-methyl-pyridine-2-carboxylic acid (5-fluoro-6-methyl-pyridin-2-yl)-amide The title compound, was prepared from 3-Amino-6-methyl-pyridine-2-carboxylic acid (5-fluoro-6-methyl-pyridin-2-yl)-amide (example 11) in accordance with the general method of example 20 using 1-Bromo-3,5-difluorobenzene instead of 3-Bromo-4-methylpyridine to yield the final compound as a light yellow crystalline solid, MS (ISP): m/e=373.1 (M+H+).

EXAMPLE 56

3-(3-Cyano-phenylamino)-6-methyl-pyridine-2-carboxylic acid (5-fluoro-6-methyl-pyridin-2-yl)-amide The title compound, was prepared from 3-Amino-6-methyl-pyridine-2-carboxylic acid (5-fluoro-6-methyl-pyridin-2-yl)-amide (example 11) in accordance with the general method of example 20 using 3-Bromobenzonitrile instead of 3-Bromo-4-methylpyridine to yield the final compound as a yellow solid, MS (ISP): m/e=362.3 (M+H+).

EXAMPLE 57

6-Methyl-3-(4-methyl-pyridin-3-ylamino)-pyridine-2-carboxylic acid (4-trifluoromethyl-thiazol-2-yl)-amide The title compound, was prepared from 3-Amino-6-methyl-pyridine-2-carboxylic acid (4-trifluoromethyl-thiazol-2-yl)-amide (example 18) and 3-Bromo-4-methylpyridine in accordance with the general method of example 20 to yield the final compound as a orange solid, MS (ISP): m/e=394.0 (M+H+).

EXAMPLE 58

3-(5-Cyano-pyridin-3-ylamino)-6-methyl-pyridine-2-carboxylic acid (4-trifluoromethyl-thiazol-2-yl)-amide The title compound, was prepared from 3-Amino-6-methyl-pyridine-2-carboxylic acid (4-trifluoromethyl-thiazol-2-yl)-amide (example 18) in accordance with the general method of example 20 using 5-Bromo-3-cyanopyridine instead of 3-Bromo-4-methylpyridine to yield the final compound as an off-white solid, MS (ISP): m/e=405.4 (M+H+).

EXAMPLE 59

3-(3-Fluoro-phenylamino)-6-methyl-pyridine-2-carboxylic acid (4-trifluoromethyl-thiazol-2-yl)-amide The title compound, was prepared from 3-Amino-6-methyl-pyridine-2-carboxylic acid (4-trifluoromethyl-thiazol-2-yl)-amide (example 18) in accordance with the general method of example 20 using 1-Bromo-3-fluorobenzene instead of 3-Bromo-4-methylpyridine to yield the final compound as a yellow solid, MS (ISP): m/e=397.1 (M+H+).

EXAMPLE 60

3-(3-Cyano-phenylamino)-6-methyl-pyridine-2-carboxylic acid (4-trifluoromethyl-thiazol-2-yl)-amide The title compound, was prepared from 3-Amino-6-methyl-pyridine-2-carboxylic acid (4-trifluoromethyl-thiazol-2-yl)-amide (example 18) in accordance with the general method of example 20 using 3-Bromobenzonitrile instead of 3-Bromo-4-methylpyridine to yield the final compound as a light brown solid, MS (ISP): m/e=404.0 (M+H+).

EXAMPLE 61

3-(3,5-Difluoro-phenylamino)-6-methyl-pyridine-2-carboxylic acid (4-trifluoromethyl-thiazol-2-yl)-amide The title compound, was prepared from 3-Amino-6-methyl-pyridine-2-carboxylic acid (4-trifluoromethyl-thiazol-2-yl)-amide (example 18) in accordance with the general method of example 20 using 1-Bromo-3,5-difluorobenzene instead of 3-Bromo-4-methylpyridine to yield the final compound as a yellow solid, MS (ISP): m/e=414.6 (M+H+).

EXAMPLE 62

6-Methyl-3-(pyrimidin-5-ylamino)-pyridine-2-carboxylic acid (2-methyl-thiazol-4-yl)-amide The title compound was prepared from 3-tert-Butoxy-carbonylamino-6-methyl-pyridine-2-carboxylic acid methyl ester in accordance with the general method of example 4; step 2 using 4-amino-2-methylthiazole (CAS: [103392-01-4], European Patent EP 321115) instead of 2-chloro-4-aminopyridine to yield [6-Methyl-2-(2-methyl-thiazol-4-ylcarbamoyl)-pyridin-3-yl]-carbamic acid tert-butyl ester as a light yellow cristalline solid, MS (ISP): m/e=349.0 (M+H+). Boc-deprotection as described in example 4 step 3 yielded 3-Amino-6-methyl-pyridine-2-carboxylic acid (2-methyl-thiazol-4-yl)-amide as a light yellow cristalline solid, MS (ISP): m/e=249.1 (M+H+). Palladium catalysed arylation with 5-bromopyrimidine as described in example 20 yielded the final compound as an off-white crystalline solid, MS (ISP): m/e=327.0 (M+H+).

EXAMPLE 63

6-Methyl-3-(pyridin-3-ylamino)-pyridine-2-carboxylic acid (2-methyl-thiazol-4-yl)-amide The title compound, was prepared from 3-Amino-6-methyl-pyridine-2-carboxylic acid (2-methyl-thiazol-4-yl)-amide and 3-Bromopyridine in accordance with the general method of example 20 to yield the final compound as a yellow crystalline solid, MS (ISP): m/e=326.0 (M+H+).

EXAMPLE 64

3-(5-Fluoro-pyridin-3-ylamino)-6-methyl-pyridine-2-carboxylic acid (2-methyl-thiazol-4-yl)-amide The title compound, was prepared from 3-Amino-6-methyl-pyridine-2-carboxylic acid (2-methyl-thiazol-4-yl)-amide and 3-Bromo-5-fluoropyridine in accordance with the general method of example 20 to yield the final compound as an off-white solid, MS (ISP): m/e=344.3 (M+H+).

EXAMPLE 65

3-(3,5-Difluoro-phenylamino)-6-methyl-pyridine-2-carboxylic acid [1-(2-methoxy-ethyl)-1H-pyrazol-3-yl]-amide The title compound was prepared from 3-tert-Butoxy-carbonylamino-6-methyl-pyridine-2-carboxylic acid methyl ester in accordance with the general method of example 4; step 2 using 1-(2-Methoxy-ethyl)-1H-pyrazol-3-yl amine instead of 2-chloro-4-aminopyridine to yield {2-[1-(2-Methoxy-ethyl)-1H-pyrazol-3-ylcarbamoyl]-6-methyl-pyridin-3-yl}-carbamic acid tert-butyl ester as a yellow oil, MS (ISP): m/e=376.5 (M+H+). Boc-deprotection as described in example 4 step 3 yielded 3-Amino-6-methyl-pyridine-2-carboxylic acid [1-(2-methoxy-ethyl)-1H-pyrazol-3-yl]-amide as a yellow oil, MS (ISP): m/e=276.3 (M+H+). Palladium catalysed arylation in accordance with the general method described in example 20 using 1-Bromo-3,5-difluorobenzene instead of 3-bromopyridine yielded the final compound as a light brown solid, MS (ISP): m/e=388.4 (M+H+).

The 1-(2-Methoxy-ethyl)-1H-pyrazol-3-yl amine used in the above example was synthesized according to the following procedure: 3-Aminopyrazole (2 g, 23 mmol) were dissolved in 15 ml DMSO. Potassium hydroxide (3.8 g, 69 mmol) was added and the mixture was stirred at room temperature for 30 min. 2-Bromoethyl methyl ether (3.2 g, 23 mmol) was added and stirring was continued at room temperature overnight. The reaction mixture was poured into 100 ml brine and extracted three time with 100 ml ethyl acetate. The organic phases were pooled, dried with sodium sulfate and evaporated. The two regiosomers were separated by flash chromatography and the title compound was obtained as a brown oil (0.824 g, 25%), MS (ISP): m/e=142.1 (M+H+).

EXAMPLE 66

3-(5-Fluoro-pyridin-3-ylamino)-6-methyl-pyridine-2-carboxylic acid [1-(2-methoxy-ethyl)-1H-pyrazol-3-yl]-amide The title compound, was prepared from 3-Amino-6-methyl-pyridine-2-carboxylic acid [1-(2-methoxy-ethyl)-1H-pyrazol-3-yl]-amide in accordance with the general method of example, step using 3,5-Difluoropyridine instead of 3-bromopyridineto yield the final compound as a off-white solid, MS (ISP): m/e=371.3 (M+H+).

EXAMPLE 67

6-Methyl-3-(pyrimidin-5-ylamino)-pyridine-2-carboxylic acid [1-(2-methoxy-ethyl)-1H-pyrazol-3-yl]-amide The title compound, was prepared from 3-Amino-6-methyl-pyridine-2-carboxylic acid [1-(2-methoxy-ethyl)-1H-pyrazol-3-yl]-amide in accordance with the general method of example, step using 5-Bromopyrimidine instead of 3-bromopyridineto yield the final compound as a off-white solid, MS (ISP): m/e=354.1 (M+H+).

EXAMPLE 68

3-(3-Cyano-phenylamino)-6-methyl-pyridine-2-carboxylic acid [1-(2-methoxy-ethyl)-1H-pyrazol-3-yl]-amide The title compound, was prepared from 3-Amino-6-methyl-pyridine-2-carboxylic acid [1-(2-methoxy-ethyl)-1H-pyrazol-3-yl]-amide in accordance with the general method of example, step using 3-Bromobenzonitrile instead of 3-bromopyridineto yield the final compound as a light yellow solid, MS (ISP): m/e=377.5 (M+H+).

EXAMPLE 69

3-(4-Fluoro-pyridin-2-ylamino)-6-methyl-pyridine-2-carboxylic acid [1-(2-methoxy-ethyl)-1H-pyrazol-3-yl]-amide The title compound, was prepared from 3-Amino-6-methyl-pyridine-2-carboxylic acid [1-(2-methoxy-ethyl)-1H-pyrazol-3-yl]-amide in accordance with the general method of example) step using 2-Chloro-4-fluoropyridine instead of 3-bromopyridineto yield the final compound as a off-white solid, MS (ISP): m/e=371.4 (M+H+).

EXAMPLE 70

3-(3-Fluoro-phenylamino)-6-methyl-pyridine-2-carboxylic acid [1-(2-methoxy-ethyl)-1H-pyrazol-3-yl]-amide The title compound, was prepared from 3-Amino-6-methyl-pyridine-2-carboxylic acid [1-(2-methoxy-ethyl)-1H-pyrazol-3-yl]-amide in accordance with the general method of example, step using 1-Bromo-3-fluorobenzene instead of 3-bromopyridineto yield the final compound as a yellow oil, MS (ISP): m/e=370.3 (M+H+).

EXAMPLE 71

3-(3-Cyano-5-fluoro-phenylamino)-6-methyl-pyridine-2-carboxylic acid [1-(2-methoxy-ethyl)-1H-pyrazol-3-yl]-amide The title compound, was prepared from 3-Amino-6-methyl-pyridine-2-carboxylic acid [1-(2-methoxy-ethyl)-1H-pyrazol-3-yl]-amide in accordance with the general method of example, step using 3-Bromo-5-fluorobenzonitrile instead of 3-bromopyridineto yield the final compound as a light yellow solid, MS (ISP): m/e=395.1 (M+H+).

EXAMPLE 72

6-Methyl-3-(pyrimidin-5-ylamino)-pyridine-2-carboxylic acid (4-methoxymethyl-thiazol-2-yl)-amide The title compound was prepared from 3-tert-Butoxy-carbonylamino-6-methyl-pyridine-2-carboxylic acid methyl ester in accordance with the general method of example 4; step 2 using 4-Methoxymethyl-thiazol-2-ylamine (CAS: [640768-40-7]; WO 2004081001) instead of 2-chloro-4-aminopyridine to yield [2-(4-Methoxymethyl-thiazol-2-ylcarbamoyl)-6-methyl-pyridin-3-yl]-carbamic acid tert-butyl ester as an off-white gum, MS (ISP): m/e=379.4 (M+H+). Boc-deprotection as described in example 4 step 3 yielded 3-Amino-6-methyl-pyridine-2-carboxylic acid (4-methoxymethyl-thiazol-2-yl)-amide as an off-white solid, MS (ISP): m/e=279.3 (M+H+). Palladium catalysed arylation in accordance with the general method of example 20, using 5-Bromopyrimidine instead of 3 bromopyridine yielded the final compound as a light yellow solid, MS (ISP): m/e=357.1 (M+H+).

EXAMPLE 73

3-(3,5-Difluoro-phenylamino)-6-methyl-pyridine-2-carboxylic acid (4-methoxymethyl-thiazol-2-yl)-amide The title compound, was prepared from 3-Amino-6-methyl-pyridine-2-carboxylic acid (4-methoxymethyl-thiazol-2-yl)-amide in accordance with the general method of example 20 using 1-Bromo-3,5-difluorobenzene instead of 3-bromopyridine to yield the final compound as a yellow solid, MS (ISP): m/e=391 (M+H+).

EXAMPLE 74

3-(5-Fluoro-pyridin-3-ylamino)-6-methyl-pyridine-2-carboxylic acid (4-methoxymethyl-thiazol-2-yl)-amide The title compound, was prepared from 3-Amino-6-methyl-pyridine-2-carboxylic acid (4-methoxymethyl-thiazol-2-yl)-amide in accordance with the general method of example 20 using 3-Bromo-5-fluoropyridine instead of 3-bromopyridine to yield the final compound as a light yellow solid, MS (ISP): m/e=374.3 (M+H+).

EXAMPLE 75

6-Methyl-3-(pyrimidin-5-ylamino)-pyridine-2-carboxylic acid (4-cyclopropyl-thiazol-2-yl)-amide The tide compound was prepared from 3-tert-Butoxy-carbonylamino-6-methyl-pyridine-2-carboxylic acid methyl ester in accordance with the general method of example 4; step 2 using 4-Cyclopropyl-thiazol-2-ylamine instead of 2-chloro-4-aminopyridine to yield [2-(4-Cyclopropyl-thiazol-2-ylcarbamoyl)-6-methyl-pyridin-3-yl]-carbamic acid tert-butyl ester as a yellow solid, MS (ISP): m/e=375.4 (M+H+). Boc-deprotection as described in example 4 step 3 yielded 3-Amino-6-methyl-pyridine-2-carboxylic acid (4-cyclopropyl-thiazol-2-yl)-amide as a yellow solid, MS (ISP): m/e=275.1 (M+H+). Palladium catalysed arylation in accordance with the general method of example 20, using 5-Bromopyrimidine instead of 3bromopyridine yielded the final compound as a light yellow solid, MS (ISP): m/e=357.1 (M+H+).

The 4-Cyclopropyl-thiazol-2-ylamine used in the above example was synthesized according to the following procedure:

A solution of 2-Bromo-1-cyclopropyl-ethanone (CAS [69267-75-0], Indian J. Chem. Sect. B, 22(9), 841(1983) (1 g, 6.1 mmol) and Thiourea (0.481 g, 6.1 mmol) in 15 ml of methanol was refluxed overnight. The solvent was evaporated off and the title compound was obtained as an off-white solid (1.38 g, 100%).

EXAMPLE 76

3-(5-Fluoro-pyridin-3-ylamino)-6-methyl-pyridine-2-carboxylic acid (4-cyclopropyl-thiazol-2-yl)-amide The title compound, was prepared from 3-Amino-6-methyl-pyridine-2-carboxylic acid (4-cyclopropyl-thiazol-2-yl)-amide in accordance with the general method of example 20 using 3-Bromo-5-fluoropyridine instead of 3-bromopyridine to yield the final compound as a yellow solid, MS (ISP): m/e=370.1 (M+H+).

EXAMPLE 77

6-Methyl-3-(pyridin-3-ylamino)-pyridine-2-carboxylic acid (4-cyclopropyl-thiazol-2-yl)-amide The title compound, was prepared from 3-Amino-6-methyl-pyridine-2-carboxylic acid (4-cyclopropyl-thiazol-2-yl)-amide in accordance with the general method of example 20 using 5-Bromopyrimidine instead of 3-bromopyridine to yield the final compound as a yellow solid, MS (ISP): m/e=352.1 (M+H+).

EXAMPLE 78

3-(3,5-Difluoro-phenylamino)-6-methyl-pyridine-2-carboxylic acid (4-cyclopropyl-thiazol-2-yl)-amide The title compound, was prepared from 3-Amino-6-methyl-pyridine-2-carboxylic acid (4-cyclopropyl-thiazol-2-yl)-amide in accordance with the general method of example 20 using 1-Bromo-3,5-difluorobenzene instead of 3-bromopyridine to yield the final compound as a yellow solid, MS (ISP): m/e=387.4 (M+H+).

EXAMPLE 79

6-Methyl-3-(1-methyl-1H-pyrazol-3-ylamino)-pyridine-2-carboxylic acid (1-methyl-1H-pyrazol-3-yl)-amide Step 1: 3-Bromo-6-methyl-pyridine-2-carboxylic acid ethyl ester:

To an ice cooled solution of 6.5 g (0.055 mol) tert-Butylnitrite and 9.8 g (0.044 mol) of Copper(II)bromide in 80 ml of Acetonitrile were added 6.6 g (0.037 mol) of (3-Bromo-6-methyl-pyridine-2-carboxylic acid ethyl ester (example 4). After stirring for 3 h, the brown reaction mixture was concentrated in vaccuo, 50 ml of saturated Ammonium chloride solution were added and the resulting aqueous phase was extracted twice with ethyl acetate. The combined organic phases were dried over magnesium sulfate, filtered and concentrated in vaccuo. Concentration in vaccuo yielded 8.2 g of an orange oil which was purified by flash chromatography on silicagel (heptane/ethyl acetate 4:1) to yield the title compound as a light yellow oil (6.82 g, 76%), MS (ISP): m/e=244.2, 246.1 (M+H+).

Step 2: 3-Bromo-6-methyl-pyridine-2-carboxylic acid (1-methyl-1H-pyrazol-3-yl)-amide:

To a solution 3-Amino-1-methyl-pyrazole (1.39 g, 14.3 mmol, 3.5 equiv.) in 25 ml of dry dioxane were added 7.17 ml of a 2M solution of trimethyl aluminium in hexane (14.3 mmol, 3.5 equiv.) and the mixture was stirred for 1 h at r.t. Then 3-Bromo-6-methyl-pyridine-2-carboxylic acid ethyl ester (1.00 g, 4.1 mmol) were added and the reaction was refluxed for 2 h. After allowing the reaction to cool to r.t., the reaction was quenched with water (0.5 ml), stirred for 10 min, dried by addition of magnesium sulfate and filtered over Dicalite which was further washed with methylene chloride. The filtrate was concentrated in vaccuo. The residue (1.66 g, yellow oil) was purified by flash chromatography (heptane/ethyl acetate 2:3) to yield the title compound as a yellow solid (total 0.99 g, 82%), MS (ISP): m/e=295.2, 297.2 (M+H+).

Step 3: 6-Methyl-3-(1-methyl-1H-pyrazol-3-ylamino)-pyridine-2-carboxylic acid (1-methyl-1H-pyrazol-3-yl)-amide:

In a 10 ml reaction vessel were dissolved 60 mg (0.203 mmol) 3-Bromo-6-methyl-pyridine-2-carboxylic acid (1-methyl-1H-pyrazol-3-yl)-amide and 25 mg (0.254 mmol, 1.5 equiv.) of 3-Amino-1-methyl-pyrazole in 4 ml of dioxane. Cesium carbonate (93 mg, 0.285 mmol, 1.4 equiv.) were added and argon was bubbled through the suspension for 3 min. Then Xanthphos (39 mg, 0.067 mmol, 0.33 equiv.) and $Pd_2(dba)_3 \cdot CHCl_3$ (21 mg, 0.020 mmol, 0.1 equiv.) were added. The vessel was closed and the mixture was heated overnight at 130° C. To the mixture was added silicagel (5 g) and the mixture was evaporated to dryness in vaccuo. The powder was charged onto a silicagel flash chromatography column and eluted (gradient 100% heptane to 100% ethyl acetate) to yield the title compound as a yellow solid (total 11 mg, 17%), MS (ISP): m/e=312.1 (M+H+).

EXAMPLE 80

3-(4-Fluoro-phenylamino)-6-methyl-pyridine-2-carboxylic acid (1-methyl-1H-pyrazol-3-yl)-amide The title compound, was prepared from 3-Bromo-6-methyl-pyridine-2-carboxylic acid (1-methyl-1H-pyrazol-3-yl)-amide in accordance with the general method of Example 78, step 3 using 4-Fluoroaniline instead of 3-Amino-1-methyl-pyrazole to yield the final compound as a yellow solid, MS (ISP): m/e=326.1 (M+H+).

EXAMPLE 81

6-Methyl-3-(4-methyl-thiazol-2-ylamino)-pyridine-2-carboxylic acid (1-methyl-1H-pyrazol-3-yl)-amide The title compound, was prepared from 3-Bromo-6-methyl-pyridine-2-carboxylic acid (1-methyl-1H-pyrazol-3-yl)-amide in accordance with the general method of Example 78, step 3 using 2-Amino-4-methylthiazole instead of 3-Amino-1-methyl-pyrazole to yield the final compound as a yellow solid, MS (ISP): m/e=329.1 (M+H+).

EXAMPLE 82

6-Methyl-3-(pyrazin-2-ylamino)-pyridine-2-carboxylic acid (1-methyl-1H-pyrazol-3-yl)-amide The title compound, was prepared from 3-Bromo-6-methyl-pyridine-2-carboxylic acid (1-methyl-1H-pyrazol-3-yl)-amide in accordance with the general method of Example 78, step 3 using Aminopyrazine instead of 3-Amino-1-methyl-pyrazole to yield the final compound as a yellow solid, MS (ISP): m/e=310.3 (M+H+).

EXAMPLE 83

6-Methyl-3-(2-methyl-2H-pyrazol-3-ylamino)-pyridine-2-carboxylic acid (1-methyl-1H-pyrazol-3-yl)-amide The title compound, was prepared from 3-Bromo-6-methyl-pyridine-2-carboxylic acid (1-methyl-1H-pyrazol-3-yl)-amide in accordance with the general method of Example 78, step 3 using 5-Amino-1-methyl-pyrazole instead of 3-Amino-1-methyl-pyrazole to yield the final compound as a yellow solid, MS (ISP): m/e=312.3 (M+H+).

EXAMPLE 84

6-Methyl-3-(1-methyl-1H-pyrazol-4-ylamino)-pyridine-2-carboxylic acid (1-methyl-1H-pyrazol-3-yl)-amide The title compound, was prepared from 3-Bromo-6-methyl-pyridine-2-carboxylic acid (1-methyl-1H-pyrazol-3-yl)-amide in accordance with the general method of Example 78, step 3 using 4-Amino-1-methyl-pyrazole instead of 3-Amino-1-methyl-pyrazole to yield the final compound as a yellow solid, MS (ISP): m/e=312.1 (M+H+).

EXAMPLE 85

3-(2,5-Dimethyl-2H-pyrazol-3-ylamino)-6-methyl-pyridine-2-carboxylic acid (1-methyl-1H-pyrazol-3-yl)-amide The title compound, was prepared from 3-Bromo-6-methyl-pyridine-2-carboxylic acid (1-methyl-1H-pyrazol-3-yl)-amide in accordance with the general method of Example 78, step 3 using 5-Amino-1,3-dimethylpyrazole instead of 3-Amino-1-methyl-pyrazole to yield the final compound as a yellow solid, MS (ISP): m/e=326.3 (M+H+).

EXAMPLE 86

6-Methyl-3-(6-methyl-pyrazin-2-ylamino)-pyridine-2-carboxylic acid (1-methyl-1H-pyrazol-3-yl)-amide The title compound, was prepared from 3-Bromo-6-methyl-pyridine-2-carboxylic acid (1-methyl-1H-pyrazol-3-yl)-amide in accordance with the general method of Example 78, step 3 using 2-Amino-6-methylpyrazine instead of 3-Amino-1-methyl-pyrazole to yield the final compound as a brown solid, MS (ISP): m/e=324.1 (M+H+).

EXAMPLE 87

6-Methyl-3-(4-methyl-pyrimidin-5-ylamino)-pyridine-2-carboxylic acid (1-methyl-1H-pyrazol-3-yl)-amide The title compound, was prepared from 3-Bromo-6-methyl-pyridine-2-carboxylic acid (1-methyl-1H-pyrazol-3-yl)-amide in accordance with the general method of Example 78, step 3 using 5-Amino-4-methylpyrimidine instead of 3-Amino-1-methyl-pyrazole to yield the final compound as a light yellow solid, MS (ISP): m/e=324.3 (M+H+).

EXAMPLE 88

3-(5-Fluoro-6-methyl-pyridin-2-ylamino)-6-methyl-pyridine-2-carboxylic acid (1-methyl-1H-pyrazol-3-yl)-amide The title compound, was prepared from 3-Bromo-6-methyl-pyridine-2-carboxylic acid (1-methyl-1H-pyrazol-3-yl)-amide in accordance with the general method of Example 78, step 3 using 2-Amino-5-fluoro-6-methylpyridine instead of 3-Amino-1-methyl-pyrazole to yield the final compound as a light yellow solid, MS (ISP): m/e=341 (M+H+).

EXAMPLE 89

3-(5-Chloro-pyridin-3-ylamino)-6-methyl-pyridine-2-carboxylic acid (1-methyl-1H-pyrazol-3-yl)-amide The title compound, was prepared from 3-Bromo-6-methyl-pyridine-2-carboxylic acid (1-methyl-1H-pyrazol-3-yl)-amide in accordance with the general method of Example 78, step 3 using 3-Amino-5-chloropyridine instead of 3-Amino-1-methyl-pyrazole to yield the final compound as a yellow solid, MS (ISP): m/e=343.0, 345.1 (M+H+).

EXAMPLE 90

6-Methyl-3-(2-methyl-2H-pyrazol-3-ylamino)-pyridine-2-carboxylic acid (4-methyl-thiazol-2-yl)-amide Step 1: 6-Methyl-3-(2-methyl-2H-pyrazol-3-ylamino)-pyridine-2-carboxylic acid ethyl ester:

The Pd catalyzed coupling of 3-Bromo-6-methyl-pyridine-2-carboxylic acid ethyl ester and 3-Amino-1-methyl-pyrazole was performed in accordance with the general method of Example 78, step 3 to yield the title compound as a red solid, MS (ISP): m/e=261.3 (M+H+).

Step 2: 6-Methyl-3-(2-methyl-2H-pyrazol-3-ylamino)-pyridine-2-carboxylic acid (4-methyl-thiazol-2-yl)-amide:

The title compound, was prepared in accordance with the general method of Example 78, step 2 from 6-Methyl-3-(2-methyl-2H-pyrazol-3-ylamino)-pyridine-2-carboxylic acid ethyl ester instead of 3-Bromo-6-methyl-pyridine-2-carboxylic acid ethyl ester and using 2-Amino-4-methylthiazole instead of 3-Amino-1-methyl-pyrazole to yield the final compound as a yellow solid, MS (ISP): m/e=329.1 (M+H+).

EXAMPLE 91

6-Methyl-3-(2-methyl-2H-pyrazol-3-ylamino)-pyridine-2-carboxylic acid (5-fluoro-pyridin-2-yl)-amide The title compound, was prepared from 6-Methyl-3-(2-methyl-2H-pyrazol-3-ylamino)-pyridine-2-carboxylic acid ethyl ester and 2-Amino-5-fluoropyridine in accordance with the general method of Example 78, step 2 to yield the final compound as a yellow crystalline solid, MS (ISP): m/e=327.0 (M+H+).

EXAMPLE 92

6-Methyl-3-(2-methyl-2H-pyrazol-3-ylamino)-pyridine-2-carboxylic acid (2-methyl-thiazol-4-yl)-amide The title compound, was prepared from 6-Methyl-3-(2-methyl-2H-pyrazol-3-ylamino)-pyridine-2-carboxylic acid ethyl ester in accordance with the general method of example 75, step 2 using 4-Amino-2-methylthiazole instead of 3-Amino-1-methyl-pyrazole to yield the final compound as a light brown solid, MS (ISP): m/e=329.1 (M+H+).

EXAMPLE 93

6-Methyl-3-(1-methyl-1H-pyrazol-4-ylamino)-pyridine-2-carboxylic acid (4-methyl-thiazol-2-yl)-amide Step 1: 6-Methyl-3-(1-methyl-1H-pyrazol-4-ylamino)-pyridine-2-carboxylic acid ethyl ester:
The Pd catalyzed coupling of 3-Bromo-6-methyl-pyridine-2-carboxylic acid ethyl ester and 4-Amino-1-methyl-pyrazole was performed in accordance with the general method of Example 78, step 3 to yield the title compound as an orange solid, MS (ISP): m/e=261.0 (M+H+).

Step 2: 6-Methyl-3-(1-methyl-1H-pyrazol-4-ylamino)-pyridine-2-carboxylic acid (4-methyl-thiazol-2-yl)-amide:
The title compound, was prepared in accordance with the general method of Example 78, step 2 from 6-Methyl-3-(1-methyl-1H-pyrazol-4-ylamino)-pyridine-2-carboxylic acid ethyl ester and 2-Amino-4-methylthiazole to yield the final compound as a yellow solid, MS (ISP): m/e=329.3 (M+H+).

EXAMPLE 94

6-Methyl-3-(1-methyl-1H-pyrazol-4-ylamino)-pyridine-2-carboxylic acid (5-fluoro-pyridin-2-yl)-amide The title compound, was prepared from 6-Methyl-3-(1-methyl-1H-pyrazol-4-ylamino)-pyridine-2-carboxylic acid ethyl ester and 2-Amino-5-fluoropyridine in accordance with the general method of Example 78, step 2 to yield the final compound as a yellow crystalline solid, MS (ISP): m/e=327.1 (M+H+).

EXAMPLE 95

3-(2,5-Dimethyl-2H-pyrazol-3-ylamino)-6-methyl-pyridine-2-carboxylic acid (4-methyl-thiazol-2-yl)-amide Step 1: 3-(2,5-Dimethyl-2H-pyrazol-3-ylamino)-6-methyl-pyridine-2-carboxylic acid ethyl ester:
The Pd catalyzed coupling of 3-Bromo-6-methyl-pyridine-2-carboxylic acid ethyl ester and 5-Amino-1,3-dimethylpyrazole was performed in accordance with the general method of Example 78, step 3 to yield the title compound as a yellow-cristalline solid, MS (ISP): m/e=275.4 (M+H+).

Step 2: 3-(2,5-Dimethyl-2H-pyrazol-3-ylamino)-6-methyl-pyridine-2-carboxylic acid (4-methyl-thiazol-2-yl)-amide:
The title compound, was prepared in accordance with the general method of Example 78, step 2 from 3-(2,5-Dimethyl-2H-pyrazol-3-ylamino)-6-methyl-pyridine-2-carboxylic acid ethyl ester and 2-Amino-4-methylthiazole to yield the final compound as a yellow solid, MS (ISP): m/e=343.1 (M+H+).

EXAMPLE 96

6-Methyl-3-(1-methyl-1H-pyrazol-4-ylamino)-pyridine-2-carboxylic acid (5-fluoro-pyridin-2-yl)-amide The title compound, was prepared from 3-(2,5-Dimethyl-2H-pyrazol-3-ylamino)-6-methyl-pyridine-2-carboxylic acid ethyl ester and 2-Amino-5-fluoropyridine in accordance with the general method of Example 78, step 2 to yield the final compound as a yellow crystalline solid, MS (ISP): m/e=341.1 (M+H+).

EXAMPLE 97

3-(2,5-Dimethyl-2H-pyrazol-3-ylamino)-6-methyl-pyridine-2-carboxylic acid (2-methyl-thiazol-4-yl)-amide The title compound, was prepared from 3-(2,5-Dimethyl-2H-pyrazol-3-ylamino)-6-methyl-pyridine-2-carboxylic acid ethyl ester and 4-Amino-2-methylthiazole in accordance with the general method of Example 78, step 2 to yield the final compound as a light-yellow solid, MS (ISP): m/e=343.0 (M+H+).

EXAMPLE 98

6-Methyl-3-(5-methyl-pyridin-3-ylamino)-pyridine-2-carboxylic acid (1-methyl-1H-pyrazol-3-yl)-amide Step 1: 6-Methyl-3-(5-methyl-pyridin-3-ylamino)-pyridine-2-carboxylic acid ethyl ester:
The Pd catalyzed coupling of 3-Bromo-6-methyl-pyridine-2-carboxylic acid ethyl ester and 3-Amino-5-methylpyridine was performed in accordance with the general method of Example 78, step 3 to yield the title compound as a light brown solid, MS (ISP): m/e=272.3 (M+H+).

Step 2: 3-(2,5-Dimethyl-2H-pyrazol-3-ylamino)-6-methyl-pyridine-2-carboxylic acid (4-methyl-thiazol-2-yl)-amide:
The title compound, was prepared in accordance with the general method of Example 78, step 2 from 6-Methyl-3-(5-methyl-pyridin-3-ylamino)-pyridine-2-carboxylic acid ethyl ester and 3-Amino-1-methylpyrazole to yield the final compound as a yellow solid, MS (ISP): m/e=323.3 (M+H+).

EXAMPLE 99

6-Methyl-3-(5-methyl-pyridin-3-ylamino)-pyridine-2-carboxylic acid (4-methyl-thiazol-2-yl)-amide The title compound, was prepared from 6-Methyl-3-(5-methyl-pyridin-3-ylamino)-pyridine-2-carboxylic acid ethyl ester and 2-Amino-4-methylthiazole in accordance with the general method of Example 78, step 2 to yield the final compound as a yellow solid, MS (ISP): m/e=340.3 (M+H+).

EXAMPLE 100

6-Methyl-3-(5-methyl-pyridin-3-ylamino)-pyridine-2-carboxylic acid (2-methyl-thiazol-4-yl)-amide The title compound, was prepared from 6-Methyl-3-(5-methyl-pyridin-3-ylamino)-pyridine-2-carboxylic acid ethyl ester and 4-Amino-2-methylthiazole in accordance with the general method of Example 78, step 2 to yield the final compound as a light-yellow solid, MS (ISP): m/e=340.1 (M+H+).

EXAMPLE 101

3-(5-Cyclopropyl-2-methyl-2H-pyrazol-3-ylamino)-6-methyl-pyridine-2-carboxylic acid (1-methyl-1H-pyrazol-3-yl)-amide Step 1: 3-(5-Cyclopropyl-2-methyl-2H-pyrazol-3-ylamino)-6-methyl-pyridine-2-carboxylic acid ethyl ester:

The Pd catalyzed coupling of 3-Bromo-6-methyl-pyridine-2-carboxylic acid ethyl ester and 5-Amino-3-cyclopropyl-1-methylpyrazole was performed in accordance with the general method of Example 78, step 3 to yield the title compound as an orange solid, MS (ISP): m/e 301.4 (M+H+).

Step 2: 3-(2,5-Dimethyl-2H-pyrazol-3-ylamino)-6-methyl-pyridine-2-carboxylic acid (4-methyl-thiazol-2-yl)-amide The title compound, was prepared in accordance with the general method of Example 78, step 2 from 3-(5-Cyclopropyl-2-methyl-2H-pyrazol-3-ylamino)-6-methyl-pyridine-2-carboxylic acid ethyl ester and 3-Amino-1-methylpyrazole to yield the final compound as a yellow solid, MS (ISP): m/e=352.3 (M+H+).

EXAMPLE 102

3-(5-Cyclopropyl-2-methyl-2H-pyrazol-3-ylamino)-6-methyl-pyridine-2-carboxylic acid (4-methyl-thiazol-2-yl)-amide The tide compound, was prepared from 3-(5-Cyclopropyl-2-methyl-2H-pyrazol-3-ylamino)-6-methyl-pyridine-2-carboxylic acid ethyl ester and 2-Amino-4-methylthiazole in accordance with the general method of Example 78, step 2 to yield the final compound as a yellow solid, MS (ISP): m/e=369.0 (M+H+).

EXAMPLE 103

3-(5-Cyclopropyl-2-methyl-2H-pyrazol-3-ylamino)-6-methyl-pyridine-2-carboxylic acid (5-fluoro-6-methyl-pyridin-2-yl)-amide The title compound, was prepared from 3-(5-Cyclopropyl-2-methyl-2H-pyrazol-3-ylamino)-6-methyl-pyridine-2-carboxylic acid ethyl ester and 2-Amino-5-fluoro-6-methylpyridine in accordance with the general method of Example 78, step 2 to yield the final compound as a yellow cristalline solid, MS (ISP): m/e=381.4 (M+H+).

EXAMPLE 104

3-(5-Cyclopropyl-2-methyl-2H-pyrazol-3-ylamino)-6-methyl-pyridine-2-carboxylic acid (5-fluoro-pyridin-2-yl)-amide The tide compound, was prepared from 3-(5-Cyclopropyl-2-methyl-2H-pyrazol-3-ylamino)-6-methyl-pyridine-2-carboxylic acid ethyl ester and 2-Amino-5-fluoropyridine in accordance with the general method of Example 78, step 2 to yield the final compound as a yellow cristalline solid, MS (ISP): m/e=367.3 (M+H+).

EXAMPLE 105

6-Methyl-3-(pyrimidin-5-ylamino)-pyridine-2-carboxylic acid (4-methyl-thiazol-2-yl)-amide Step 1: 6-Methyl-3-(pyrimidin-5-ylamino)-pyridine-2-carboxylic acid ethyl ester:

The Pd catalyzed coupling of 3-Bromo-6-methyl-pyridine-2-carboxylic acid ethyl ester and 5-Amino-pyrimidine (CAS:[591-55-9] (J. Org. Chem., 20, 829 (1955)) was performed in accordance with the general method of Example 78, step 3 to yield the tide compound as a light brown solid, MS (ISP): m/e=259.3 (M+H+).

Step 2: 6-Methyl-3-(pyrimidin-5-ylamino)-pyridine-2-carboxylic acid (4-methyl-thiazol-2-yl)-amide:

The title compound, was prepared in accordance with the general method of Example 78, step 2 from 6-Methyl-3-(pyrimidin-5-ylamino)-pyridine-2-carboxylic acid ethyl ester and 2-amino-4-methylthiazole to yield the final compound as an off-white solid, MS (ISP): m/e=327.1 (M+H+).

EXAMPLE 106

6-Methyl-3-(pyrimidin-5-ylamino)-pyridine-2-carboxylic acid (5-methyl-thiazol-2-yl)-amide The title compound, was prepared in accordance with the general method of Example 78, step 2 from 6-Methyl-3-(pyrimidin-5-ylamino)-pyridine-2-carboxylic acid ethyl ester and 2-Amino-5-methylthiazole to yield the final compound as a yellow crystalline solid, MS (ISP): m/e=327.1 (M+H+).

EXAMPLE 107

6-Methyl-3-(pyridin-3-ylamino)-pyridine-2-carboxylic acid (5-methyl-thiazol-2-yl)-amide Step 1: 6-Methyl-3-(pyridin-3-ylamino)-pyridine-2-carboxylic acid ethyl ester:

The Pd catalyzed coupling of 3-Bromo-6-methyl-pyridine-2-carboxylic acid ethyl ester and 3-Amino-pyridine was performed in accordance with the general method of Example 78, step 3 to yield the title compound as a light yellow crystalline solid, MS (ISP): m/e=258.1 (M+H+).

Step 2: 6-Methyl-3-(pyridin-3-ylamino)-pyridine-2-carboxylic acid (5-methyl-thiazol-2-yl)-amide:

The title compound, was prepared from 6-Methyl-3-(pyridin-3-ylamino)-pyridine-2-carboxylic acid ethyl ester and 2-Amino-5-methylthiazole in accordance with the general method of example 78, step 2 to yield the final compound as a yellow crystalline solid, MS (ISP): m/e=326.1 (M+H+).

EXAMPLE 108

6-Methyl-3-(pyrimidin-5-ylamino)-pyridine-2-carboxylic acid (4-hydroxymethyl-thiazol-2-yl)-amide Step 1: 6-Methyl-3-(pyrimidin-5-ylamino)-pyridine-2-carboxylic acid [4-(tert-butyl-dimethyl-silanyloxymethyl)-thiazol-2-yl]-amide The Al(Me)$_3$-catalyzed reaction of 6-Methyl-3-(pyrimidin-5-ylamino)-pyridine-2-carboxylic acid ethyl ester and 4-(tert-Butyl-dimethyl-silanyloxymethyl)-thiazol-2-ylamine (CAS [752241-92-2]; WO2004076420) in accordance with the general method of Example 78, step 2 yielded the title compound as an off-white solid, MS (ISP): m/e=457.3 (M+H+).

Step 2: 6-Methyl-3-(pyrimidin-5-ylamino)-pyridine-2-carboxylic acid (4-hydroxymethyl-thiazol-2-yl)-amide:

To a solution of 40 mg (0.088 mmol) of 6-Methyl-3-(pyrimidin-5-ylamino)-pyridine-2-carboxylic acid [4-(tert-butyl-dimethyl-silanyloxymethyl)-thiazol-2-yl]-amide in 1 ml of methylene chloride was added 200 mg (1.75 mmol, 20.0 equiv.) of Trifluoroacetic acid. After stirring for 2 h at room temperature, saturated sodium carbonate solution was added, and the pH was adjusted to 8. The aqueous phase was extracted three times with methylene chloride. The combined organic phases were dried over magnesium sulfate, filtered and concentrated in vaccuo. The residue (28 mg, yellow solid) was triturated with Diisopropyl ether, filtered and dried to yield the title compound (17 mg, 57%) as a light yellow solid, MS (ISP): m/e=343.1 (M+H+).

EXAMPLE 109

6-Hydroxymethyl-3-(pyrimidin-5-ylamino)-pyridine-2-carboxylic acid (4-methyl-thiazol-2-yl)-amide The title compound, was prepared 6-(tert-Butyl-dimethyl-silanyloxymethyl)-3-(pyrimidin-5-ylamino)-pyridine-2-carboxylic acid (4-methyl-thiazol-2-yl)-amide was deprotected with Trifluoroacetic acid in accordance with the general method of example 105, step 2, yielded the final compound as a light yellow solid, MS (ISP): m/e=343.3 (M+H+). The 6-(tert-Butyl-dimethyl-silanyloxymethyl)-3-(pyrimidin-5-ylamino)-pyridine-2-carboxylic acid (4-methyl-thiazol-2-yl)-amide used in the above described example was synthesized as follows:

Step 1: 3-tert-Butoxycarbonylamino-6-methyl-1-oxy-pyridine-2-carboxylic acid ethyl ester:

A solution of 2.00 g (7.1 mmol) 3-tert-Butoxycarbonylamino-6-methyl-pyridine-2-carboxylic acid ethyl ester and 4.93 g (28.6 mmol, 4.0 equiv.) of m-Chloroperbenzoic acid in 200 ml of methylene chloride was stirred for 3 days at room temperature. The reaction mixture was poured into 200 ml of 5% bicarbonate solution. The organic phase was separated. The aqueous phase was extracted three times with 50 ml of methylene chloride. The combined organic phases were dried over magnesium sulfate and concentrated to yield 3.8 g of a light yellow solid, which after purification by chromatography on silicagel with ethyl acetate as eluent yielded 1.47 g (5.0 mmol, 70%) of the title compound as an off-white solid, MS (ISP): m/e=297.4 (M+H+).

Step 2: 6-Acetoxymethyl-3-tert-butoxycarbonylamino-pyridine-2-carboxylic acid ethyl ester:

A solution of 1.47 g of 3-tert-Butoxycarbonylamino-6-methyl-1-oxy-pyridine-2-carboxylic acid ethyl ester in 36 ml of acetic anhydride was stirred for 2 h at 120° C. After evaporation of the solvent in vaccuo, the residue was purified by flash chromatography on silicagel (heptane/ethyl acetate 3:1 v/v) to yield 0.99 g (2.92 mmol, 59%) of the title compound as a white solid, MS (ISP): m/e=339.3 (M+H+).

Step 3: 3-tert-Butoxycarbonylamino-6-hydroxymethyl-pyridine-2-carboxylic acid ethyl ester:

To a solution of 0.99 g (2.92 mmol) of 6-Acetoxymethyl-3-tert-butoxycarbonylamino-pyridine-2-carboxylic acid ethyl ester in 15 ml of absolute ethanol was added 0.11 ml (0.3 mmol, 0.1 equiv.) of sodium ethylate 3N /Ethanol. After stirring for 1 h at room temperature, the mixture was extracted with methylene chloride/water. The aqueous phase was extracted three times with methylene chloride. The combined organic phases were dried over magnesium sulfate and concentrated to yield 0.81 g (2.7 mmol, 93%) of the title compound as an off-white solid, MS (ISP): m/e=297.3 (M+H+).

Step 4: 3-tert-Butoxycarbonylamino-6-(tert-butyl-dimethyl-silanyloxymethyl)-pyridine-2-carboxylic acid ethyl ester:

To a solution of 0.81 g (2.7 mmol) 3-tert-Butoxycarbonylamino-6-hydroxymethyl-pyridine-2-carboxylic acid ethyl ester and 1.11 g (16 mmol, 6.0 equiv.) of imidazole in 5 ml of DMF were added 0.90 g (6.0 mmol, 2.2 equiv.) of tert-butyldimethylchlorosilane. The solution was stirred overnight at room temperature. After extraction with ethyl acetate/water and purification by flash chromatography over silicagel (heptane/ethyl acetate 4:1 v/v), one obtains 0.69 g (1.7 mmol, 61%) of the title compound as a colorless oil, MS (ISP): m/e=411.3 (M+H+).

Step 5: 3-Amino-6-(tert-butyl-dimethyl-silanyloxyrethyl)-pyridine-2-carboxylic acid (4-methyl-thiazol-2-yl)-amide The Al(Me)$_3$-catalyzed reaction of 0.53 g (1.29 mmol) of 3-tert-Butoxycarbonylamino-6-(tert-butyl-dimethyl-silanyloxymethyl)-pyridine-2-carboxylic acid ethyl ester and 2-amino-4-methyl thiazole in accordance with the general method of Example 78, step 2 yielded 0.58 g of crude [6-Hydroxymethyl-2-(4-methyl-thiazol-2-ylcarbamoyl)-pyridin-3-yl]-carbamic acid tert-butyl ester (which also contains 2-amino-4-methyl thiazole) as a dark brown oil, MS (ISP): m/e=365.1 (M+H+). This crude material was dissolved in 4 ml of methylene chloride and 2.4 ml of trifluoroacetic acid. The solution was stirred overnight at room temperature. The pH of the solution was adjusted to 8 by addition of saturated sodium carbonate solution and extracted three times with methylene chloride. The combined organic phases were dried over magnesium sulfate and concentrated to yield 0.47 g of 3-Amino-6-hydroxymethyl-pyridine-2-carboxylic acid (4-methyl-thiazol-2-yl)-amide as a dark brown oil (containing 2-amino-4-methyl thiazole), MS (ISP): m/e=265.3 (M+H+). The crude material was reprotected with tert-butyldimethylchlorosilane/imidazole according to the general procedure described in step 4 to yield, after extraction and purification, 88 mg (0.23 mmol, 13%) of the pure title compound as a light yellow solid, MS (ISP): m/e=379.3 (M+H+).

Step 6: 6-(tert-Butyl-dimethyl-silanyloxymethyl)-3-(pyrimidin-5-ylamino)-pyridine-2-carboxylic acid (4-methyl-thiazol-2-yl)-amide:

Palladium catalysed arylation of 3-Amino-6-(tert-butyl-dimethyl-silanyloxymethyl)-pyridine-2-carboxylic acid (4-methyl-thiazol-2-yl)-amide with 5-Bromopyrimidine according to the general procedure described in example 4 step 4 yielded the title product as a light yellow solid, MS (ISP): m/e=457.3 (M+H+).

EXAMPLE 110

6-Cyclopropyl-3-(pyrimidin-5-ylamino)-pyridine-2-carboxylic acid (1-methyl-1H-pyrazol-3-yl)-amide The title compound, was prepared from 3-Amino-6-cyclopropyl-pyridine-2-carboxylic acid (1-methyl-1H-pyrazol-3-yl)-amide and 5-bromopyrimidine in accordance with the general method of example 4 using to yield the final compound as a yellow crystalline solid, MS (ISP): m/e=336.1 (M+H+).

The 3-Amino-6-cyclopropyl-pyridine-2-carboxylic acid (1-methyl-1H-pyrazol-3-yl)-amide used in the above described example was synthesized as follows:

Step 1: 3-tert-Butoxycarbonylamino-pyridine-2-carboxylic acid ethyl ester:

The title compound, was prepared from Pyridine-2,3-dicarboxylic acid 2-ethyl ester (CAS[161522-42-5], J.Med. Chem. 38(3), 496(1995)) in accordance with the general method of example 4, step 1 to yield the final compound as a white crystalline solid, MS (ISP): m/e=267.4 (M+H+).

Step 2: 3-Amino-pyridine-2-carboxylic acid ethyl ester:

Deprotection of the Boc group according to the procedure described in example 4 step 3 yielded the tidle compound as a cristalline white solid, MS (ISP): m/e=167.4 (M+H+).

Step 3: 3-Amino-6-bromo-pyridine-2-carboxylic acid ethyl ester:

A solution of 2.00 g (12.04 mmol) 3-Amino-pyridine-2-carboxylic acid ethyl ester and 2.57 g (14.44 mmol, 1.2 equiv.) of N-Bromosuccinimide in 80 ml of acetonitrile was stirred for 2 h at room temperature. Silicagel (5 g) was added to the reaction mixture Which was evaporated to dryness. The residue was loaded onto a Flash chromatography column (SiO$_2$, 50 g) and eluted with heptane/ethyl acetate 3:1. One obtains 1.11 g (4.51 mmol, 37%) of the title compound as a white cristalline solid, MS (ISP): m/e=245.1, 247.1 (M+H+).

Step 4: 6-Bromo-3-bis(tert-butoxycarbonylamino)-pyridine-2-carboxylic acid ethyl ester:

A solution of 1.075 g (4.39 mmol) 3-Amino-6-bromo-pyridine-2-carboxylic acid ethyl ester, 2.01 g (9.21 mmol, 2.1 equiv.) Di-tert-butyldicarbonate, and 21 mg (0.04 mmol) of 4-N,N-dimethylaminopyridine (DMAP) in 40 ml of methylene chloride was stirred overnight at room temperature. After extraction with methylene chloride/water and purification by Flash chromatography (SiO2, 70 g, gradient heptane->heptane/ethyl acetate 15%) on obtains 1.68 g (3.77 mol, 86%) of the title compound as a white cristalline solid, MS (ISP): m/e=445.2, 447.0 (M+H+).

Step 5: 6-Cyclopropyl-3-bis(tert-butoxycarbonylamino)-pyridine-2-carboxylic acid ethyl ester:

To a degassed solution of 0.500 g (1.12 mmol) of 6-Bromo-3-bis(tert-butoxycarbonyl-amino)-pyridine-2-carboxylic acid ethyl ester in 4 ml of absolute THF was added 7.0 ml of an 0.4 M solution of Cyclopropylzinc chloride (CAS: [203861-73-8])in THF, and 19.5 mg (0.017 mmol, 0.1 equiv.) of Tetrakis(triphenylphosphine) Palladium. After heating the mixture for 2.5 h at 70° C. under an Argon atmosphere, the mixture was extracted with Ethyl acetate water, dried over Magnesium sulfate, and purified by Flash chromatography (SiO$_2$, Heptane/Ethyl acetate 5:1) to yield the title compound as a colorless oil, MS (ISP): m/e=407.4 (M+H+).

Step 6: [6-Cyclopropyl-2-(1-methyl-1H-pyrazol-3-ylcarbamoyl)-pyridin-3-yl]-carbamic acid tert-butyl ester:

The Al(Me)$_3$-catalyzed reaction of 6-Cyclopropyl-3-bis(tert-butoxycarbonylamino)-pyridine-2-carboxylic acid ethyl ester and 3-Amino-1-methylpyrazole in accordance with the general method of Example 78, step 2, yielded, with concomitant loss of one Boc group, the title compound as a white cristalline solid, MS (ISP): m/e=358.3 (M+H+).

Step 7: 3-Amino-6-cyclopropyl-pyridine-2-carboxylic acid (1-methyl-1H-pyrazol-3-yl)-amide:

A solution of 70 mg (0.228 mmol) of [6-Cyclopropyl-2-(1-methyl-1H-pyrazol-3-ylcarbamoyl)-pyridin-3-yl]-carbamic acid tert-butyl ester in 3 ml of methylene chloride was treated with 0.26 ml (0.39 g, 3.42 mmol, 15 equiv.) of trifluoroacetic acid. After stirring for 2.5 h at room temperature, the mixture was worked up with Ethyl acetate/Sodium bicarbonate/water to yield 49 mg (0.19 mmol, 83%) of crude title compound as a light yellow solid, MS (ISP): m/e=258.1 (M+H+); which was sufficiently pure to be used directly in the next step.

EXAMPLE 111

6-Cyclopropyl-3-(pyridin-3-ylamino)-pyridine-2-carboxylic acid (1-methyl-1H-pyrazol-3-yl)-amide The Al(Me)$_3$-catalyzed reaction of 6-Cyclopropyl-3-(pyridin-3-ylamino)-pyridine-2-carboxylic acid ethyl ester and 3-Amino-1-methylpyrazole in accordance with the general method of Example 78, step 2 yielded the title compound as a light yellow cristalline solid, MS (ISP): m/e=335.4 (M+H+).

The 6-Cyclopropyl-3-(pyridin-3-ylamino)-pyridine-2-carboxylic acid ethyl ester used in the above described example was synthesized as follows:

Step 1: 3-Amino-6-cyclopropyl-pyridine-2-carboxylic acid ethyl ester:

Deprotection of 6-Cyclopropyl-3-bis(tert-butoxycarbonylamino)-pyridine-2-carboxylic acid ethyl ester with trifluoroacetic acid according to the procedure described in example 106, step 7 yielded the title compound as a light yellow cristalline solid, MS (ISP): m/e=207.3 (M+H+).

Step 2: 3-Bromo-6-cyclopropyl-pyridine-2-carboxylic acid ethyl ester:

Sandmeyer reaction of 3-Amino-6-cyclopropyl-pyridine-2-carboxylic acid ethyl ester according to the procedure described in example 78, step 1 yielded the title compound as a colorless oil, MS (ISP): m/e=270.2, 272.2 (M+H+).

Step 3: 6-Cyclopropyl-3-(pyridin-3-ylamino)-pyridine-2-carboxylic acid ethyl ester:

Palladium catalysed arylation of 3-Bromo-6-cyclopropyl-pyridine-2-carboxylic acid ethyl ester with 3-Aminopyridine according to the general procedure described in example 78 step 3 yielded the title compound as a light yellow solid, MS (ISP): m/e=284.4 (M+H+).

EXAMPLE 112

6-Cyclopropyl-3-(pyridin-3-ylamino)-pyridine-2-carboxylic acid (4-methyl-thiazol-2-yl)-amide The Al(Me)$_3$-catalyzed reaction of 6-Cyclopropyl-3-(pyridin-3-ylamino)-pyridine-2-carboxylic acid ethyl ester and 2-Amino-4-methyl-thiazole in accordance with the general method of Example 78, step 2 yielded the title compound as a yellow cristalline solid, MS (ISP): m/e=352.1 (M+H+).

EXAMPLE 113

6-Ethyl-3-(pyrimidin-5-ylamino)-pyridine-2-carboxylic acid (4-methyl-thiazol-2-yl)-amide The Al(Me)$_3$-catalyzed reaction of 6-Ethyl-3-(pyrimidin-5-ylamino)-pyridine-2-carboxylic acid ethyl ester and 2-Amino-4-methyl-thiazole in accordance with the general method of Example 78, step 2 yielded the title compound as a yellow cristalline solid, MS (ISP): m/e=340.9 (M+H+).

The 6-Ethyl-3-(pyrimidin-5-ylamino)-pyridine-2-carboxylic acid ethyl ester used in the above described example was synthesized as follows:

Step 1: 6-Ethyl-3-bis(tert-butoxycarbonylamino)-pyridine-2-carboxylic acid ethyl ester:

Palladium catalysed coupling of 6-Bromo-3-bis(tert-butoxycarbonyl-amino)-pyridine-2-carboxylic acid ethyl ester (example 107, step 4) according to the procedure described in example 107, step 5 using Diethylzinc instead of Cyclopropylzinc chloride yielded the title compound as a yellow oil, MS (ISP): m/e=395.1 (M+H+).

Step 2: 3-Amino-6-ethyl-pyridine-2-carboxylic acid ethyl ester:

Boc deprotection of 6-Ethyl-3-bis(tert-butoxycarbonylamino)-pyridine-2-carboxylic acid ethyl ester with Trifluoroacetic acid according to the procedure described in example 107, step 7 yielded the title compound as a light brown solid, MS (ISP): m/e=195.1 (M+H+).

Step 3: 3-Bromo-6-ethyl-pyridine-2-carboxylic acid ethyl ester:

Sandmeyer reaction of 3-Amino-6-ethyl-pyridine-2-carboxylic acid ethyl ester according to the procedure described in example 78, step 1 yielded the title compound as a colorless oil, MS (ISP): m/e=258.0, 260.0 (M+H+).

Step 4: 6-Ethyl-3-(pyrimidin-5-ylamino)-pyridine-2-carboxylic acid ethyl ester:

Palladium catalysed arylation of 3-Bromo-6-cyclopropyl-pyridine-2-carboxylic acid ethyl ester with 5-Aminopyrimidine according to the general procedure described in example 78 step 3 yielded the title compound as a white solid, MS (ISP): m/e=273.3 (M+H+).

Preparation of Pharmaceutical Compositions Comprising Compounds of the Invention:

EXAMPLE I

Tablets of the following composition are produced in a conventional manner:

|  | mg/Tablet |
| --- | --- |
| Active ingredient | 100 |
| Powdered. lactose | 95 |
| White corn starch | 35 |
| Polyvinylpyrrolidone | 8 |
| Na carboxymethylstarch | 10 |
| Magnesium stearate | 2 |
| Tablet weight | 250 |

EXAMPLE II

Tablets of the following composition are produced in a conventional manner:

|  | mg/Tablet |
| --- | --- |
| Active ingredient | 200 |
| Powdered. lactose | 100 |
| White corn starch | 64 |
| Polyvinylpyrrolidone | 12 |
| Na carboxymethylstarch | 20 |
| Magnesium stearate | 4 |
| Tablet weight | 400 |

EXAMPLE III

Capsules of the following composition are produced:

|  | mg/Capsule |
| --- | --- |
| Active ingredient | 50 |
| Crystalline. lactose | 60 |
| Microcrystalline cellulose | 34 |
| Talc | 5 |
| Magnesium stearate | 1 |
| Capsule fill weight | 150 |

The active ingredient having a suitable particle size, the crystalline lactose and the microcrystalline cellulose are homogeneously mixed with one another, sieved and thereafter talc and magnesium stearate are admixed. The final mixture is filled into hard gelatine capsules of suitable size.

What is claimed is:

1. A compound of formula (Ib):

(Ib)

wherein
$R^2$ is H, $C_1$-$C_7$-alkyl, $C_3$-$C_6$-cycloalkyl, or —$(CH_2)_m$—$R^a$;
$R^3$ is aryl or a 5- or 6-membered heteroaryl each of which is optionally substituted by:
CN, Cl, F, Br, $CF_3$, $CHF_2$, —O—$C_1$-$C_7$-alkyl, —(CO)—$R^b$, —$(CH_2)_m$—$R^c$, —NH—(CO)—$C_1$-$C_7$-alkyl, —O—$CH_2$F, —O—$CHF_2$, —O—$CF_3$, —$S(O)_2$-$R^d$, $C_3$-$C_6$-cycloalkyl, or heteroaryl which is optionally substituted by $C_1$-$C_7$-alkyl; and
$R^4$ is H, —OH, Cl, F, Br, CN, —$CHF_2$, $CF_3$, $C_1$-$C_7$-alkyl, —O—(CO)—$C_1$-$C_7$-alkyl, $C_3$-$C_6$-cycloalkyl, or —$(CH_2)_m$—$R^e$;
or a pharmaceutically acceptable salt thereof.

2. The compound of claim 1, wherein:
$R^2$ is H or $C_1$-$C_7$-alkyl;
$R^3$ is phenyl or a 5- or 6-membered heteroaryl each of which is optionally substituted by:
CN, Cl, F, Br, $CF_3$, $CHF_2$, —O—$C_1$-$C_7$-alkyl, —(CO)—$R^b$, —$(CH_2)_m$—$R^c$, —NH—(CO)—$C_1$-$C_7$-alkyl, —O—$CH_2$F, —O—$CHF_2$, —O—$CF_3$, —$S(O)_2$—$R^d$, or heteroaryl which is optionally substituted by $C_1$-$C_7$-alkyl; and R⁴ is H, —OH, Cl, F, Br, CN, —CHF₂, CF₃, C₁-C₇-alkyl, —O—(CO)—C₁-C₇-alkyl, or —(CH₂)ₘ—Rᵉ or a pharmaceutically acceptable salt thereof.

3. The compound of claim 2, selected from the group consisting of:
  6-Methyl-3-(pyrimidin-5-ylamino)-pyridine-2-carboxylic acid (2-methyl-thiazol-4-yl)-amide;
  6-Methyl-3-(pyridin-3-ylamino)-pyridine-2-carboxylic acid (2-methyl-thiazol-4-yl)-amide;
  3-(5-Fluoro-pyridin-3-ylamino)-6-methyl-pyridine-2-carboxylic acid (2-methyl-thiazol-4-yl)-amide;
  6-Methyl-3-(2-methyl-2H-pyrazol-3-ylamino)-pyridine-2-carboxylic acid (2-methyl-thiazol-4-yl)-amide;
  3-(2,5-Dimethyl-2H-pyrazol-3-ylamino)-6-methyl-pyridine-2-carboxylic acid (2-methyl-thiazol-4-yl)-amide; and
  6-Methyl-3-(5-methyl-pyridin-3-ylamino)-pyridine-2-carboxylic acid (2-methyl-thiazol-4-yl)-amide.

4. A compound of formula (Ic):

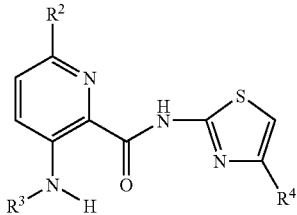

(Ic)

wherein
R² is H, C₁-C₇-alkyl, C₃-C₆-cycloalkyl, or —(CH₂)ₘ—Rᵃ;
R³ is aryl or a 5- or 6-membered heteroaryl each of which is optionally substituted by:
  CN, Cl, F, Br, CF₃, CHF₂, —O—C₁-C₇-alkyl, —(CO)—Rᵇ, —(CH₂)ₘ—Rᶜ, —NH—(CO)—C₁-C₇-alkyl, —O—CH₂F, —O—CHF₂, —O—CF₃, —S(O)₂—Rᵈ, C₃-C₆-cycloalkyl, or heteroaryl which is optionally substituted by C₁-C₇-alkyl; and
R⁴ is H, —OH, Cl, F, Br, CN, —CHF₂, CF₃, C₁-C₇-alkyl, —O—(CO)—C₁-C₇-alkyl, C₃-C₆-cycloalkyl, or —(CH₂)ₘ—Rᵉ;
or a pharmaceutically acceptable salt thereof.

5. The compound of claim 4, wherein:
R² is H or C₁-C₇-alkyl;
R₃ is phenyl or a 5- or 6-membered heteroaryl each of which is optionally substituted by:
  CN, Cl, F, Br, CF₃, CHF₂, —O—C₁-C₇-alkyl, —(CO)—Rᵇ, —(CH₂)ₘ—Rᶜ, —NH—(CO)—C₁-C₇-alkyl, —O—CH₂F, —O—CHF₂, —O—CF₃, —S(O)₂—Rᵈ, or heteroaryl which is optionally substituted by C₁-C₇-alkyl; and
R⁴ is H, —OH, Cl, F, Br, CN, —CHF₂, CF₃, C₁-C₇-alkyl, —O—(CO)—C₁-C₇-alkyl, or —(CH₂)ₘ—Rᵉ or a pharmaceutically acceptable salt thereof.

6. The compound of claim 5, selected from the group consisting of:
  6-Methyl-3-(pyridin-3-ylamino)-pyridine-2-carboxylic acid (4-methyl-thiazol-2-yl)-amide;
  6-Methyl-3-(pyrimidin-5-ylamino)-pyridine-2-carboxylic acid (4-methyl-thiazol-2-yl)-amide;
  6-Methyl-3-(pyridin-3-ylamino)-pyridine-2-carboxylic acid (4-trifluoromethyl-thiazol-2-yl)-amide;
  6-Methyl-3-(pyrimidin-5-ylamino)-pyridine-2-carboxylic acid (4-trifluoromethyl-thiazol-2-yl)-amide;
  6-Methyl-3-(4-methyl-pyridin-3-ylamino)-pyridine-2-carboxylic acid (4-methyl-thiazol-2-yl)-amide;
  3-(5-Cyano-pyridin-3-ylamino)-6-methyl-pyridine-2-carboxylic acid (4-methyl-thiazol-2-yl)-amide;
  6-Methyl-3-(2-methyl-pyridin-3-ylamino)-pyridine-2-carboxylic acid (4-methyl-thiazol-2-yl)-amide;
  3-(5-Fluoro-pyridin-3-ylamino)-6-methyl-pyridine-2-carboxylic acid (4-methyl-thiazol-2-yl)-amide;
  3-(3-Fluoro-phenylamino)-6-methyl-pyridine-2-carboxylic acid (4-methyl-thiazol-2-yl)-amide; and
  3-(3,5-Difluoro-phenylamino)-6-methyl-pyridine-2-carboxylic acid (4-methyl-thiazol-2-yl)-amide.

7. The compound of claim 5, selected from the group consisting of:
  6-Methyl-3-phenylamino-pyridine-2-carboxylic acid (4-methyl-thiazol-2-yl)-amide;
  3-(3-Cyano-5-fluoro-phenylamino)-6-methyl-pyridine-2-carboxylic acid (4-methyl-thiazol-2-yl)-amide;
  3-(3-Cyano-phenylamino)-6-methyl-pyridine-2-carboxylic acid (4-methyl-thiazol-2-yl)-amide;
  3-(2-Chloro-pyridin-4-ylamino)-6-methyl-pyridine-2-carboxylic acid (4-methyl-thiazol-2-yl)-amide;
  6-Methyl-3-(4-methyl-pyridin-3-ylamino)-pyridine-2-carboxylic acid (4-trifluoromethyl-thiazol-2-yl)-amide;
  3-(5-Cyano-pyridin-3-ylamino)-6-methyl-pyridine-2-carboxylic acid (4-trifluoromethyl-thiazol-2-yl)-amide;
  3-(3-Fluoro-phenylamino)-6-methyl-pyridine-2-carboxylic acid (4-trifluoromethyl-thiazol-2-yl)-amide;
  3-(3-Cyano-phenylamino)-6-methyl-pyridine-2-carboxylic acid (4-trifluoromethyl-thiazol-2-yl)-amide;
  3-(3,5-Difluoro-phenylamino)-6-methyl-pyridine-2-carboxylic acid (4-trifluoromethyl-thiazol-2-yl)-amide; and
  6-Methyl-3-(pyrimidin-5-ylamino)-pyridine-2-carboxylic acid (4-methoxymethyl-thiazol-2-yl)-amide.

8. The compound of claim 5, selected from the group consisting of:
  3-(3,5-Difluoro-phenylamino)-6-methyl-pyridine-2-carboxylic acid (4-methoxymethyl-thiazol-2-yl)-amide;
  3-(5-Fluoro-pyridin-3-ylamino)-6-methyl-pyridine-2-carboxylic acid (4-methoxymethyl-thiazol-2-yl)-amide;
  6-Methyl-3-(pyrimidin-5-ylamino)-pyridine-2-carboxylic acid (4-cyclopropyl-thiazol-2-yl)-amide;
  3-(5-Fluoro-pyridin-3-ylamino)-6-methyl-pyridine-2-carboxylic acid (4-cyclopropyl-thiazol-2-yl)-amide;
  6-Methyl-3-(pyridin-3-ylamino)-pyridine-2-carboxylic acid (4-cyclopropyl-thiazol-2-yl)-amide;
  3-(3,5-Difluoro-phenylamino)-6-methyl-pyridine-2-carboxylic acid (4-cyclopropyl-thiazol-2-yl)-amide;
  6-Methyl-3-(2-methyl-2H-pyrazol-3-ylamino)-pyridine-2-carboxylic acid (4-methyl-thiazol-2-yl)-amide;
  6-Methyl-3-(1-methyl-1H-pyrazol-4-ylamino)-pyridine-2-carboxylic acid (4-methyl-thiazol-2-yl)-amide;
  3-(2,5-Dimethyl-2H-pyrazol-3-ylamino)-6-methyl-pyridine-2-carboxylic acid (4-methyl-thiazol-2-yl)-amide; and
  6-Methyl-3-(5-methyl-pyridin-3-ylamino)-pyridine-2-carboxylic acid (4-methyl-thiazol-2-yl)-amide.

9. The compound of claim 5, selected from the group consisting of:
  3-(5-Cyclopropyl-2-methyl-2H-pyrazol-3-ylamino)-6-methyl-pyridine-2-carboxylic acid (4-methyl-thiazol-2-yl)-amide;
  6-Methyl-3-(pyrimidin-5-ylamino)-pyridine-2-carboxylic acid (4-methyl-thiazol-2-yl)-amide;
  6-Methyl-3-(pyrimidin-5-ylamino)-pyridine-2-carboxylic acid (4-hydroxymethyl-thiazol-2-yl)-amide;

6-Hydroxymethyl-3-(pyrimidin-5-ylamino)-pyridine-2-carboxylic acid (4-methyl-thiazol-2-yl)-amide;
6-Cyclopropyl-3-(pyridin-3-ylamino)-pyridine-2-carboxylic acid (4-methyl-thiazol-2-yl)-amide; and
6-Ethyl-3-(pyrimidin-5-ylamino)-pyridine-2-carboxylic acid (4-methyl-thiazol-2-yl)-amide.

10. A compound having formula (Id)

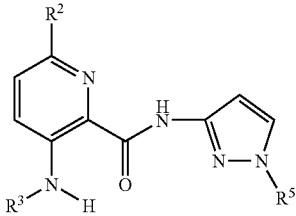

wherein:
R² is H or C₁-C₇-alkyl;
R³ is phenyl or a 5- or 6-membered heteroaryl each of which is optionally substituted by:
CN, Cl, F, Br, CF₃, CHF₂, —O—C₁-C₇-alkyl, —(CO)—R$^b$, —(CH₂)$_m$—R$^c$, —NH—(CO)—C₁-C₇-alkyl, O—CH₂F, —O—CHF₂, —O—CF₃, —S(O)₂—R$^d$, or heteroaryl which is optionally substituted by C₁-C₇-alkyl; and
R⁵ is C₁-C₇-alkyl, C₁-C₇-alkyl-C₃-C₆-cycloalkyl, —(CH₂)$_n$—O—R$^f$, C₃-C₈-alkenyl-O—R$^f$, —(CH₂)$_n$—NR$^g$R$^h$, —C₂-C₆-alkenyl -NR$^g$R$^h$, or —(CH₂)$_n$—R$^e$ or a pharmaceutically acceptable salt thereof.

11. The compound of claim 10, selected from the group consisting of:
6-Methyl-3-(pyridin-3-ylamino)-pyridine-2-carboxylic acid (1-methyl-1H-pyrazol-3-yl)-amide;
6-Methyl-3-(pyrimidin-5-ylamino)-pyridine-2-carboxylic acid (1-methyl-1H-pyrazol-3-yl)-amide;
3-(5-Cyano-pyridin-3-ylamino)-6-methyl-pyridine-2-carboxylic acid (1-methyl-1H-pyrazol-3-yl)-amide;
6-Methyl-3-(4-methyl-pyridin-3-ylamino)-pyridine-2-carboxylic acid (1-methyl-1H-pyrazol-3-yl)-amide;
6-Methyl-3-(2-methyl-pyridin-3-ylamino)-pyridine-2-carboxylic acid (1-methyl-1H-pyrazol-3-yl)-amide;
3-(5-Fluoro-pyridin-3-ylamino)-6-methyl-pyridine-2-carboxylic acid (1-methyl-1H-pyrazol-3-yl)-amide;
3-(3,5-Difluoro-phenylamino)-6-methyl-pyridine-2-carboxylic acid (1-methyl-1H-pyrazol-3-yl)-amide;
3-(3-Cyano-phenylamino)-6-methyl-pyridine-2-carboxylic acid (1-methyl-1H-pyrazol-3-yl)-amide;
3-(3-Fluoro-phenylamino)-6-methyl-pyridine-2-carboxylic acid (1-methyl-1H-pyrazol-3-yl)-amide; and
3-(3-Cyano-5-fluoro-phenylamino)-6-methyl-pyridine-2-carboxylic acid (1-methyl-1H-pyrazol-3-yl)-amide.

12. The compound of claim 10, selected from the group consisting of:
6-Methyl-3-phenylamino-pyridine-2-carboxylic acid (1-methyl-1H-pyrazol-3-yl)-amide;
3-(2-Chloro-pyridin-4-ylamino)-6-methyl-pyridine-2-carboxylic acid (1-methyl-1H-pyrazol-3-yl)-amide;
6-Methyl-3-(5-trifluoromethyl-pyridin-3-ylamino)-pyridine-2-carboxylic acid (1-methyl-1H-pyrazol-3-yl)-amide;
3-(3,5-Difluoro-phenylamino)-6-methyl-pyridine-2-carboxylic acid [1-(2-methoxy-ethyl)-1H-pyrazol-3-yl]-amide;
3-(5-Fluoro-pyridin-3-ylamino)-6-methyl-pyridine-2-carboxylic acid [1-(2-methoxy-ethyl)-1H-pyrazol-3-yl]-amide;
6-Methyl-3-(pyrimidin-5-ylamino)-pyridine-2-carboxylic acid [1-(2-methoxy-ethyl)-1H-pyrazol-3-yl]-amide;
3-(3-Cyano-phenylamino)-6-methyl-pyridine-2-carboxylic acid [1-(2-methoxy-ethyl)-1H-pyrazol-3-yl]-amide;
3-(4-Fluoro-pyridin-2-ylamino)-6-methyl-pyridine-2-carboxylic acid [1-(2-methoxy-ethyl)-1H-pyrazol-3-yl]-amide;
3-(3-Fluoro-phenylamino)-6-methyl-pyridine-2-carboxylic acid [1-(2-methoxy-ethyl)-1H-pyrazol-3-yl]-amide; and
3-(3-Cyano-5-fluoro-phenylamino)-6-methyl-pyridine-2-carboxylic acid [1-(2-methoxy-ethyl)-1H-pyrazol-3-yl]-amide.

13. The compound of claim 10, selected from the group consisting of:
6-Methyl-3-(1-methyl-1H-pyrazol-3-ylamino)-pyridine-2-carboxylic acid (1-methyl-1H-pyrazol-3-yl)-amide;
3-(4-Fluoro-phenylamino)-6-methyl-pyridine-2-carboxylic acid (1-methyl-1H-pyrazol-3-yl)-amide;
6-Methyl-3-(4-methyl-thiazol-2-ylamino)-pyridine-2-carboxylic acid (1-methyl-1H-pyrazol-3-yl)-amide;
6-Methyl-3-(pyrazin-2-ylamino)-pyridine-2-carboxylic acid (1-methyl-1H-pyrazol-3-yl)-amide;
6-Methyl-3-(2-methyl-2H-pyrazol-3-ylamino)-pyridine-2-carboxylic acid (1-methyl-1H-pyrazol-3-yl)-amide;
6-Methyl-3-(1-methyl-1H-pyrazol-4-ylamino)-pyridine-2-carboxylic acid (1-methyl-1H-pyrazol-3-yl)-amide;
3-(2,5-Dimethyl-2H-pyrazol-3-ylamino)-6-methyl-pyridine-2-carboxylic acid (1-methyl-1H-pyrazol-3-yl)-amide;
6-Methyl-3-(6-methyl-pyrazin-2-ylamino)-pyridine-2-carboxylic acid (1-methyl-1H-pyrazol-3-yl)-amide;
6-Methyl-3-(4-methyl-pyrimidin-5-ylamino)-pyridine-2-carboxylic acid (1-methyl-1H-pyrazol-3-yl)-amide; and
3-(5-Fluoro-6-methyl-pyridin-2-ylamino)-6-methyl-pyridine-2-carboxylic acid (1-methyl-1H-pyrazol-3-yl)-amide.

14. The compound of claim 10, selected from the group consisting of:
3-(5-Chloro-pyridin-3-ylamino)-6-methyl-pyridine-2-carboxylic acid (1-methyl-1H-pyrazol-3-yl)-amide;
6-Methyl-3-(5-methyl-pyridin-3-ylamino)-pyridine-2-carboxylic acid (1-methyl-1H-pyrazol-3-yl)-amide;
3-(5-Cyclopropyl-2-methyl-2H-pyrazol-3-ylamino)-6-methyl-pyridine-2-carboxylic acid (1-methyl-1H-pyrazol-3-yl)-amide;
6-Cyclopropyl-3-(pyrimidin-5-ylamino)-pyridine-2-carboxylic acid (1-methyl-1H-pyrazol-3-yl)-amide; and
6-Cyclopropyl-3-(pyridin-3-ylamino)-pyridine-2-carboxylic acid (1-methyl-1H-pyrazol-3-yl)-amide.

15. A compound having formula (Ie)

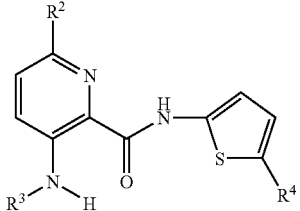

wherein:

$R^2$ is H or $C_1$-$C_7$-alkyl;

$R^3$ is phenyl or a 5- or 6-membered heteroaryl each of which is optionally substituted by:
CN, Cl, F, Br, $CF_3$, $CHF_2$, —O—$C_1$-$C_7$-alkyl, —(CO)—$R^b$, —(CH$_2$)$_m$—$R^c$, —NH—(CO)—$C_1$-$C_7$-alkyl, —O—CH$_2$F, —O—CHF$_2$, —O—CF$_3$, —S(O)$_2$—$R^d$, or heteroaryl which is optionally substituted by $C_1$-$C_7$-alkyl; and $R^4$ is H, —OH, Cl, F, Br, CN, —CHF$_2$, CF$_3$, $C_1$-$C_7$-alkyl, —O—(CO)—$C_1$-$C_7$-alkyl, or —(CH$_2$)$_m$—$R^e$ or a pharmaceutically acceptable salt thereof.

16. A compound having formula (If)

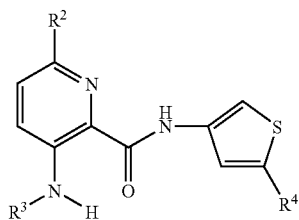
(If)

wherein:

$R^2$ is H or $C_1$-$C_7$-alkyl;

$R^3$ is phenyl or a 5- or 6-membered heteroaryl each of which is optionally substituted by:
CN, Cl, F, Br, $CF_3$, $CHF_2$, —O—$C_1$-$C_7$-alkyl, —(CO)—$R^b$, —(CH$_2$)$_m$—$R^c$, —NH—(CO)—$C_1$-$C_7$-alkyl, —O—CH$_2$F, —O—CHF$_2$, —O—CF$_3$, —S(O)$_2$—$R^d$, or heteroaryl which is optionally substituted by $C_1$-$C_7$-alkyl; and $R^4$ is H, —OH, Cl, F, Br, CN, —CHF$_2$, CF$_3$, $C_1$-$C_7$-alkyl, —O—(CO)—$C_1$-$C_7$-alkyl, or —(CH$_2$)$_m$—$R^e$ or a pharmaceutically acceptable salt thereof.

17. A compound having formula (Ig)

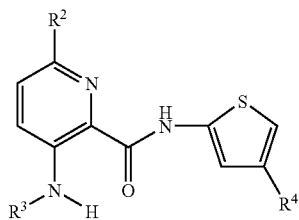
(Ig)

wherein:

$R^2$ is H or $C_1$-$C_7$-alkyl;

$R^3$ is phenyl or a 5- or 6-membered heteroaryl each of which is optionally substituted by:
CN, Cl, F, Br, $CF_3$, $CHF_2$, —O—$C_1$-$C_7$-alkyl, —(CO)—$R^b$, —(CH$_2$)$_m$—$R^c$, —NH—(CO)—$C_1$-$C_7$-alkyl, —O—CH$_2$F, —O—CHF$_2$, —O—CF$_3$, —S(O)$_2$—$R^d$, or heteroaryl which is optionally substituted by $C_1$-$C_7$-alkyl; and $R^4$ is H, —OH, Cl, F, Br, CN, —CHF$_2$, CF$_3$, $C_1$-$C_7$-alkyl, —O—(CO)—$C_1$-$C_7$-alkyl, or —(CH$_2$)$_m$—$R^e$ or a pharmaceutically acceptable salt thereof.

18. A compound having formula (Ih)

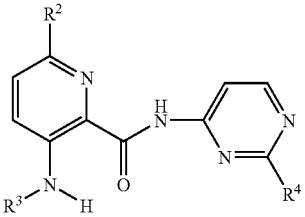
(Ih)

wherein:

$R^2$ is H or $C_1$-$C_7$-alkyl;

$R^3$ is phenyl or a 5- or 6-membered heteroaryl each of which is optionally substituted by:
CN, Cl, F, Br, $CF_3$, $CHF_2$, —O—$C_1$-$C_7$-alkyl, —(CO)—$R^b$, —(CH$_2$)$_m$—$R^c$, —NH—(CO)—$C_1$-$C_7$-alkyl, —O—CH$_2$F, —O—CHF$_2$, —O—CF$_3$, —S(O)$_2$—$R^d$, or heteroaryl which is optionally substituted by $C_1$-$C_7$-alkyl; and $R^4$ is H, —OH, Cl, F, Br, CN, —CHF$_2$, CF$_3$, $C_1$-$C_7$-alkyl, —O—(CO)—$C_1$-$C_7$-alkyl, or —(CH$_2$)$_m$—$R^e$ or a pharmaceutically acceptable salt thereof.

19. A pharmaceutical composition comprising a therapeutically effective amount of a compound selected from the group consisting of

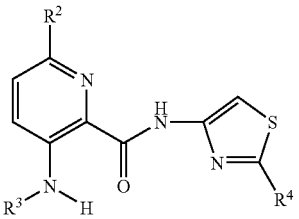
(Ib)

wherein $R^2$ is H, $C_1$-$C_7$-alkyl, $C_3$-$C_6$-cycloalkyl, or —(CH$_2$)$_m$—$R^a$;

$R^3$ is aryl or a 5- or 6-membered heteroaryl each of which is optionally substituted by:
CN, Cl, F, Br, $CF_3$, $CHF_2$, —O—$C_1$-$C_7$-alkyl, —(CO)—$R^b$, —(CH$_2$)$_m$—$R^c$, —NH—(CO)—$C_1$-$C_7$-alkyl, —O—CH$_2$F, —O—CHF$_2$, —O—CF$_3$, —S(O)$_2$—$R^d$, $C_3$-$C_6$-cycloalkyl, or heteroaryl which is optionally substituted by $C_1$-$C_7$-alkyl; and $R^4$ is H, —OH, Cl, F, Br, CN, —CHF$_2$, CF$_3$, $C_1$-$C_7$-alkyl, —O—(CO)—$C_1$-$C_7$-alkyl, $C_3$-$C_6$-cycloalkyl, or —(CH$_2$)$_m$—$R^e$;

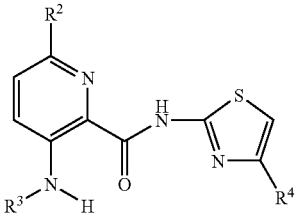
(Ic)

wherein $R^2$ is H, $C_1$-$C_7$-alkyl, $C_3$-$C_6$-cycloalkyl, or —(CH$_2$)$_m$—$R^a$;

$R^3$ is aryl or a 5- or 6-membered heteroaryl each of which is optionally substituted by:
CN, Cl, F, Br, $CF_3$, $CHF_2$, —O—$C_1$-$C_7$-alkyl, —(CO)—$R^b$, —(CH$_2$)$_m$—$R^c$, —NH—(CO)—$C_1$-$C_7$-alkyl, —O—CH$_2$F, —O—CHF$_2$, —O—CF$_3$, —S(O)$_2$—$R^d$, $C_3$-$C_6$-cycloalkyl, or heteroaryl which is optionally substituted by $C_1$-$C_7$-alkyl; and R⁴ is H, —OH, Cl, F, Br, CN, —CHF₂, CF₃, C₁-C₇-alkyl, —O—(CO)—C₁-C₇-alkyl, C₃-C₆-cycloalkyl, or —(CH₂)ₘ—Rᵉ;

(Id)

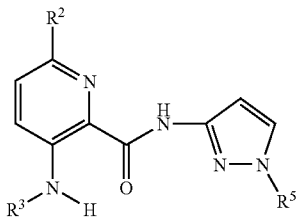

wherein:
R² is H or C₁-C₇-alkyl;
R³ is phenyl or a 5- or 6-membered heteroaryl each of which is optionally substituted by:
CN, Cl, F, Br, CF₃, CHF₂, —O—C₁-C₇-alkyl, —(CO)—Rᵇ, —(CH₂)ₘ—Rᶜ, —NH—(CO)—C₁-C₇-alkyl, —O—CH₂F, —O—CHF₂, —O—CF₃, —S(O)₂—Rᵈ, or heteroaryl which is optionally substituted by C₁-C₇-alkyl; and
R⁵ is C₁-C₇-alkyl, C₁-C₇-alkyl-C₃-C₆-cycloalkyl, —(CH₂)ₙ—O—Rᶠ, C₃-C₈-alkenyl-O—Rᶠ, —(CH₂)ₙ—NRᵍRʰ, or —C₂-C₆-alkenyl-NRᵍRʰ, or —(CH₂)ₙ—Rᵉ;

(Ie)

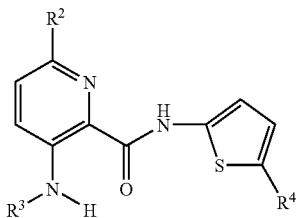

wherein:
R² is H or C₁-C₇-alkyl;
R³ is phenyl or a 5- or 6-membered heteroaryl each of which is optionally substituted by:
CN, Cl, F, Br, CF₃, CHF₂, —O—C₁-C₇-alkyl, —(CO)—Rᵇ, —(CH₂)ₘ—Rᶜ, —NH—(CO)—C₁-C₇-alkyl, —O—CH₂F, —O—CHF₂, —O—CF₃, —S(O)₂—Rᵈ, or heteroaryl which is optionally substituted by C₁-C₇-alkyl; and
R⁴ is H, —OH, Cl, F, Br, CN, —CHF₂, CF₃, C₁-C₇-alkyl, —O—(CO)—C₁-C₇-alkyl, or —(CH₂)ₘ—Rᵉ;

(If)

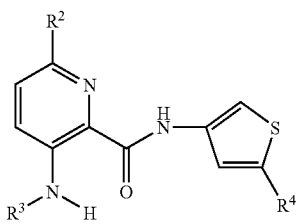

wherein:
R² is H or C₁-C₇-alkyl;
R³ is phenyl or a 5- or 6-membered heteroaryl each of which is optionally substituted by:
CN, Cl, F, Br, CF₃, CHF₂, —O—C₁-C₇-alkyl, —(CO)—Rᵇ, —(CH₂)ₘ—Rᶜ, —NH—(CO)—C₁-C₇alkyl, —O—CH₂F, —O—CHF₂, —O—CF₃, —S(O)₂—Rᵈ, or heteroaryl which is optionally substituted by C₁-C₇-alkyl; and
R⁴ is H, —OH, Cl, F, Br, CN, —CHF₂, CF₃, C₁-C₇-alkyl, —O—(CO)—C₁-C₇-alkyl, or —(CH₂)ₘ—Rᵉ;

(Ig)

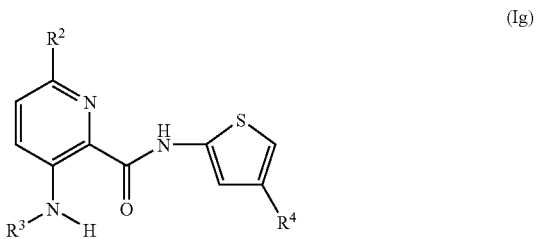

wherein:
R² is H, C₁-C₇-alkyl;
R³ is phenyl or a 5- or 6-membered heteroaryl each of which is optionally substituted by:
CN, Cl, F, Br, CF₃, CHF₂, —O—C₁-C₇-alkyl, —(CO)—Rᵇ, —(CH₂)ₘ—Rᶜ, —NH—(CO)—C₁C₇alkyl, —O—CH₂F, —O—CHF₂, —O—CF₃, —S(O)₂—Rᵈ, or heteroaryl which is optionally substituted by C₁-C₇-alkyl; and
R⁴ is H, —OH, Cl, F, Br, CN, —CHF₂, CF₃, C₁-C₇-alkyl, —O—(CO)—C₁-C₇-alkyl, or —(CH₂)ₘ—Rᵉ;
and (Ih)

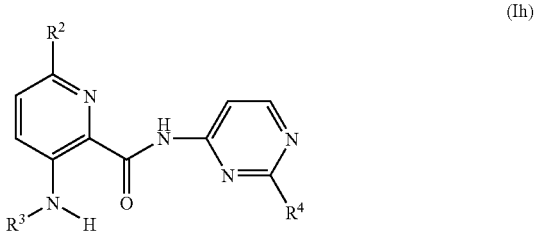

wherein:
R² is H or C₁-C₇-alkyl;
R³ is phenyl or a 5- or 6-membered heteroaryl each of which is optionally substituted by:
CN, Cl, F, Br, CF₃, CHF₂, —O—C₁-C₇-alkyl, —(CO)—Rᵇ, —(CH₂)ₘ—Rᶜ, —NH—(CO)—C₁-C₇alkyl, —O—CH₂F, —O—CHF₂, —O—CF₃, —S(O)₂—Rᵈ, or heteroaryl which is optionally substituted by C₁-C₇-alkyl; and
R⁴ is H, —OH, Cl, F, Br, CN, —CHF₂, CF₃, C₁-C₇-alkyl, —O—(CO)—C₁-C₇-alkyl, or —(CH₂)ₘ—Rᵉ;
or a pharmaceutically acceptable salt thereof and a pharmaceutically acceptable carrier.

* * * * *